(12) United States Patent
Westby et al.

(10) Patent No.: US 11,766,483 B2
(45) Date of Patent: *Sep. 26, 2023

(54) COMPOUNDS AND THERAPEUTICS USES THEREOF

(71) Applicant: Centauri Therapeutics Limited (GB/GB), London (GB)

(72) Inventors: Michael Westby, Kent (GB); Melanie Glossop, Kent (GB); Christine Watson, Kent (GB); Christopher Pickford, Kent (GB)

(73) Assignee: CENTAURI THERAPEUTICS LIMITED (GB/GB), London (GB)

( * ) Notice: Subject to any disclaimer, the term of this patent is extended or adjusted under 35 U.S.C. 154(b) by 417 days.

This patent is subject to a terminal disclaimer.

(21) Appl. No.: 16/603,579

(22) PCT Filed: Apr. 6, 2018

(86) PCT No.: PCT/GB2018/050928
§ 371 (c)(1),
(2) Date: Oct. 7, 2019

(87) PCT Pub. No.: WO2018/185495
PCT Pub. Date: Oct. 11, 2018

(65) Prior Publication Data
US 2020/0147236 A1 May 14, 2020

(30) Foreign Application Priority Data
Apr. 7, 2017 (GB) .................................. 1705686

(51) Int. Cl.
| A61K 51/00 | (2006.01) |
| A61M 36/14 | (2006.01) |
| A61K 47/68 | (2017.01) |
| C07C 69/92 | (2006.01) |
| C07H 15/18 | (2006.01) |

(52) U.S. Cl.
CPC ...... *A61K 47/6897* (2017.08); *A61K 47/6849* (2017.08); *C07C 69/92* (2013.01); *C07H 15/18* (2013.01)

(58) Field of Classification Search
CPC ................ A61K 47/6897; A61K 45/06; A61K 2039/505; C07C 69/92; C07C 69/84; C07H 15/18; C07H 15/26; A61P 35/00; A61P 31/04; A61P 35/02
See application file for complete search history.

(56) References Cited

U.S. PATENT DOCUMENTS

| 6,831,106 B1 | 12/2004 | Bernardon et al. |
| 10,953,100 B2 * | 3/2021 | Pickford ................. A61P 31/00 |
| 11,014,966 B2 * | 5/2021 | Glossop ................. A61K 47/61 |
| 2010/0173323 A1 * | 7/2010 | Strome ............. C07K 16/2863 |
| | | 435/68.1 |

FOREIGN PATENT DOCUMENTS

| EP | 1882684 A1 | 1/2008 |
| EP | 2590942 A1 | 5/2013 |
| WO | 9834957 A1 | 8/1998 |
| WO | 03016464 A2 | 2/2003 |
| WO | 2004017810 A2 | 3/2004 |
| WO | 2005079423 A2 | 9/2005 |
| WO | 2009108807 A1 | 9/2009 |
| WO | 2013139697 A1 | 9/2013 |
| WO | 2013166110 A1 | 11/2013 |
| WO | 2017060728 A1 | 4/2017 |
| WO | 2017060729 A1 | 4/2017 |

OTHER PUBLICATIONS

Qian et al. (Analyt. Biochem. 2007, 364, 8-18).*
Banerjee Amalendu et al: "Use of phosphorus pentoxide. Preparation of half-esters through selective esterification", Journal of the Indian Chemical Society, Indian Chemical Society, IN, vol. 64, No. 1, 1987, pp. 34-37.
De Marchi F et al, Synthesis of pharmacological evaluation of some N-diethylaminoethylaryloxyacetamides and related compounds, Farmaco, Edizione Scientifica, Societa Chimica Italiana, Pavia, IT, vol. 28. No 1973, pp. 511-522.
G. E. Winter et al: "Phthalimide conjugation as a strategy for in vivo target protein degradation", Science, vol. 348, No. 6241, Jun. 19, 2015 (Jun. 19, 2015), pp. 1376-1381.
I. Dovgan et al, "2-(Maleimidomethyl)-1,3-Dioxanes (MD): A serum-stable self-hydrolysable hydrophilic alternative to classical maleimide conjugation", Nature Scientific Reports, (2016), 6, 30835.
Kosaku Hirota et al.: "Pyrimidine derivatives and related compounds. 39. A novel cycloaromatization reaction of 5-formyl-1,3-dimethyluracil with three-carbon nucleophiles. Synthesis of substituted 4-hydroxybenzoates", Journal of Organic Chemistry, vol. 46, No. 20, 1981, pp. 3949-3953.

* cited by examiner

*Primary Examiner* — Michael G. Hartley
*Assistant Examiner* — Melissa J Perreira
(74) *Attorney, Agent, or Firm* — Aura IP Law, PC

(57) ABSTRACT

The invention relates to novel compounds with the ability to link an immune response to a defined therapeutic target, to the use of said compounds in treating cancer and infectious diseases, to compositions containing said compounds, processes for their preparation and to novel intermediates used in said process.

35 Claims, 20 Drawing Sheets
Specification includes a Sequence Listing.

Example 5
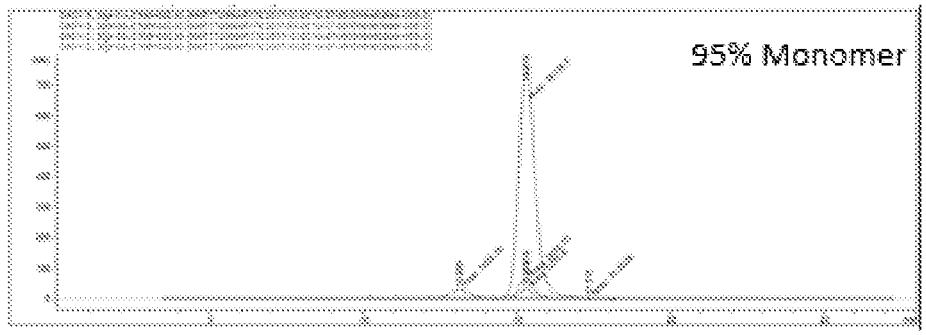
Example 6
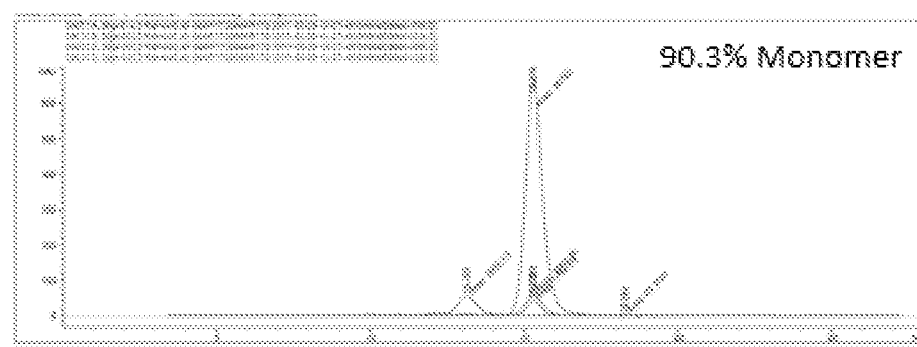
Example 7
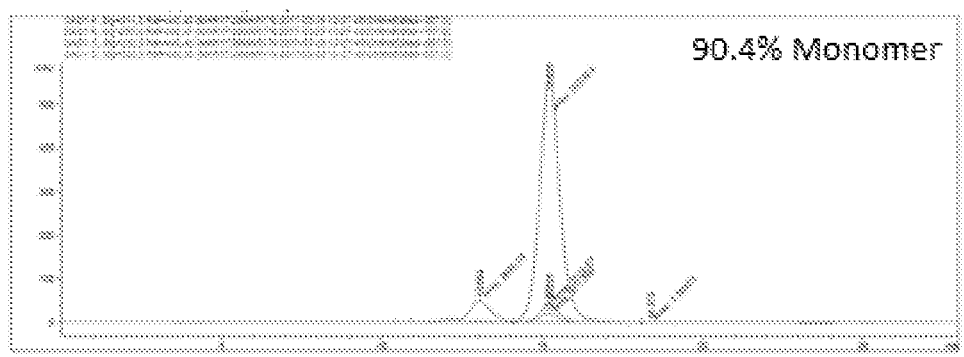
Example 8
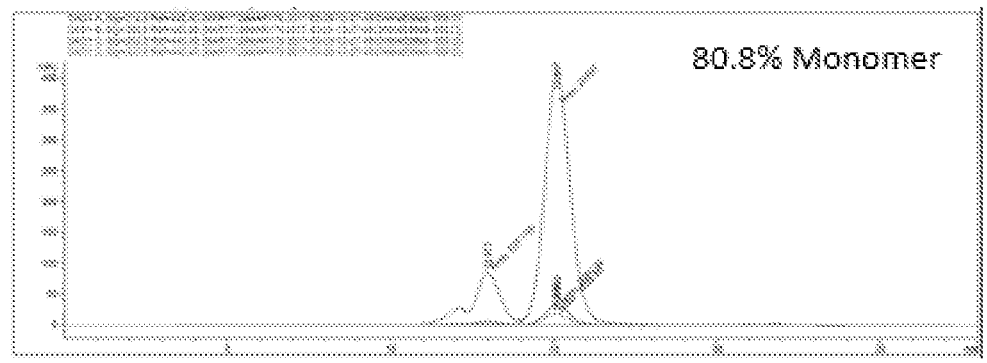
FIGURE 3 (ctd)

A

B

C

D
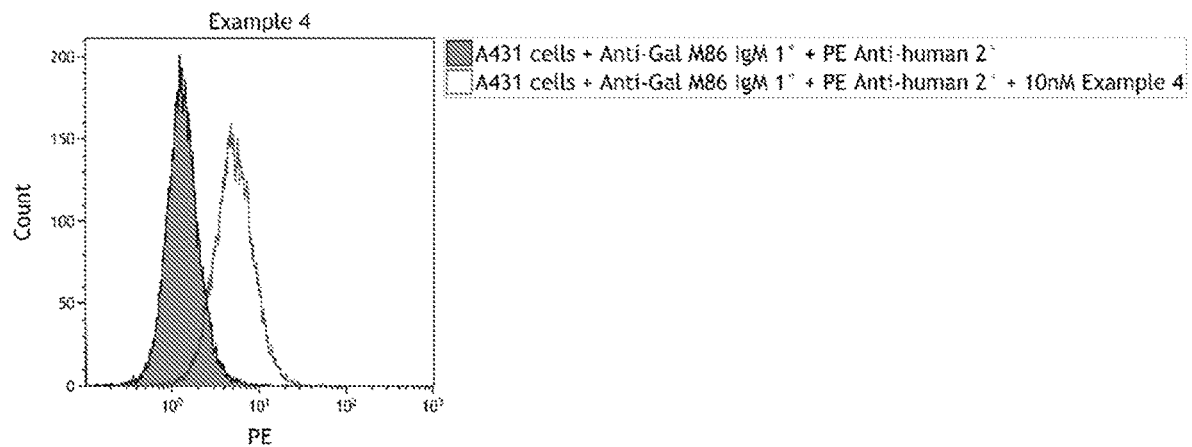
E
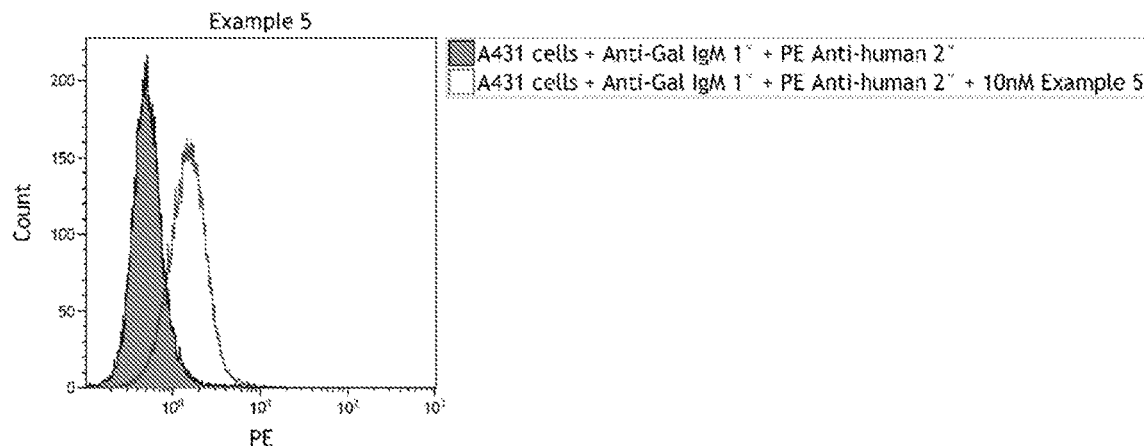
F
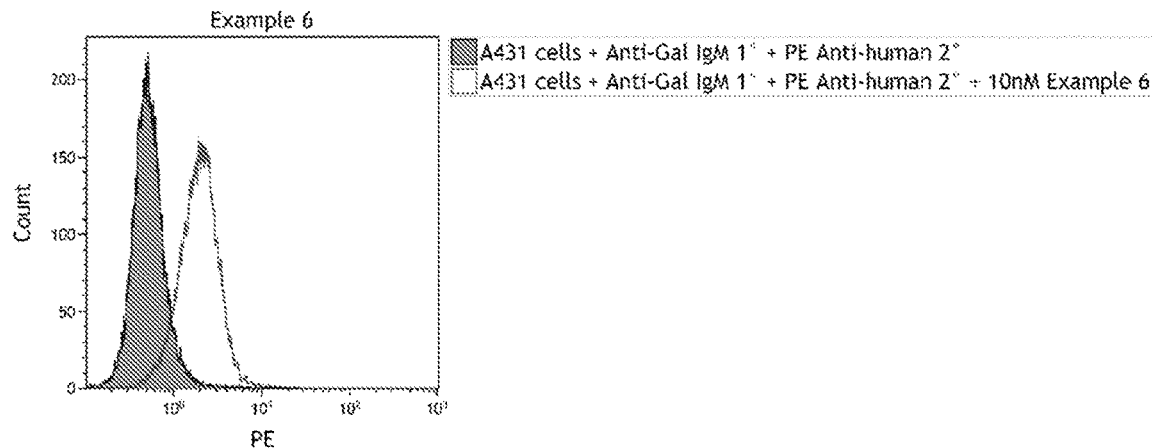
FIGURE 4 (ctd)

G
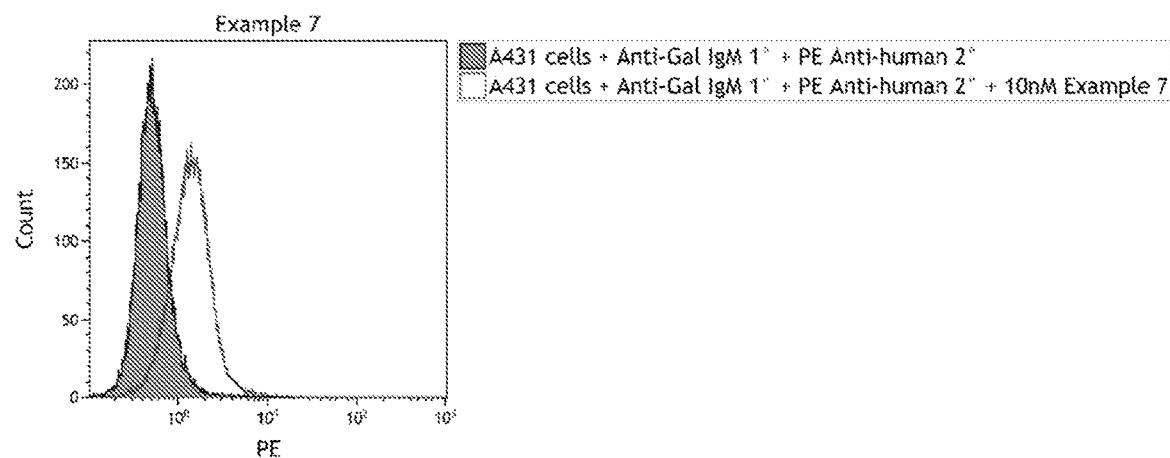
H
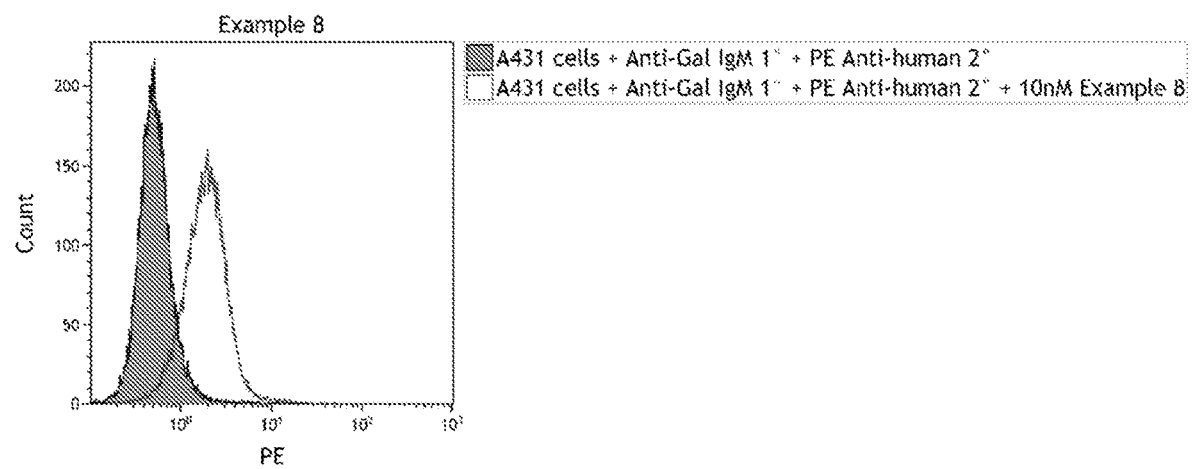
FIGURE 4 (ctd)

A

B

C
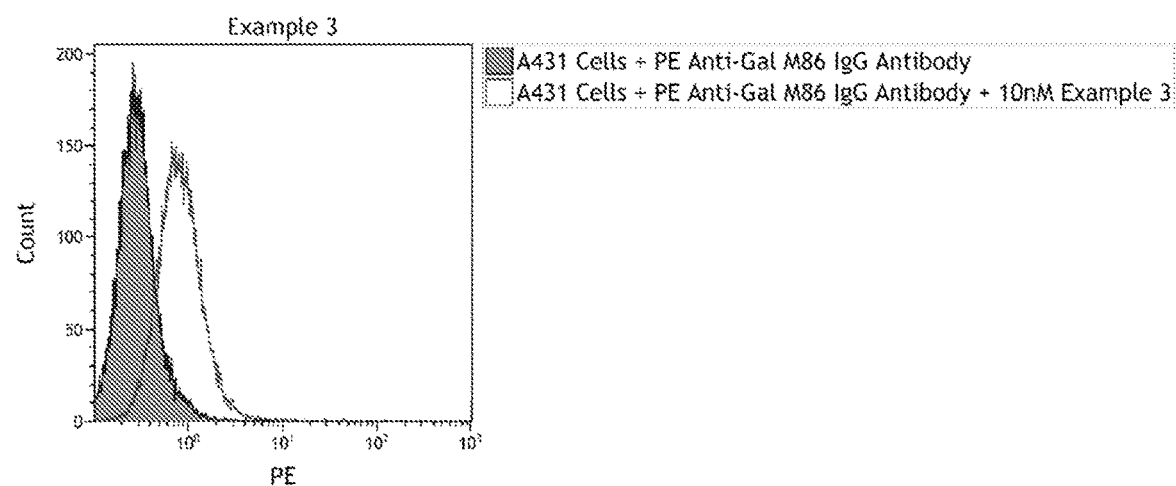
D
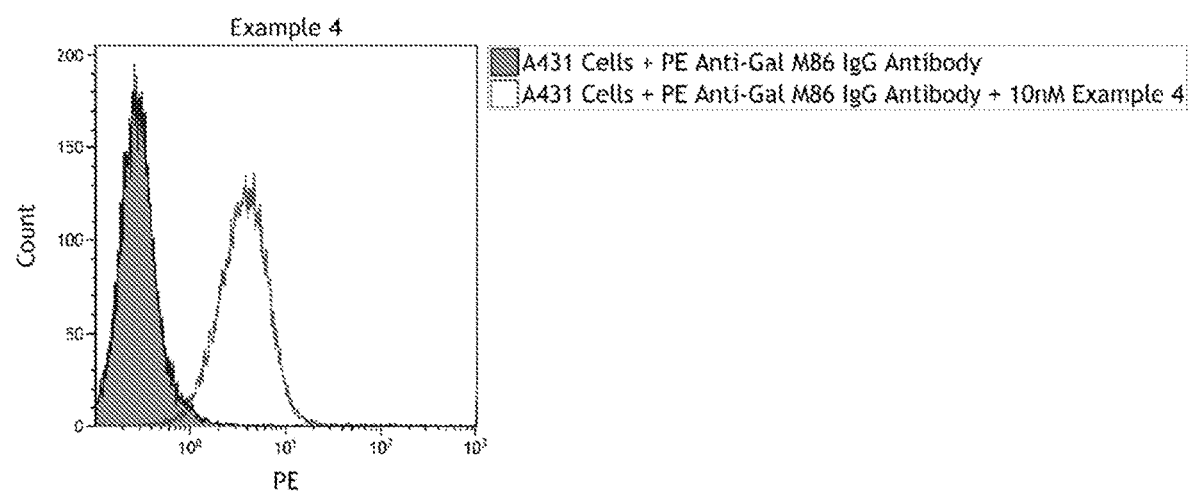
FIGURE 5 (ctd)

A

B

C
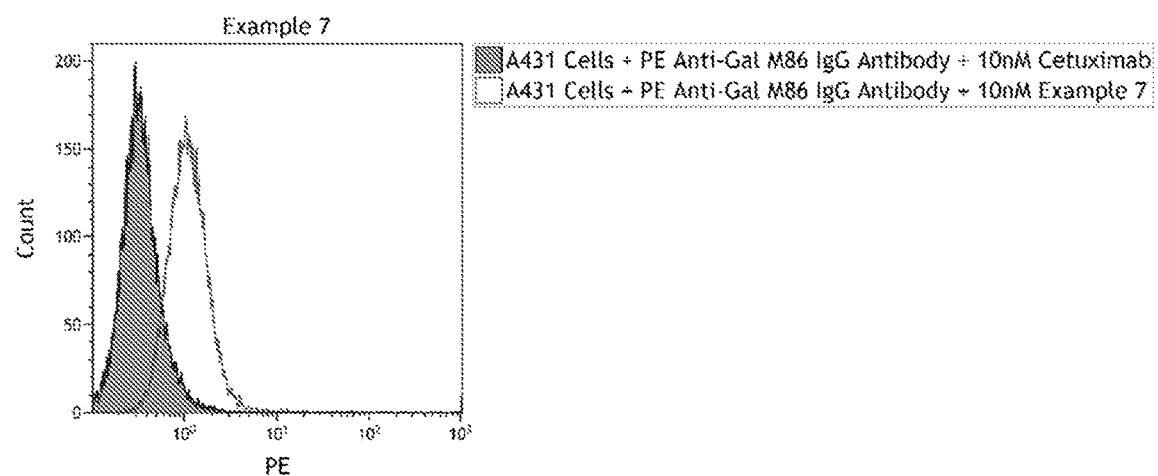
D
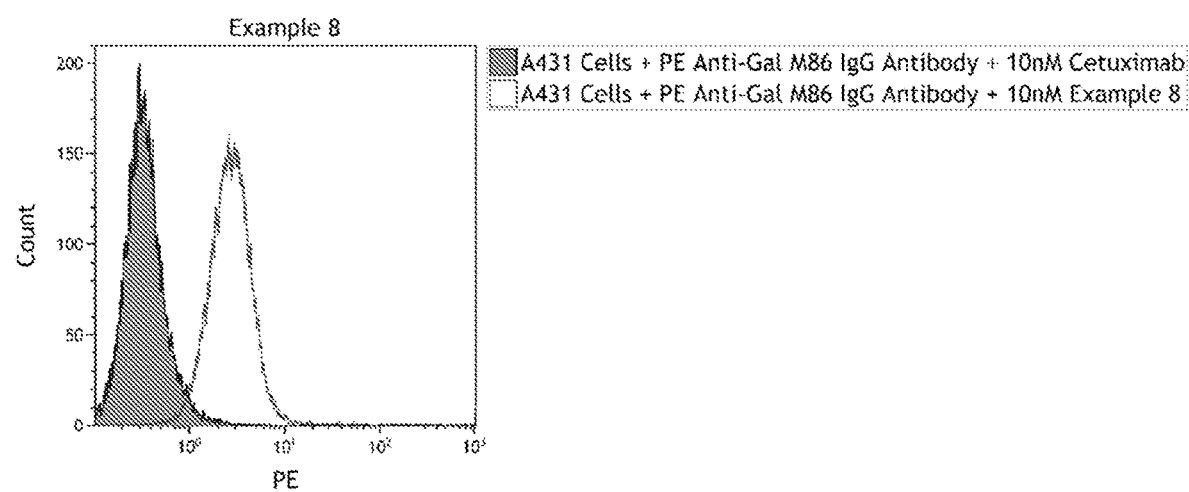
FIGURE 6 (ctd)

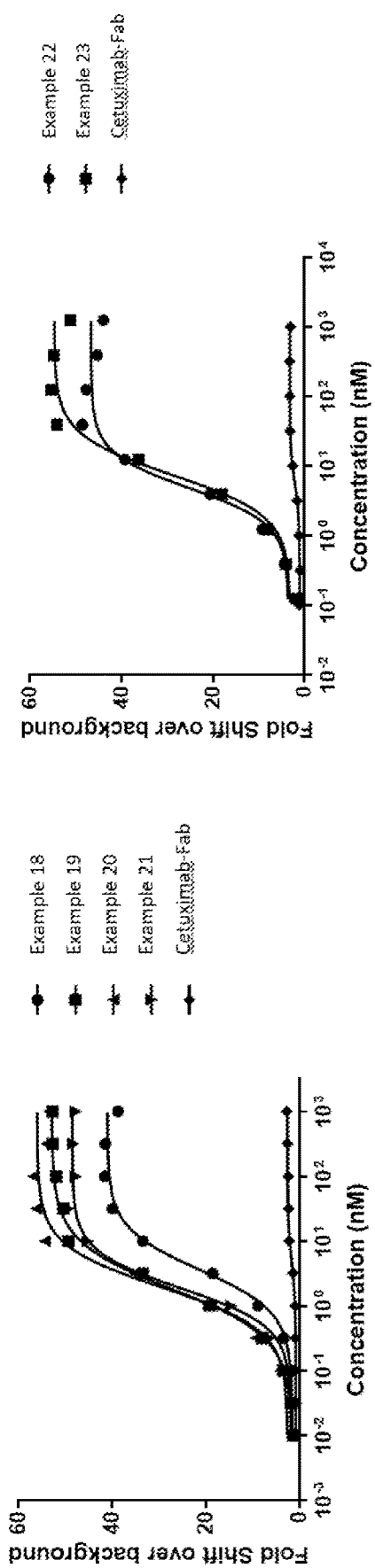
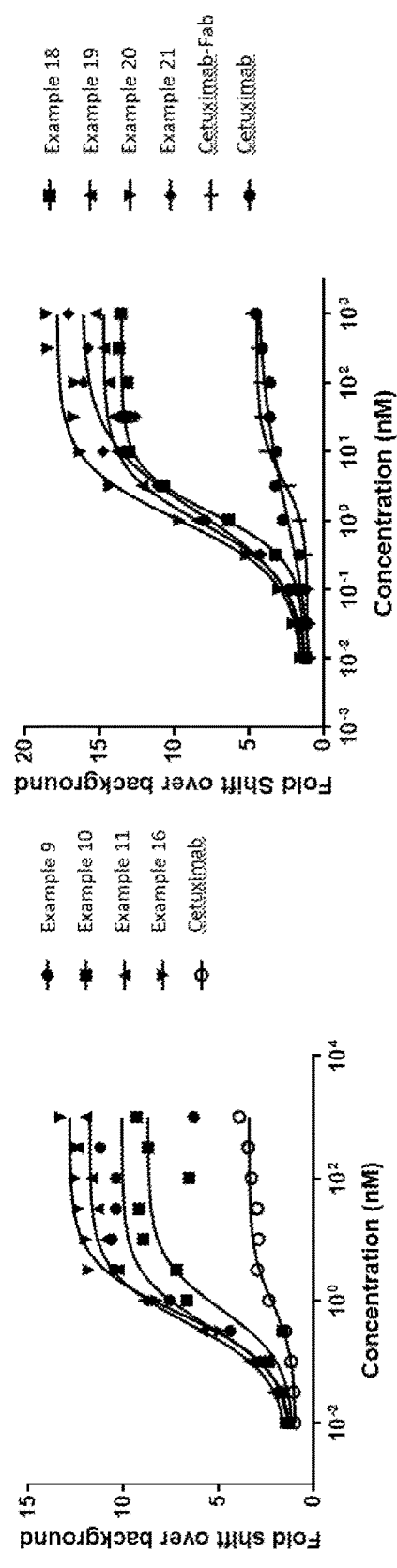
FIGURE 7A
FIGURE 7B
FIGURE 8A
FIGURE 8B

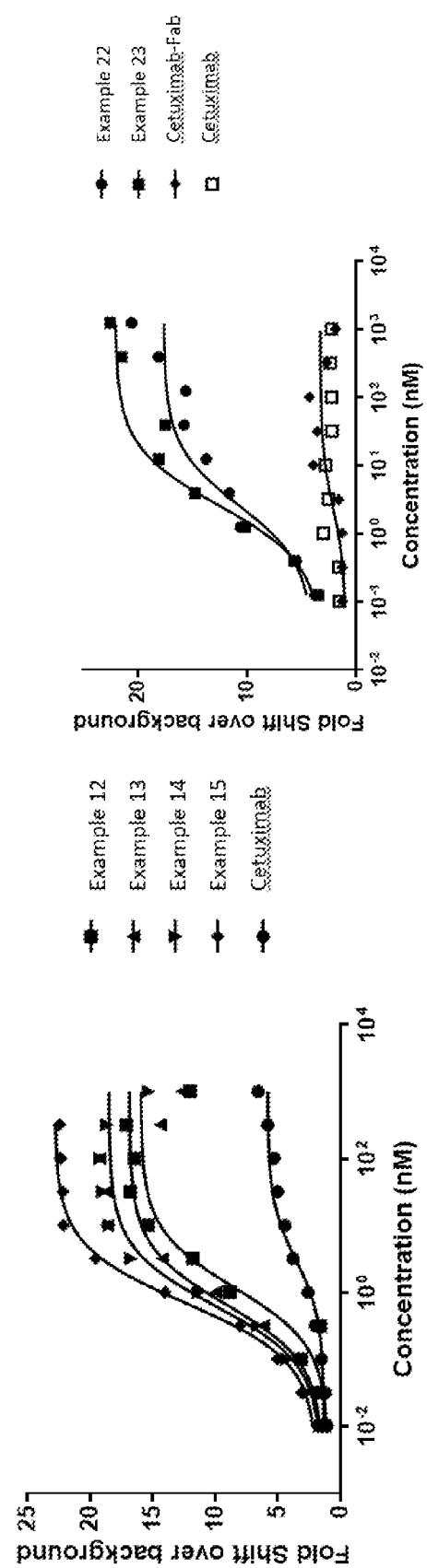
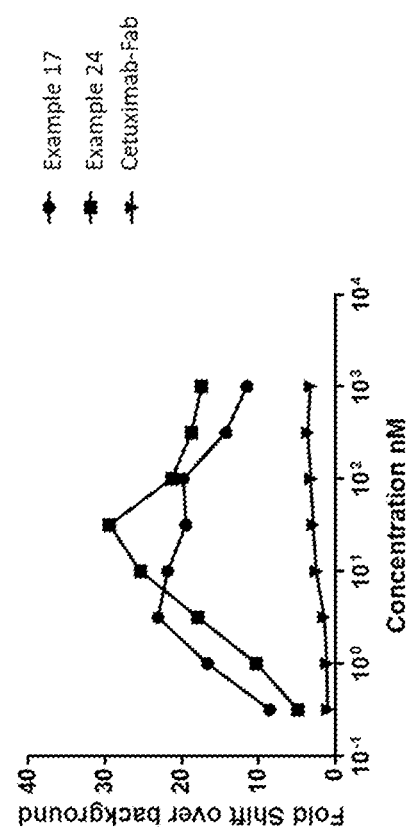
FIGURE 8C
FIGURE 8D
FIGURE 8E

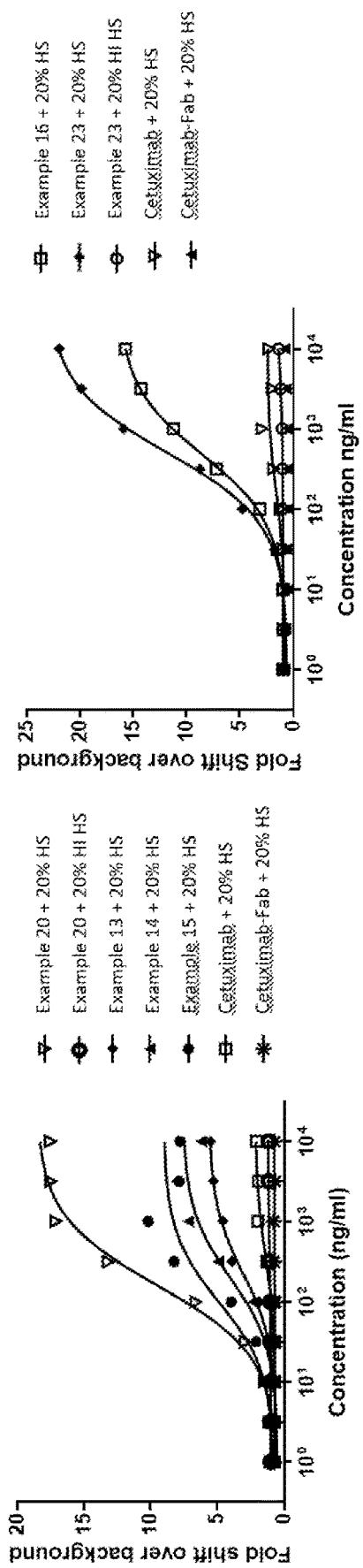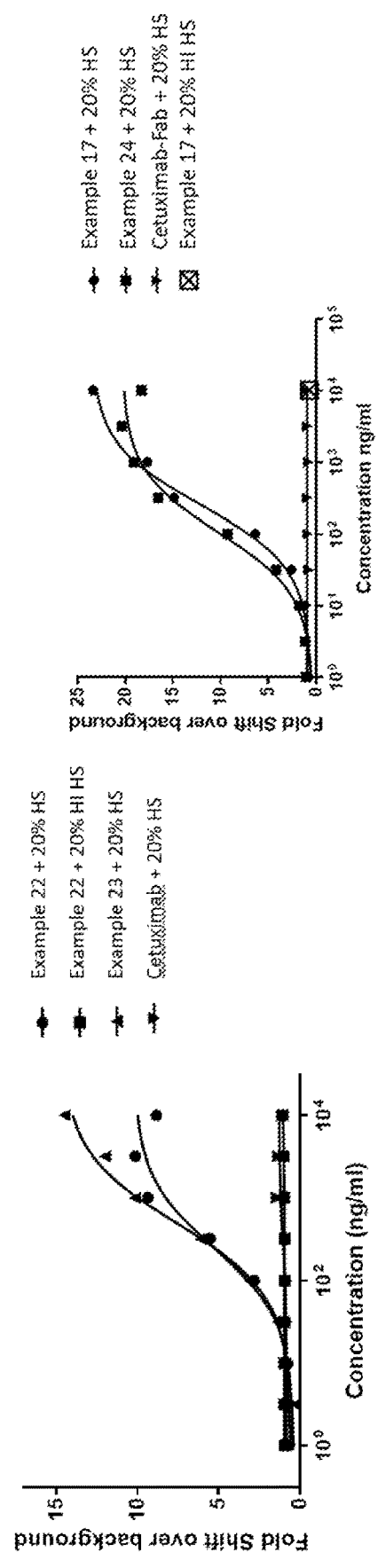
FIGURE 9A
FIGURE 9B
FIGURE 9C
FIGURE 9D

Figure 13A Legend
Lane 1: Cetuximab-Fab
Lane 2: Example 18
Lane 3: 1:1 Cetuximab-Fab:Example 18
Lane 4: Example 19
Lane 5: 1:1 Cetuximab-Fab:Example 19

Figure 13C Legend
Lane 1: Cetuximab-Fab
Lane 2: Example 20
Lane 3: Example 22
Lane 4: Example 23

Figure 12C Legend
Lane 1: Cetuximab
Lane 2: Example 17

Figure 13B Legend
Lane 1: Cetuximab-Fab
Lane 2: Example 20
Lane 3: 1:1 Cetuximab-Fab:Example 20
Lane 4: Example 21
Lane 5: 1:1 Cetuximab-Fab:Example 21

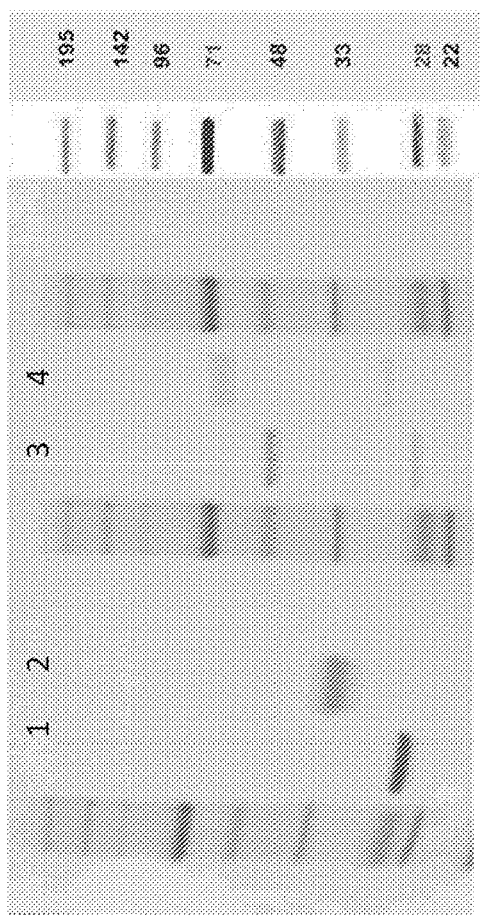
FIGURE 15A
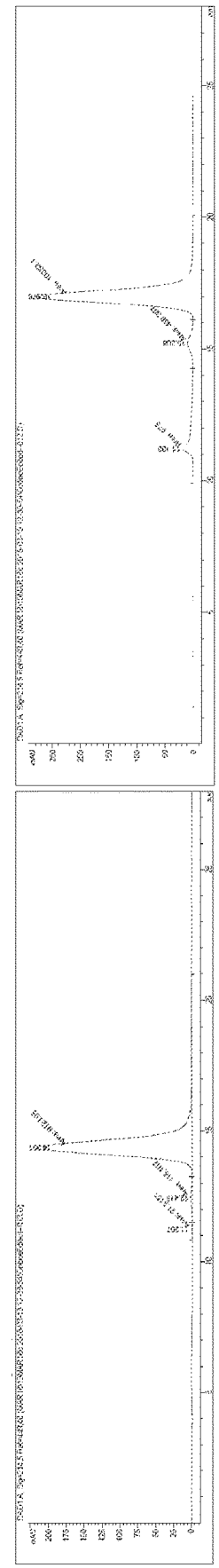
FIGURE 15B
FIGURE 15C

Figure 16A Legend
1: Cetuximab digest (Fc and FAB)
2: Purified FAB
3: Cetuximab
4: Cetuximab digest (Fc and FAB)
5: Purified FAB Non-reducing    Reducing

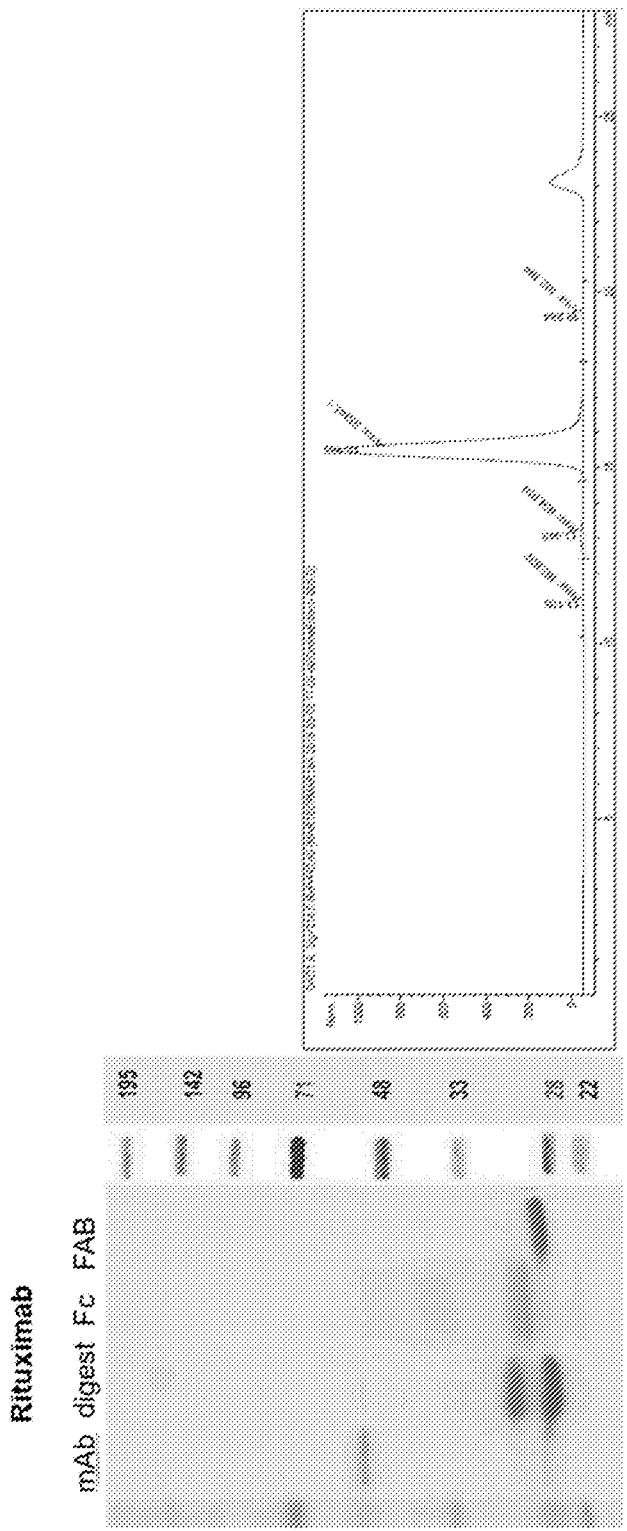
FIGURE 17A
FIGURE 17B
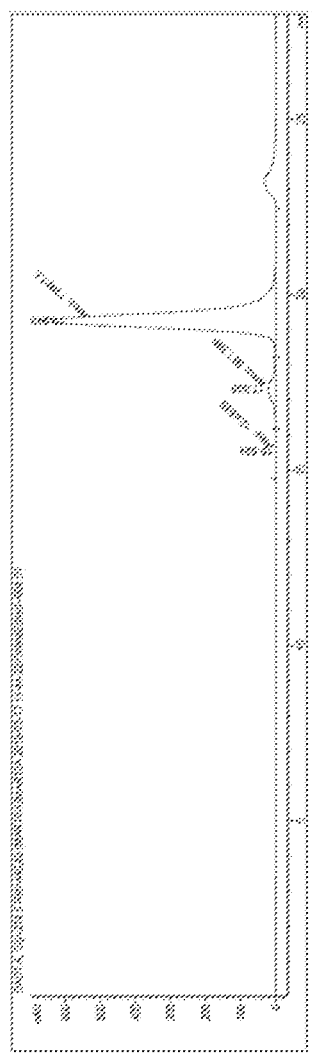
FIGURE 17C

SEQUENCE LISTING

```
<160> NUMBER OF SEQ ID NOS: 4

<210> SEQ ID NO 1
<211> LENGTH: 449
<212> TYPE: PRT
<213> ORGANISM: Artificial
<220> FEATURE:
<223> OTHER INFORMATION: Hybrid Mouse/Human

<400> SEQUENCE: 1

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240
```

```
Ser Val Phe Leu Phe Pro Pro Lys Pro Lys Asp Thr Leu Met Ile Ser
                245             250                 255

Arg Thr Pro Glu Val Thr Cys Val Val Val Asp Val Ser His Glu Asp
            260             265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 2
<211> LENGTH: 214
<212> TYPE: PRT
<213> ORGANISM: Artificial
<220> FEATURE:
<223> OTHER INFORMATION: Hybrid Mouse/Human

<400> SEQUENCE: 2

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 3
<211> LENGTH: 451
<212> TYPE: PRT
<213> ORGANISM: Artificial
<220> FEATURE:
<223> OTHER INFORMATION: Hybrid Mouse/Human

<400> SEQUENCE: 3

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Ala Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285
```

```
His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 4
<211> LENGTH: 213
<212> TYPE: PRT
<213> ORGANISM: Artificial
<220> FEATURE:
<223> OTHER INFORMATION: Hybrid Mouse/Human

<400> SEQUENCE: 4

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190
```

```
Cys Glu Val Thr His Gln Gly Leu Ser Ser Pro Val Thr Lys Ser Phe
    195                 200                 205

Asn Arg Gly Glu Cys
    210
```

COMPOUNDS AND THERAPEUTICS USES THEREOF

CROSS-REFERENCE TO RELATED APPLICATIONS

The present application is a U.S. National Stage entry under 35 U.S.C. § 371 of International Application No. PCT/GB2018/050928 filed on Apr. 6, 2018, designating the United States of America and published in English on Nov. 10, 2018, which is hereby incorporated by reference in its entirety.

FIELD OF THE INVENTION

The invention relates to novel compounds with the ability to link an immune response to a defined therapeutic target, to the use of said compounds in treating cancer and infectious diseases, to compositions containing said compounds, processes for their preparation and to novel intermediates used in said process.

REFERENCE TO A SEQUENCE LISTING SUBMITTED ON COMPUTER

The content of ASCII text file of the sequence listing named "2019-10-03-Sequence_Listing-SGTRS-017US0.txt" which was filed in PCT/GB2018/050928 on Apr. 6, 2018, downloaded from the WIPO database, is 12 kb in size with a created date of Oct. 3, 2019, and electronically submitted via EFS-Web herewith the application, is incorporated herein by reference in its entirety.

BACKGROUND OF THE INVENTION

There is a need to find novel ways to recruit an individual's immune system to fight disease. The human immune system continually surveys the body seeking foreign signals to identify potentially harmful pathogens or mutated human cells (that could become a cause of cancerous growth) and targets them for elimination. Natural antibodies exist that can be recruited to said pathogens or mutated human cells to drive the immune system to eliminate the threat.

Cancer is a group of diseases involving abnormal cell growth with the potential to invade or spread to other parts of the body. In 2012, cancer occurred in about 14.1 million people. It caused about 8.2 million deaths or 14.6% of all human deaths. The most common types of cancer in males are lung cancer, prostate cancer, colorectal cancer and stomach cancer. In females the most common types are breast cancer, colorectal cancer, lung cancer, and cervical cancer. It is well established that the immune response plays a vital role in the identification and elimination of cancerous cells. Drugs exist that fight cancer by boosting an individual's immune system to help fight the cancer. There is a need to be able to better target the immune response specifically to the cancer cell and to generate a broader range of the patient's own tumour associated antigens. Targeting pre-existing natural antibodies to the patient's own tumour could meet this need. There is an urgent need to identify novel ways of treating bacterial, viral and fungal infections. Antimicrobial drug resistance is becoming a major global health threat. For example, it is estimated that more than 2 million people in the US are infected with bacteria resistant to one class of antibiotics every year (Centers for Disease Control and Prevention, 2013).

An innovative approach to the treatment of infectious disease or cancer was disclosed in WO 2005/079423 which describes an immunity linker which contains two binding moieties. The first binding moiety is capable of binding to an immune response component of an individual. The second binding moiety is capable of binding to any compound or foreign material such as antigens, pathogens, chemicals, or endogenous materials such as altered cells found in cancer. The resultant effect of said immunity linker molecule is that the pre-existing immune response of the individual is diverted towards the target, i.e. the cancer cell or specific pathogen. Examples of said first binding moieties include compounds or agents which are recognised by the immune system of said individual as foreign and which would therefore trigger an immune response.

Typical examples of first binding moieties include the small molecule hapten dinitrophenyl (DNP), rhamnose or β-1,6-glucan. A further example of a first binding moiety is a carbohydrate molecule capable of binding to a human serum antibody anti-alpha-galactosyl (i.e. galactosyl-alpha-1,3-galactosyl-beta-1,4-N-acetylglucosamine;

Since immune functions depend on multivalency, anti-Gal recruitment will depend not only on the concentration of anti-Gal, but also the affinity of antibody for the target.

Examples of said second binding moieties include antibodies or fragments thereof that bind to a specific target molecule. Further examples of said second binding moieties include established therapeutic antibodies or functional fragments thereof. Cells or pathogens targeted in this manner can be recognised by the immune system as foreign and marked for destruction. Thus, natural antibodies can be mobilised to these tumour cells or pathogens and harness the immune system to eliminate the threat.

WO 98/34957 describes the stimulation of an immune response using antibodies labeled with the alpha-galactosyl epitope. This document describes embodiments in which the stimulation of the immune system relies on the incorporation of alpha-galactosyl epitopes into engineered glycosylation sites within the antibody's constant region. Production of the suitably engineered antibody in cells lines which express alpha-1,3-galactosyl transferase has been reported to result in addition of alpha-galactosyl epitopes. In this case, the number of epitopes incorporated depended on the number of residues engineered for glycosylation. A disadvantage of this approach is the limitation in the number of alpha-galactosyl residues that can be introduced (limited by the number of site specific amino acid modifications). A further disadvantage of the approach is that alpha-1,3-galactosyltransferase delivers a population of carbohydrate derivatives which may not be optimal for anti-galactosyl antibody recruitment, further limiting the number of immune recruiting epitopes. There is therefore a need for linker molecules that enable optimised loading and presentation of alpha-galactosyl epitopes relative to the antibody moiety, to maximise the immune response.

There is therefore a great need for linker molecules which contain spacer groups which have been optimised to control the number and position of first binding moieties (i.e. the carbohydrate molecule capable of binding to a human anti-alpha-galactosyl antibody) relative to the position of the second binding moiety (i.e. the antibody or antigen binding fragment). Such linker molecules are designed to attract natural antibodies in such a way as to be able to optimise the efficacy of immune recruitment while minimising potential side effects and therefore have great utility in the provision of effective anti-cancer therapies and therapies against infective agents.

SUMMARY OF THE INVENTION

According to a first aspect of the invention, there is provided an immunoconjugate comprising an antibody or antigen binding fragment thereof joined via a linker to a carbohydrate molecule capable of binding to a human anti-alpha-galactosyl antibody, characterised in that said linker comprises at least one phenyl ring capable of displaying one or more carbohydrate epitopes capable of binding to a human anti-alpha-galactosyl antibody.

According to a second aspect of the invention, there is provided an immunoconjugate which is a compound of formula (A) or a pharmaceutically acceptable salt thereof:

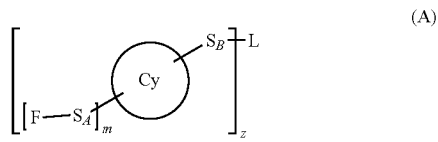

(A)

wherein F is a carbohydrate molecule capable of binding to a human anti-alpha-galactosyl antibody; Cy is phenyl, biphenyl or triphenyl; $S_A$ and $S_B$ are representative of chosen spacers for optimal distance of F and L; m represents an integer selected from 1 to 5; z represents an integer selected from 1 to 30; and L is an antibody or antigen binding fragment thereof.

According to a further aspect of the invention, there is provided a compound of formula (I) or a pharmaceutically acceptable salt thereof:

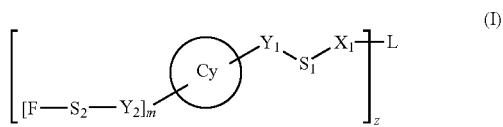

(I)

wherein L represents a binding moiety selected from an antibody or antigen binding fragment thereof;
$S_1$ represents a spacer selected from a —$(CH_2)_a$— or —$(CH_2)_b$—$(CH_2$—$CH_2$—$O)_c$—$(CH_2)_d$— group, wherein one to ten of said —$CH_2$— groups may optionally be substituted by one or more groups selected from —O—, —S—, =N(H)—, —C(=O)—, —C(O)NH—, —NHC(O)—, cyclohexyl or pyrrolidine-2,5-dione;
a represents an integer selected from 1 to 35;
b represents an integer selected from 0 to 5;
c represents an integer selected from 1 to 20;
d represents an integer selected from 1 to 20;
$S_2$ represents a spacer selected from a —$(CH_2)_e$— or —$(CH_2)_f$—$(CH_2$—$CH_2$—$O)_g$—$(CH_2)_h$— group, wherein one to three of said —$CH_2$— groups may optionally be substituted by one or more groups selected from —N(H)—, —C(O)NH— and —NHC(O)—;
e represents an integer selected from 1 to 15;
f represents an integer selected from 1 to 10;
g represents an integer selected from 1 to 20;
h represents an integer selected from 1 to 5;
z represents an integer selected from 1 to 30;
$X_1$ represents an antibody or antigen binding fragment attachment moiety;
$Y_1$ and $Y_2$ independently represent a bond, —O—, —S—, —NH—, —NHC(O)—, —C(O)NH—, —OC(O)—, —C(O)O—, —SC(O)—, —C(O)S—, —NHSO_2—, —SO_2NH— or —NHC(O)NH— group;
F represents a carbohydrate molecule capable of binding to a human anti-alpha-galactosyl antibody;
m represents an integer selected from 1 to 5; and
Cy represents phenyl, biphenyl, triphenyl, such that when Cy represents biphenyl or triphenyl said —$Y_1$—$S_1$—$X_1$-L group may be present on any of said phenyl rings and said [F—$S_2$—$Y_2$]$_m$— group or groups may be present on any of said phenyl rings.

BRIEF DESCRIPTION OF THE FIGURES

FIG. 7: is a dose titration for the compounds of Examples 18 to 21 (FIG. 7A) and 22 to 23 (FIG. 7B) recruiting hIVIG anti-alpha-galactosyl IgG to A431 cells.
FIG. 8: is a dose titration for the compounds of Examples 9 to 11 and 16 (FIG. 8A), Examples 18 to 21 (FIG. 8B), Examples 12 to 15 (FIG. 8C), Examples 22 and 23 (FIG. 8D) and Examples 17 and 24 (FIG. 8E) recruiting anti-galactosyl M86 IgM antibodies to A431 cells.
FIG. 9: C3b deposition data for the compounds of Examples 13 to 15 and 20 (FIG. 9A), Examples 16 and 23 ((FIG. 9B), Examples 22 and 23 (FIG. 9C) and Examples 17 and 24 (FIG. 9D) on A431 cells with 20% Human Serum (HS) or Heat Inactivated Human Serum (HI HS)+25 µg/ml M86 IgM.
FIG. 15: Reducing SDS-PAGE (FIG. 15A) and SEC analysis for rituximab and rituximab-Fab conjugates (Examples 25 (FIG. 15B) and 26 (FIG. 15C)).
FIG. 17: SDS-PAGE (FIG. 17A) and SEC Analysis of rituximab (FIG. 17B) and SEC Analysis of rituximab-Fab (FIG. 17C).

DETAILED DESCRIPTION OF THE INVENTION

Figure 1:
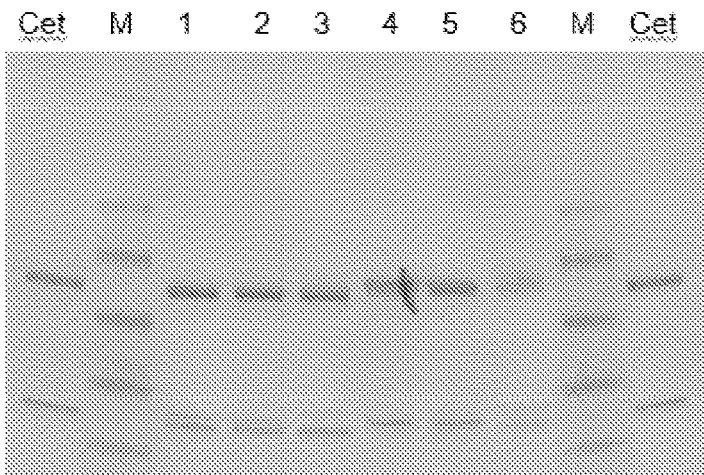
FIG. 1: Reducing SDS page analysis of Examples 1-4.
Figure 2:
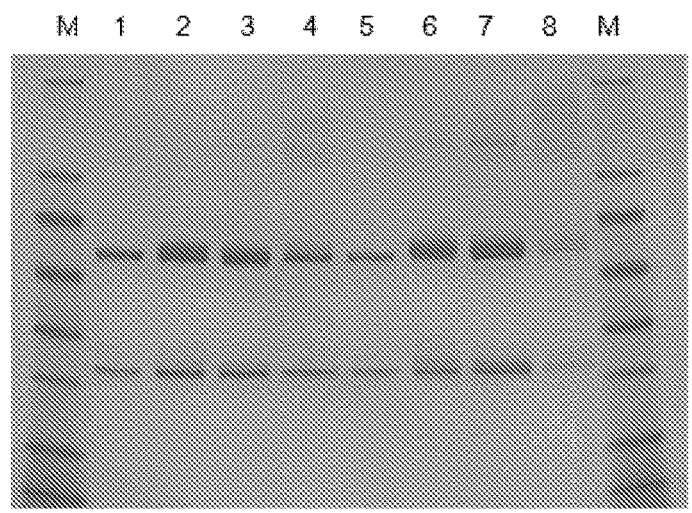
FIG. 2: Reducing SDS page analysis of Examples 5-8.
Figure 3:
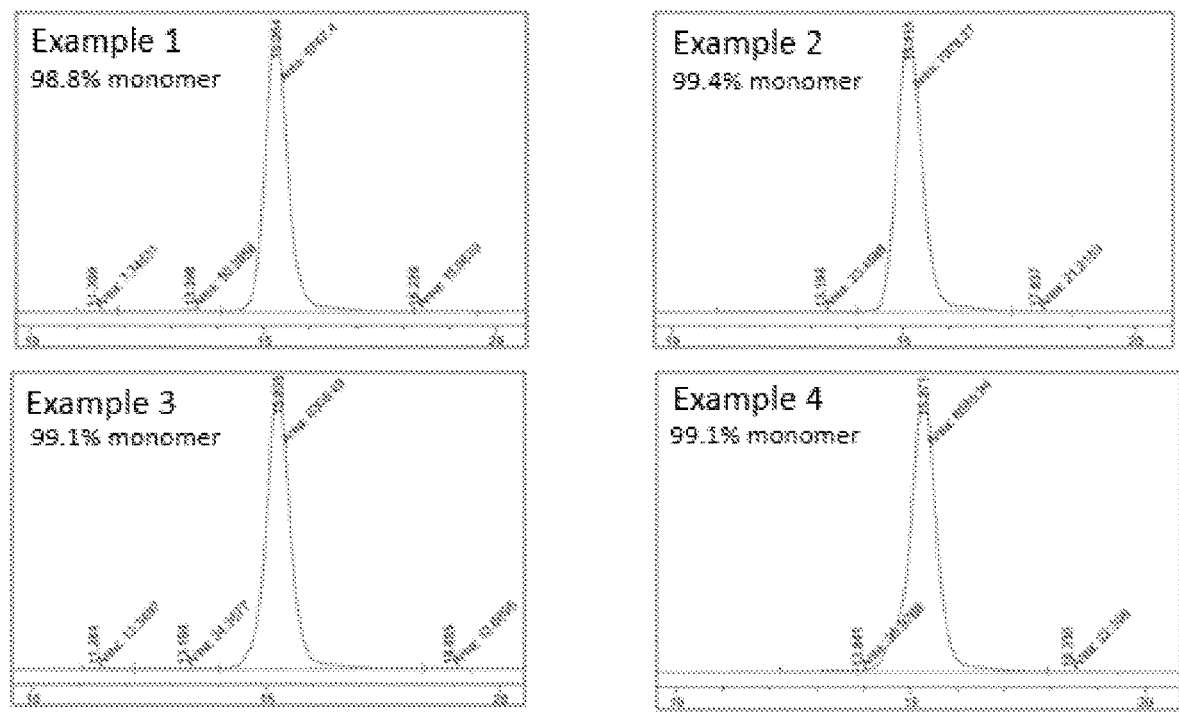
FIG. 3: Analysis of monomer content: SEC for Examples 1-8.

According to a first aspect of the invention, there is provided an immunoconjugate comprising an antibody or antigen binding fragment thereof joined via a linker to a carbohydrate molecule capable of binding to a human anti-alpha-galactosyl antibody, characterised in that said linker comprises at least one phenyl ring capable of displaying one or more carbohydrate epitopes capable of binding to a human anti-alpha-galactosyl antibody.

In one embodiment of the first aspect of the invention, said linker comprises a phenyl, biphenyl or triphenyl group. In a further embodiment of the first aspect of the invention, said linker comprises a biphenyl group.

According to a second aspect of the invention, there is provided an immunoconjugate which is a compound of formula (A) or a pharmaceutically acceptable salt thereof:

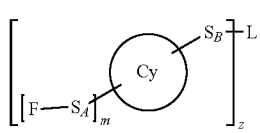
(A)

wherein F is a carbohydrate molecule capable of binding to a human anti-alpha-galactosyl antibody; Cy is phenyl, biphenyl or triphenyl; $S_A$ and $S_B$ are representative of chosen spacers for optimal distance of F and L; m represents an integer selected from 1 to 5; z represents an integer selected from 1 to 30; and L is an antibody or antigen binding fragment thereof.

According to a second aspect of the invention which may be mentioned, there is provided an immunoconjugate which is a compound of formula (A) or a pharmaceutically acceptable salt thereof:

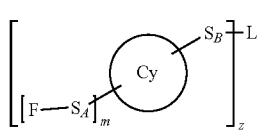
(A)

wherein F is a carbohydrate molecule capable of binding to a human anti-alpha-galactosyl antibody; Cy is phenyl, biphenyl or triphenyl; $S_A$ and $S_B$ are representative of chosen spacers for optimal distance of F and L; m represents an integer selected from 1 to 5; z represents an integer selected from 1 to 10; and L is an antibody or antigen binding fragment thereof.

According to a further aspect of the invention, there is provided a compound of formula (I) or a pharmaceutically acceptable salt thereof:

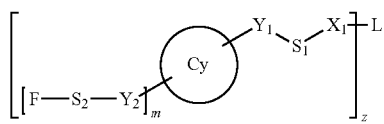
(I)

wherein L represents a binding moiety selected from an antibody or antigen binding fragment thereof;
$S_1$ represents a spacer selected from a —$(CH_2)_a$— or —$(CH_2)_b$—$(CH_2$—$CH_2$—$O)_c$—$(CH_2)_d$— group, wherein one to ten of said —$CH_2$— groups may optionally be substituted by one or more groups selected from —O—, —S—, =N(H)—, —C(=O)—, —C(O)NH—, —NHC(O)—, cyclohexyl or pyrrolidine-2,5-dione;

a represents an integer selected from 1 to 35;
b represents an integer selected from 0 to 5;
c represents an integer selected from 1 to 20;
d represents an integer selected from 1 to 20;
$S_2$ represents a spacer selected from a —$(CH_2)_e$— or —$(CH_2)_f$—$(CH_2$—$CH_2$—$O)_g$—$(CH_2)_h$— group, wherein one to three of said —$CH_2$— groups may optionally be substituted by one or more groups selected from —N(H)—, —C(O)NH— and —NHC(O)—;
e represents an integer selected from 1 to 15;
f represents an integer selected from 1 to 10;
g represents an integer selected from 1 to 20;
h represents an integer selected from 1 to 5;
z represents an integer selected from 1 to 30;
$X_1$ represents an antibody or antigen binding fragment attachment moiety;
$Y_1$ and $Y_2$ independently represent a bond, —O—, —S—, —NH—, —NHC(O)—, —C(O)NH—, —OC(O)—, —C(O)O—, —SC(O)—, —C(O)S—, —NHSO$_2$—, —SO$_2$NH— or —NHC(O)NH— group; F represents a carbohydrate molecule capable of binding to a human anti-alpha-galactosyl antibody;
m represents an integer selected from 1 to 5; and
Cy represents phenyl, biphenyl, triphenyl, such that when Cy represents biphenyl or triphenyl said —$Y_1$—$S_1$—$X_1$-L group may be present on any of said phenyl rings and said $[F$—$S_2$—$Y_2]_m$— group or groups may be present on any of said phenyl rings.

According to a further aspect of the invention which may be mentioned, there is provided a compound of formula (I) or a pharmaceutically acceptable salt thereof:

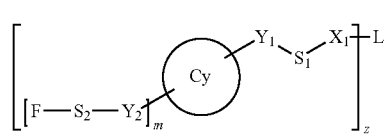
(I)

wherein L represents a binding moiety selected from an antibody or antigen binding fragment thereof;
$S_1$ represents a spacer selected from a —$(CH_2)_a$— or —$(CH_2)_b$—$(CH_2$—$CH_2$—$O)_c$—$(CH_2)_d$— group, wherein one to ten of said —$CH_2$— groups may optionally be substituted by one or more groups selected from —O—, —S—, =N(H)—, —C(O)NH—, —NHC(O)—, cyclohexyl or pyrrolidine-2,5-dione;
a represents an integer selected from 1 to 35;
b represents an integer selected from 0 to 5;
c represents an integer selected from 1 to 20;
d represents an integer selected from 1 to 20;
$S_2$ represents a spacer selected from a —$(CH_2)_e$— or —$(CH_2)_f$—$(CH_2$—$CH_2$—$O)_g$—$(CH_2)_h$— group, wherein one to three of said —$CH_2$— groups may optionally be substituted by one or more groups selected from —N(H)—, —C(O)NH— and —NHC(O)—;
e represents an integer selected from 1 to 15;
f represents an integer selected from 1 to 10;
g represents an integer selected from 1 to 20;
h represents an integer selected from 1 to 5;
z represents an integer selected from 1 to 10;
$X_1$ represents an antibody or antigen binding fragment attachment moiety;
$Y_1$ and $Y_2$ independently represent a bond, —O—, —S—, —NH—, —NHC(O)—, —C(O)NH—, —OC(O)—, —C(O)O—, —SC(O)—, —C(O)S—, —NHSO$_2$—, —SO$_2$NH— or —NHC(O)NH— group;

F represents a carbohydrate molecule capable of binding to a human anti-alpha-galactosyl antibody;

m represents an integer selected from 1 to 5; and

Cy represents phenyl, biphenyl, triphenyl, such that when Cy represents biphenyl or triphenyl said —Y$_1$—S$_1$—X$_1$-L group may be present on any of said phenyl rings and said [F—S$_2$—Y$_2$]$_m$— group or groups may be present on any of said phenyl rings.

The invention includes the description and use of novel immunoconjugate linkers that enable capability to display one or multiple epitopes of carbohydrates in addition to conjugation to single or multiple sites on a chosen antibody or fragment thereof, thus enabling the optimal recruitment of natural antibodies concomitant with retaining target binding efficacy. The invention provides for one skilled in the art to fine tune the optimal number of carbohydrates per chosen antibody or fragment thereof for optimal anti-Gal recruitment and retain target efficacy.

Monoclonal antibodies have greatly improved the outcome of patients suffering from cancer however certain patient populations demonstrate intrinsic resistance to these therapies and, while good outcomes can be observed, these may be short-lived and acquired resistance to mAb therapy remains an issue and increased antibody efficacy is desirable. Tumours can demonstrate or evolve mechanisms resulting in resistance or reduced response to antibody treatment such as through increased receptor expression or changes to the signalling pathway or reduced immune response (Reslan, L. Mabs 2009, 3, 222). For example, patients can show intrinsic resistance to cetuximab resulting from expression of the KRAS mutation which affects EGFR signalling (Lievre, A, J. Clin. Oncol. 2008, 26, 374). In addition, where patients initially respond well to cetuximab, the majority will eventually acquire resistance (Bianco, R. Endocr. Relat. Cancer 2005, S159; Brand, T M. Cancer Biol. Ther. 2011, 11, 777).

A further example of resistance to a therapeutic antibody is seen in the case of non-Hodgkin lymphoma patients treated with rituximab (an anti-CD20 monoclonal antibody). Resistance to Rituximab is observed in around half of treatment-naïve patients. Patients who show an initial response to rituximab therapy will frequently acquire resistance. Resistance mechanisms are complex and strategies to overcome resistance have shown limited success in patients (Best Pract. Res. Clin. Haematol. 2011, 203-216) thus there remains a compelling need to improve the activity of therapeutic antibodies to increase and prolong patient responses.

Many approaches have been adopted to improve upon the efficacy of therapeutic antibodies including antibody drug conjugates (ADCs), antibody toxin conjugates (immunotoxins) and engineered antibodies with enhanced effector mechanisms e.g. increased antibody dependent cellular cytotoxicity (ADCC). Despite these efforts, few therapies have achieved clinical success with side effects such as toxicity remaining a key issue (Beck, A. Nat. Rev. Drug. Discov. 2017), Thus there is a need for new strategies to modify mAbs to enhance efficacy, to improve patient outcomes.

The α-Gal epitope (Galα1,3Galα1,4GlcNAc-R) is a unique carbohydrate, naturally produced on glycolipids and glycoproteins to display multiple epitopes on branched oligosaccharides (J. Immunology (2007), 178 (7), 4676-87). The alpha-Gal epitope is synthesised, for example, by the transferase alpha1-,3-GT, an enzyme well known to catalyse the synthesis of Galα-1,3-Gal on multiple glycosylation sites (WO 98/34957). Although this method is efficient, the synthesis is reliant on existing or engineered glycosylation sites, and only enables one alpha-Gal unit per conjugation site.

There is therefore an attractive need for a suitable modular approach to either one or multi-presentation of alpha-Gal trisaccharide units to optimally harness the natural immune system.

The compounds of the present invention comprise linker molecules which have been optimised to control and display the number and position of F groups (i.e. the carbohydrate molecule capable of binding to a human anti-alpha-galactosyl antibody) relative to the position of the binding moiety L (i.e. the antibody or fragment thereof). For example, a rigid cyclic group has the advantage of providing a scaffold for the optimal positioning of one or more F groups relative to L. It will be appreciated that the exact number and orientation of F groups relative to L will vary depending on the nature of the L group. Furthermore, the presence of the cyclic group, which contains a single phenyl ring, a biphenyl ring or a triphenyl ring provides the significant advantage of presenting multiple F groups (i.e. the carbohydrate molecule capable of binding to a human anti-alpha-galactosyl antibody) to enhance the resultant immune response from the host. Chemical presentation of multiple binding groups was previously known in the art, however, this has been achieved using one or more amino acid groups (for example see WO 2014/178878) or branching linker groups (for example see US 2014/0112975) by contrast to the present invention which uses either a single 6 membered ring system (i.e. phenyl), two 6 membered ring systems joined by a bond (biphenyl) or three membered ring systems joined by 2 bonds (triphenyl). The technical effect of this distinction is that the compounds of the present invention may be prepared more easily than the linkers previously known in art, advantageously avoid the presence of chiral centres and are less liable to protease degradation. Synthesis of the compounds of the present invention also do not make use of resins and therefore provide the advantage of being suitable for scaling for large scale pharmaceutical manufacture. Therefore, the compounds of the invention are not only therapeutically effective but provide the advantage of enhancing the immune response from the host and ease and efficiency of synthesis in high yields with scalability. In addition, the linkers of the present invention are not labile, therefore, do not typically comprise "cleavable linker" components as required by many compounds previously known in the art (see U.S. Pat. No. 8,828,956 for example). Furthermore, the linkers of the present invention allowed the person skilled in the art to choose specific left and right hand combinations of groups with synthetic ease and efficiency to enable the optimal number of F groups per antibody or fragment thereof conjugation site.

Monoclonal antibody fragments such as Fab, Fab', Fab'2, $Fab_2$, Fabs, $F(ab)_2$, Fv, scFv, diabody, triabody, tetrabody, nanobody are also known in the field of oncology. A number of advantages over full length mAbs have been reported; including increased tumour penetration resulting from their smaller size, easier production (they can be expressed in *E. coli* or yeast resulting in increased convenience and more efficient scale up) and reduced immunogenicity. Fragments such as scFvs or Fab fragments can however suffer from reduced efficacy when compared to full length mAbs. For example, the lack of an Fc domain on a Fab fragment eliminates the potential for ADCC driven efficacy, often a component of the anti-tumour response (Nelson, A. L. mAbs 2009, 2, 77).

Thus the benefits of antibody fragments are often offset by the loss of function associated with them. The use of the phenyl containing linkers of the invention to provide new constructs where an optimal number of alpha-Gal moieties are conjugated to an antibody fragment provides a new approach to enhancing the anti-tumour effects of an antibody fragment.

For both mAbs and their fragments, controlled, site specific conjugation is well known in the art e.g. through the incorporation of additional cysteine residues. Such an approach offers several advantages, in particular by allowing derivatisation of the mAb or fragment without disruption of the target binding epitopes and by enabling the loading to be controlled i.e. a fixed stoichoimetry is achieved (Shen, B. Q. Nat. Biotechnol. 2012, 30, 184). One limitation of site specific conjugation is that a low loading of the conjugated moiety may result which can limit efficacy. Use of the phenyl containing linkers of the invention that enable the presentation of multiple alpha-Gal moieties per conjugation site provides a method to achieve high alpha-Gal/antibody ratios (high loading) even when the number of conjugation sites is low.

Linker Definitions

In one embodiment, $S_1$ represents a spacer selected from:
—$(CH_2)_a$—, wherein one to five (such as 2, 3 or 5) of said —$CH_2$— groups may optionally be substituted by one or more groups selected from —S—, =N(H)—, —C(=O)—, —NHC(O)—, cyclohexyl or pyrrolidine-2,5-dione (such as —$(CH_2)_2$—NHCO-cyclohexyl-$CH_2$-3-pyrrolidine-2,5-dione-, —$(CH_2)_2$—NHCO-cyclohexyl-$CH_2$-3-pyrrolidine-2,5-dione-S—$(CH_2)_3$—C(=NH)— or —$(CH_2)_2$—NHCO—$(CH_2)_3$—CO—); or —$(CH_2)_b$—$(CH_2$—$CH_2$—$O)_c$—$(CH_2)_d$—, wherein one to five (such as 2) of said —$CH_2$— groups may optionally be substituted by one or more groups selected from —NHC(O)— or pyrrolidine-2,5-dione (such as —$(CH_2)_2$—NHCO—$(CH_2CH_2O)_4$—$(CH_2)_2$-3-pyrrolidine-2,5-dione-).

In a further embodiment, $S_1$ represents a spacer selected from:
—$(CH_2)_a$—, wherein one to ten of said —$CH_2$— groups may optionally be substituted by one or more groups selected from —O—, —S—, =N(H)—, —C(O)NH—, —NHC(O)—, cyclohexyl or pyrrolidine-2,5-dione (such as —$(CH_2)_2$—NHCO-cyclohexyl-$CH_2$-pyrrolidine-2,5-dione- or —$(CH_2)_2$—NHCO-cyclohexyl-$CH_2$-pyrrolidine-2,5-dione-S—$(CH_2)_3$—C(=NH)—).

It will be appreciated that a, b, c, d, e, f, g and h are selected to maintain a suitable linker length between groups F and L. Examples of suitable linker lengths between F and L range from about 5 Å to about 50 Å or more in length, about 6 Å to about 45 Å, about 7 Å to about 40 Å, about 8 Å to about 35 Å, about 9 Å to about 30 Å, about 10 Å to about 25 Å, about 11 Å to about 20 Å, about 12 Å to about 15 Å. Thus, in one embodiment, a, b, c, d, e, f, g and h represent a total integer of no more than 45, such as between 5 and 45, such as between 7 and 42, such as no more than 30, such as between 5 and 30, such as between 7 and 29.

In one embodiment, a represents an integer selected from 1 to 30. In a further embodiment, a represents an integer selected from 2 to 30. In a further embodiment, a represents an integer selected from 2, 4, 6, 9, 11, 18 or 30. In a further embodiment, a represents an integer selected from 6 to 30. In a further embodiment, a represents an integer selected from 6, 11, 18 or 30. In a further embodiment, a represents an integer selected from 5 to 15. In a further embodiment, a represents an integer selected from 6 to 11. In a further embodiment, a represents an integer selected from 6, 7 or 11.

In a yet further embodiment, a represents an integer selected from 6. In an alternative embodiment, a represents an integer selected from 7. In an alternative embodiment, a represents an integer selected from 11.

In one embodiment, b represents an integer selected from 0 to 3. In a further embodiment, b represents an integer selected from 0 or 3. In a further embodiment, b represents an integer selected from 1 to 3. In a further embodiment, b represents an integer selected from 2 or 3. In a yet further embodiment, b represents an integer selected from 3.

In one embodiment, c represents an integer selected from 1 to 15. In a further embodiment, c represents an integer selected from 1 to 12. In a further embodiment, c represents an integer selected from 4 to 12. In a yet further embodiment, c represents an integer selected from 4 or 12. In a yet further embodiment, c represents an integer selected from 4.

In one embodiment, d represents an integer selected from 1 to 15. In a further embodiment, d represents an integer selected from 2 to 13. In a further embodiment, d represents an integer selected from 2, 5 or 13. In a further embodiment, d represents an integer selected from 13. In an alternative embodiment, d represents an integer selected from 3.

In one embodiment, $Y_1$ represents a bond, —C(O)NH— or —O—. In a further embodiment, $Y_1$ represents —C(O)NH—.

In one embodiment, $S_2$ represents a spacer selected from:
—$(CH_2)_e$—, wherein one or two of said —$CH_2$— groups are optionally substituted by one or two groups selected from —N(H)—, —C(O)NH— and —NHC(O)— (such as —$(CH_2)_3$—NHCO—$CH_2$—, —$(CH_2)_3$—, —$(CH_2)_3$—NHCO—$(CH_2)_4$—CONH—$CH_2$—, —$(CH_2)_3$—NH—$CH_2$— or —$(CH_2)_3$—NHCO—$(CH_2)_3$—NHCO—$CH_2$—); or —$(CH_2)_f$—$(CH_2$—$CH_2$—$O)_g$—$(CH_2)_h$—, wherein one to three of said —$CH_2$— groups are optionally substituted by one to three —NHC(O)— groups (such as —$(CH_2)_3$—NHCO—$(CH_2CH_2O)_4$—$(CH_2)_2$—NHCO—$CH_2$—, —$(CH_2)_3$—NHCO—$(CH_2CH_2O)_{12}$—$(CH_2)_2$—NHCO—$CH_2$— or —$(CH_2)_3$—NHCO—$(CH_2)_3$—NHCO—$(CH_2CH_2O)_4$—$(CH_2)_2$—NHCO—$CH_2$—).

In a further embodiment, $S_2$ represents a spacer selected from —$(CH_2)_e$—, wherein one or two of said —$CH_2$— groups are optionally substituted by a —C(O)NH— or —NHC(O)— group (such as —$(CH_2)_3$—NHCO—$CH_2$—, —$(CH_2)_3$—NHCO—, —$(CH_2)_3$—, —$(CH_2)_3$—NHCO—$(CH_2)_4$—CONH—$CH_2$— or —$(CH_2)_3$—NH—$CH_2$—) or —$(CH_2)_f$—$(CH_2$—$CH_2$—$O)_g$—$(CH_2)_h$—, wherein one or two of said —$CH_2$— groups are optionally substituted by a —C(O)NH— or —NHC(O)— group (such as —$(CH_2)_3$—NHCO—$(CH_2)_2$—$(OCH_2CH_2)_4$—NHCO—$CH_2$— or —$(CH_2)_4$—NHCO—$(CH_2)_2$—$(OCH_2CH_2)_4$—NHCO—$CH_2$—).

In a yet further embodiment, $S_2$ represents a spacer selected from:
—$(CH_2)_e$—, wherein one or two of said —$CH_2$— groups are optionally substituted by one or two —NHC(O)— groups (such as —$(CH_2)_3$—NHCO—$CH_2$— or —$(CH_2)_3$—NHCO—$(CH_2)_3$—NHCO—$CH_2$—); or
—$(CH_2)_f$—$(CH_2$—$CH_2$—$O)_g$—$(CH_2)_h$—, wherein one to three of said —$CH_2$— groups are optionally substituted by one to three —NHC(O)— groups (such as —$(CH_2)_3$—NHCO—$(CH_2CH_2O)_4$—$(CH_2)_2$—NHCO—$CH_2$—, —$(CH_2)_3$—NHCO—$(CH_2CH_2O)_{12}$—$(CH_2)_2$—NHCO—$CH_2$— or —$(CH_2)_3$—NHCO—$(CH_2)_3$—NHCO—$(CH_2CH_2O)_4$—$(CH_2)_2$—NHCO—$CH_2$—).

In a still yet further embodiment, $S_2$ represents a spacer selected from:
- —$(CH_2)_e$—, wherein one or two of said —$CH_2$— groups are optionally substituted by one or two groups selected from —N(H)—, —C(O)NH— and —NHC(O)— (such as —$(CH_2)_3$—NHCO—$CH_2$—); or
- —$(CH_2)_f$—$(CH_2$—$CH_2$—O$)_g$—$(CH_2)_h$—, wherein one to three of said —$CH_2$— groups are optionally substituted by one to three —NHC(O)— groups (such as —$(CH_2)_3$—NHCO—$(CH_2CH_2O)_4$—$(CH_2)_2$—NHCO—$CH_2$—.

In a still yet further embodiment, $S_2$ represents a spacer selected from:
- —$(CH_2)_e$—, wherein one or two, such as one, of said —$CH_2$— groups are optionally substituted by one or two, such as one, groups selected from —N(H)—, —C(O)NH— and —NHC(O)— (such as —$(CH_2)_3$—NHCO—$CH_2$—).

In a still yet further embodiment, $S_2$ represents a spacer selected from:
- —$(CH_2)_f$—, wherein one of said —$CH_2$— groups is optionally substituted by a —NHC(O)— group (such as —$(CH_2)_3$—NHCO—$CH_2$—); or
- —$(CH_2)_f$—$(CH_2$—$CH_2$—O$)_g$—$(CH_2)_h$—, wherein two of said —$CH_2$— groups are optionally substituted by an —NHC(O)— group (such as —$(CH_2)_3$—NHCO—$(CH_2CH_2O)_4$—$(CH_2)_2$—NHCO—$CH_2$—).

In one embodiment, e represents an integer selected from 1 to 10. In a further embodiment, e represents an integer selected from 3 to 10. In a further embodiment, e represents an integer selected from 3, 5, 9 or 10. In a further embodiment, e represents an integer selected from 5 to 9. In a further embodiment, e represents an integer selected from 5 or 9. In a further embodiment, e represents an integer selected from 4 to 10. In a yet further embodiment, e represents an integer selected from 4, 5 or 10. In a still yet further embodiment, e represents an integer selected from 5.

In one embodiment, f represents an integer selected from 1 to 8. In a further embodiment, f represents an integer selected from 2 to 8. In a further embodiment, f represents an integer selected from 2 to 6. In a yet further embodiment, f represents an integer selected from 4 to 8. In a yet further embodiment, f represents an integer selected from 4 or 8. In a still yet further embodiment, f represents an integer selected from 4.

In one embodiment, g represents an integer selected from 1 to 15. In a further embodiment, g represents an integer selected from 4 to 12. In a further embodiment, g represents an integer selected from 4 or 12. In a further embodiment, g represents an integer selected from 1 to 5. In a further embodiment, g represents an integer selected from 1 to 4. In a yet further embodiment, g represents an integer selected from 4.

In one embodiment, h represents an integer selected from 1 to 4. In a further embodiment, h represents an integer selected from 4.

In one embodiment, $Y_2$ represents a bond, —O— or —NHC(O)—. In a further embodiment, $Y_2$ represents a bond or —O—. In a yet further embodiment, $Y_2$ represents —O—.

In one embodiment, m represents an integer selected from 1 to 4. In a further embodiment, m represents an integer selected from 1 to 3. In a yet further embodiment, m represents an integer selected from 1 or 3. In a further embodiment, m represents an integer selected from 2 or 3. In a yet further embodiment, m represents an integer selected from 1 or 2. In a yet further embodiment, m represents an integer selected from 1. In a yet further embodiment, m represents an integer selected from 2. In a yet further embodiment, m represents an integer selected from 3. In a yet further embodiment, m represents an integer selected from 4.

In a further embodiment, z represents an integer selected from 1 to 25. In a further embodiment, z represents an integer selected from 1 to 20. In a further embodiment, z represents an integer selected from 2 to 20 (such as 2, 4.9, 5, 7, 8, 10, 11, 14, 15, 17 or 20). In a further embodiment, z represents an integer selected from 1 to 8. In a further embodiment, z represents an integer selected from 1 to 5. In a yet further embodiment, z represents an integer selected from 2 to 5. In a yet further embodiment, z represents an integer selected from 2 or 5. In a yet further embodiment, z represents an integer selected from 2. In a yet further embodiment, z represents an integer selected from 5.

In one embodiment, Cy represents phenyl or biphenyl. In a further embodiment, Cy represents biphenyl or triphenyl. In a yet further embodiment, Cy represents phenyl or triphenyl. In a still yet further embodiment, Cy represents biphenyl.

According to a further aspect of the invention, there is provided a compound of formula (I)$^a$ or a pharmaceutically acceptable salt thereof:

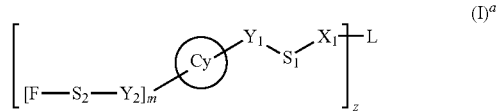

wherein L represents a binding moiety selected from an antibody or antigen binding fragment thereof;
$S_1$ represents a spacer selected from:
- —$(CH_2)_a$—, wherein 2, 3 or 5 of said —$CH_2$— groups may optionally be substituted by one or more groups selected from —S—, =N(H)—, —C(=O)—, —NHC(O)—, cyclohexyl or pyrrolidine-2,5-dione; or
- —$(CH_2)_b$—$(CH_2$—$CH_2$—O$)_c$—$(CH_2)_d$—, wherein two of said —$CH_2$— groups may optionally be substituted by one or more groups selected from —NHC(O)— or pyrrolidine-2,5-dione;

a represents an integer selected from 6, 7 or 11;
b represents an integer selected from 3;
c represents an integer selected from 4;
d represents an integer selected from 3;
$S_2$ represents a spacer selected from:
- —$(CH_2)_e$—, wherein one of said —$CH_2$— groups is optionally substituted by a —NHC(O)— group; or
- —$(CH_2)_f$—$(CH_2$—$CH_2$—O$)_g$—$(CH_2)_h$—, wherein two of said —$CH_2$— groups are optionally substituted by an —NHC(O)— group;

e represents an integer selected from 5;
f represents an integer selected from 4;
g represents an integer selected from 4;
h represents an integer selected from 4;
z represents an integer selected from 2 to 20;
$X_1$ represents —S— or —N(H)—;
$Y_1$ represents —C(O)NH—;
$Y_2$ represents —O—;
F represents a carbohydrate molecule capable of binding to a human anti-alpha-galactosyl antibody;
m represents an integer selected from 1 or 3; and Cy represents biphenyl, such that said —Y$_1$—S$_1$—X$_1$-L group may be present on either of said phenyl rings and said [F—S$_2$—Y$_2$]$_m$— group or groups may be present on either of said phenyl rings.

According to a further aspect of the invention which may be mentioned, there is provided a compound of formula (I)$^a$ or a pharmaceutically acceptable salt thereof:

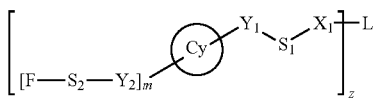
(I)$^a$ wherein L represents a binding moiety selected from an antibody or antigen binding fragment thereof;
S$_1$ represents a spacer selected from a —(CH$_2$)$_a$— group, wherein one to five of said —CH$_2$— groups may optionally be substituted by one or more groups selected from —O—, —S—, =N(H)—, —C(O)NH—, —NHC(O)—, cyclohexyl or pyrrolidine-2,5-dione;
a represents an integer selected from 6 or 11;
S$_2$ represents a spacer selected from a —(CH$_2$)$_e$— group, wherein one to three of said —CH$_2$— groups may optionally be substituted by one or more groups selected from —N(H)—, —C(O)NH— and —NHC(O)—;
e represents an integer selected from 5;
z represents an integer selected from 2 to 5;
X$_1$ represents —S— or —N(H)—;
Y$_1$ represents —C(O)NH—;
Y$_2$ represents —O—;
F represents a carbohydrate molecule capable of binding to a human anti-alpha-galactosyl antibody; and
m represents an integer selected from 1 or 3; and
Cy represents biphenyl, such that said —Y$_1$—S$_1$—X$_1$-L group may be present on either of said phenyl rings and said [F—S$_2$—Y$_2$]$_m$— group or groups may be present on either of said phenyl rings.

In a further embodiment, the invention provides a compound of formula (I) which comprises a compound of Examples 1-26 or a pharmaceutically acceptable salt thereof.

In a further embodiment, the invention provides a compound of formula (I) which is the free base of a compound of Examples 1-26.

In a further embodiment, the invention provides a compound of formula (I) which comprises a compound of Examples 1-8 or a pharmaceutically acceptable salt thereof.

In a further embodiment, the invention provides a compound of formula (I) which is the free base of a compound of Examples 1-8.

Alpha Gal

References herein to the term "carbohydrate molecule capable of binding to a human anti-alpha-galactosyl antibody" include sugar (i.e. carbohydrate) moieties capable of binding to an immune response component (i.e. an anti-alpha-galactosyl antibody) of said human and consequently eliciting an immune response in a human. In one embodiment, said anti-alpha-galactosyl antibody is an anti-alpha-galactosyl IgG antibody or an anti-alpha-galactosyl IgM antibody. Examples of such carbohydrate molecules include alpha-galactosyl compounds and modified derivatives thereof. Further examples of suitable carbohydrate molecules include the alpha-gal epitopes listed in US 2012/0003251 as being suitable for use in the selective targeting and killing of tumour cells, the epitopes of which are herein incorporated by reference. In one embodiment, F is selected from galactosyl-alpha-1,3-galactosyl-beta-1,4-N-acetylglucosamine, alpha1-3 galactobiose, alpha1-3-beta1-4-galactotriose or galilipentasaccharide.

In one particular embodiment, F has a structure as shown in one of the following formulae:

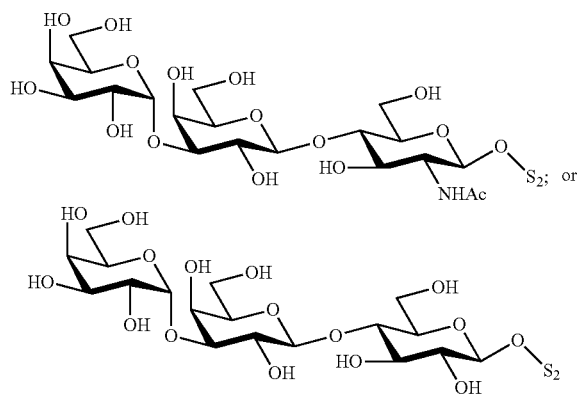

wherein 52 refers to the point of attachment to the 52 group.

In one particular embodiment, F has a structure as shown in the following formula:

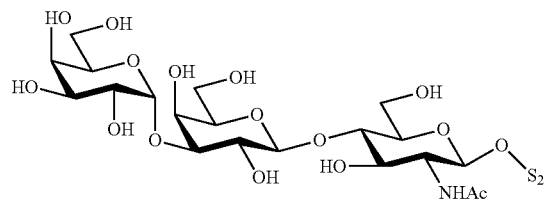

wherein 52 refers to the point of attachment to the 52 group.

Antibodies and Antigen Binding Fragments Thereof

References herein to the terms "antibody" or "antibodies" refer to molecules or active fragments of molecules that bind to known antigens, particularly to immunoglobulin molecules and to immunologically active portions of immunoglobulin molecules, i.e. molecules that contain a binding site that immunospecifically binds an antigen. The immunoglobulin according to the invention can be of any class (IgG, IgM, IgD, IgE, IgA and IgY) or subclass (e.g. IgG1, IgG2, IgG3, IgG4, IgA1 and IgA2) or subclasses (isotypes) of immunoglobulin molecule (e.g. IgG in IgG1, IgG2, IgG3, and IgG4, or IgA in IgA1 and IgA2).

Within the scope of the present invention the terms "antibody" or "antibodies" include monoclonal, polyclonal, chimeric, single chain, bispecific, human and humanized antibodies as well as active fragments thereof. Examples of active fragments of molecules that bind to known antigens include Fab, F(ab')2, scFv and Fv fragments, including the products of an Fab immunoglobulin expression library and epitope-binding fragments of any of the antibodies and fragments mentioned above.

As used herein, the term "monoclonal antibody" refers to an antibody that is mass produced in the laboratory from a single clone and that recognizes only one antigen. Monoclonal antibodies are typically made by fusing a normally short-lived, antibody-producing B cell to a fast-growing cell, such as a cancer cell (sometimes referred to as an "immortal" cell). The resulting hybrid cell, or hybridoma, multiplies rapidly, creating a clone that produces large quantities of the antibody. For the purpose of the present invention, "monoclonal antibody" is also to be understood to comprise antibodies that are produced by a mother clone which has not yet reached full monoclonality.

As used herein, the term "chimeric antibody" refers to a monoclonal antibody comprising a variable region, i.e., binding region, from mouse and at least a portion of a constant region derived from a different source or species, usually prepared by recombinant DNA techniques. Chimeric antibodies comprising a mouse variable region and a human constant region are exemplary embodiments. Such mouse/human chimeric antibodies are the product of expressed immunoglobulin genes comprising DNA segments encoding mouse immunoglobulin variable regions and DNA segments encoding human immunoglobulin constant regions. Other forms of "chimeric antibodies" encompassed by the present disclosure are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now well known in the art. See, e.g., Morrison, S. L., et al., *Proc. Natl. Acad Sci. USA* 81 (1984) 6851-6855; U.S. Pat. Nos. 5,202,238 and 5,204,244.

As used herein the term "humanized antibody" or "humanized version of an antibody" refers to antibodies in which the framework or "complementarity determining regions" (CDR) have been modified to comprise the CDR of an immunoglobulin of different specificity as compared to that of the parent immunoglobulin. In some exemplary embodiments, the CDRs of the VH and VL are grafted into the framework region of human antibody to prepare the "humanized antibody." See e.g. Riechmann, L., et al., *Nature* 332 (1988) 323-327; and Neuberger, M. S., et al., *Nature* 314 (1985) 268-270. The heavy and light chain variable framework regions can be derived from the same or different human antibody sequences. The human antibody sequences can be the sequences of naturally occurring human antibodies. Human heavy and light chain variable framework regions are listed e.g. in Lefranc, M.-P., Current Protocols in Immunology (2000)—Appendix 1P A.1P.1-A.1P.37 and are accessible via IMGT, the international ImMunoGeneTics information System® (http://imgt.cines.fr) or via http://vbase.mrc-cpe.cam.ac.uk, for example. Optionally the framework region can be modified by further mutations. Exemplary CDRs correspond to those representing sequences recognizing the antigens noted above for chimeric antibodies. In some embodiments, such humanized version is chimerized with a human constant region. The term "humanized antibody" as used herein also comprises such antibodies which are modified in the constant region to generate the properties according to the disclosure, especially in regard to C1q binding and/or FcR binding, e.g. by "class switching" i.e. change or mutation of Fc parts (e.g. from IgG1 to IgG4 and/or IgG1/IgG4 mutation).

As used herein the term "human antibody" is intended to include antibodies having variable and constant regions derived from human germ line immunoglobulin sequences. Human antibodies are well-known in the state of the art (van Dijk, M. A., and van de Winkel, J. G., *Curr. Opin. Chem. Biol.* 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germline immunoglobulin gene array in such germ-line mutant mice results in the production of human antibodies upon antigen challenge (see, e.g., Jakobovits, A., et al., *Proc. Natl. Acad. Sci. USA* 90 (1993) 2551-2555; Jakobovits, A., et al., *Nature* 362 (1993) 255-258; Brueggemann, M. D., et al., Year *Immunol.* 7 (1993) 33-40). Human antibodies can also be produced in phage display libraries (Hoogenboom, H. R., and Winter, G., *J. Mol. Biol.* 227 (1992) 381-388; Marks, J. D., et al., *J. Mol. Biol.* 222 (1991) 581-597). The techniques of Cole, A., et al. and Boerner, P., et al. are also available for the preparation of human monoclonal antibodies (Cole, A., et al., Monoclonal Antibodies and Cancer Therapy, Liss, A. R. (1985) p. 77; and Boerner, P., et al., *J. Immunol.* 147 (1991) 86-95). As already mentioned, according to the instant disclosure the term "human antibody" as used herein also comprises such antibodies which are modified in the constant region to generate the properties according to the disclosure, for example in regard to C1q binding and/or FcR binding, e.g. by "class switching" i.e. change or mutation of Fc parts (e.g. from IgG1 to IgG4 and/or IgG1/IgG4 mutation).

As used herein "single chain antibody" refers to single chain Fv molecules (scFv), wherein a VH domain and a VL domain are linked by a peptide linker which allows the two domains to associate to form an antigen binding site (Bird et al., 1988, Science 242:423-426, Huston et al., 1988, *Proc. Natl. Acad. Sci. U.S.A.* 85:5879-5883 or a bispecific single chain Fv (WO 03/11161).

As used herein the term "bispecific antibodies" refers to antibodies that bind to two (or more) different antigens.

As used herein the term "antibody fragments" refers to a portion of a full length antibody, for example possibly a variable domain thereof, or at least an antigen binding site thereof. Examples of antibody fragments include diabodies, single-chain antibody molecules, and multispecific antibodies formed from antibody fragments. scFv antibodies are, e.g., described in Huston, J. S., *Methods in Enzymol.* 203 (1991) 46-88. Antibody fragments can be derived from an antibody of the present invention by a number of art-known techniques. For example, purified monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. et al. *J. Nucl. Med.* 23:1011-1019 (1982); Rousseaux et al. *Methods Enzymology*, 121:663-69, Academic Press, 1986.

As used herein the term "specific" and "specifically" are used interchangeably to indicate that other biomolecules do not significantly bind to the antibody that is specifically binding to the biomolecule of interest. In some embodiments, the level of binding to a biomolecule other than a peptide comprising an epitope within a peptide results in a negligible (e.g., not determinable) binding affinity by means of ELISA or an affinity determination.

By "negligible binding" a binding is meant, which is at least about 85%, particularly at least about 90%, more particularly at least about 95%, even more particularly at least about 98%, but especially at least about 99% and up to 100% less than the binding to a peptide comprising an epitope within a peptide.

As used herein the term "epitope" refers to a site on a target molecule (e.g., an antigen, such as a protein) to which an antigen-binding molecule (e.g., an antibody or antibody fragment) binds. Epitopes can be formed both from contiguous or adjacent noncontiguous residues (e.g., amino acid residues) of the target molecule. Epitopes formed from contiguous residues (e.g., amino acid residues) typically are also called linear epitopes. An epitope typically includes at least 5 and up to about 12 residues, mostly between 6 and 10 residues (e.g. amino acid residues).

As used herein, the term "CDR" refers to the hypervariable region of an antibody. The term "hypervariable region", "HVR", or "HV", when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions are based on sequence variability and are the most commonly used (Kabat et al., Sequences of Proteins of Immunological Interest, 5th Ed. Public Health Service, National Institutes of Health, Bethesda, Md. (1991)). The letters "HC" and "LC" preceding the term "CDR" refer, respectively, to a CDR of a heavy chain and a light chain.

As used herein, the terms "homology" and "identity" are used interchangeably. Calculations of sequence homology or identity between sequences are performed as follows.

In order to determine the percent (%) identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 75%, 80%, 82%, 84%, 85%, 86%, 87%, 88%, 89%, 90%, 91%, 92%, 93%, 94%, 95%, 96%, 97%, 98%, 99%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman et al. (1970) *J. Mol. Biol.* 48:444-453) algorithm which has been incorporated into the GAP program in the GCG software package (available at http://www.gcg.com), using either a BLOSUM 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a BLOSUM 62 scoring matrix with a gap penalty of 12, a gap extend penalty of 4, and a frameshift gap penalty of 5.

Alternatively, the percent identity between two amino acid or nucleotide sequences can be determined using the algorithm of Meyers et al. (1989) *CABIOS* 4:11-17) which has been incorporated into the ALIGN program (version 2.0), using a PAM120 weight residue table, a gap length penalty of 12 and a gap penalty of 4.

As used herein the term "conservative amino acid substitution" refers to replacement of an amino acid residue with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

In one embodiment, the antibody is a polyclonal antibody. In one embodiment, the antibody is a humanized antibody, a human antibody, a murine antibody or a chimeric antibody.

In one embodiment, the antigen binding fragment thereof is an antigen-binding fragment (Fab) or a single-chain variable fragment (scFv). In a further embodiment, said fragment is selected from the group consisting of Fab, Fab', F(ab)2, F(ab')2, and scFv.

It will be appreciated that $X_1$ can represent any suitable antibody or antigen binding fragment attachment moiety and that the choice of said group will depend upon the amino acid residue selected as the attachment point within the antibody.

In one embodiment, $X_1$ represents —S— or —N(H)—. In this embodiment, L is conjugated to compounds of formula (I) according to one of the three following structures:

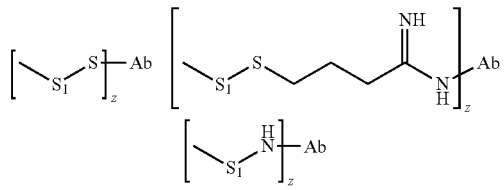

wherein $S_1$ and z are as defined herein and Ab represents an antibody or antigen binding fragment thereof terminated with reactive thiol or lysine groups. Such reacting thiol or cysteine groups may be available on the antibody or antigen binding fragment thereof or they may be introduced through site specific modifications to the peptide chain, to deliver additional points of conjugation via engineered amino acid residues (Nat. Biotechnol. 2008, 925; Nat. Biotechnol. 2012, 184). Alternatively, site specific amino acids may be incorporated into the desired peptide chain to enable orthogonal chemical reactivity for site specific conjugation (OPRD (2016), 20, 852-866). Examples of amino acids with orthogonal reactivity include p-acetylphenylalanine (pAcPhe, J. Mol. Biol. 2011, 595), para-azidomethyl-1-phenylalanine (pAMF, Bioconjug. Chem 2014, 351), N6-((2-azidoethoxy)carbonyl)-L-lysine (Bioconjug. Chem. 2015, 2249).

It will be appreciated that the antibody or antigen binding fragments of the present invention will be configured to bind to a therapeutic target which is either a cancer cell or a specific pathogen.

In one embodiment, the antibody or antigen binding fragments are configured to bind to a cancer cell. In a further embodiment, the antibody or antigen binding fragments specifically bind to a tumour-associated antigen whose cell surface expression on a tumour cell is different to its expression on a healthy cell.

In a preferred embodiment, the antibody or antigen binding fragment binds to a target on a cancer cell or pathogen. Preferred targets include: EGFR, HER2, HER3, CD22, EpCAM, PSMA, PSCA, FLT-3, CD30, CD20, CD33, CD23, CD2, CD37, CD25, CD73, CD47, LGR-5, CD80, CD86, CD70, CD74, CD40, CD19, CD79b, CA-125, c-met, CXCR4, DR5, PD-1, PD1L, LeY, MUC1, MUC2, MUC3, MUC4, MUC5ac, MIP-1A, MIP-1B, KIT, TRAIL receptor (R1 and R2), CXCR4, CEACAM, IGF-1R, carbonic anhydrase IX, PDGFRa, CD137, CD276, mesothelin, VEGFR, P-cadherin, CD56, bacterial Psi, bacterial lipopolysaccharide, galactan-Ill epitope of bacterial LPS, bacterial PcrV, RSV F protein.

Anti-EGFR Antibodies

In a further embodiment, the antibody or antigen binding fragment is an Epidermal Growth Factor Receptor (EGFR) binding epitope. EGFR is well known to be over-expressed in several human cancer types. The high expression on certain cancer cells makes EGFR an attractive target for new therapies. In one embodiment, the EGFR binding antibody or antigen binding fragment is an epitope which binds to any of the EGFR subfamily selected from: EGFR (ErbB-1), HER2/c-neu (ErbB-2), Her 3 (ErbB-3) and Her 4 (ErbB-4). Examples of suitable EGFR binding antibodies include but are not limited to Cetuximab, Nimotuzumab, Matuzumab, Zalutumumab, and Panitumumab.

| Sequence ID NO | Sequence |
| --- | --- |
| Cetuximab Heavy chain (SEQ ID NO: 1) | QVQLKQSGPGLVQPSQSLSITCTVSGFSLTNYGVHWVRQSP GKGLEWLGVIWSGGNTDYN TPFTSRLSINKDNSKSQVFFKMNSLQSNDTAIYYCARALTY YDYEFAYWGQGTLVTVSAA STKGPSVFPLAPSSKSTSGGTAALGCLVKDYFPEPVTVSWN SGALTSGVHTFPAVLQSSG LYSLSSVVTVPSSSLGTQTYICNVNHKPSNTKVDKKVEPKS CDKTHTCPPCPAPELLGGP SVFLFPPKPKDTLMISRTPEVTCVVVDVSHEDPEVKFNWYV DGVEVHNAKTKPREEQYNS TYRVVSVLTVLHQDWLNGKEYKCKVSNKALPAPIEKTISKA KGQPREPQVYTLPPSRDEL TKNQVSLTCLVKGFYPSDIAVEWESNGQPENNYKTTPPVLD SDGSFFLYSKLTVDKSRWQ QGNVFSCSVMHEALHNHYTQKSLSLSPGK |
| Cetuximab Light chain (SEQ ID NO: 2) | DILLTQSPVILSVSPGERVSFSCRASQSIGTNIHWYQQRTN GSPRLLIKYASESISGIPS RFSGSGSGTDFTLSINSVESEDIADYYCQQNNNWPTTFGAG TKLELKRTVAAPSVFIFPP SDEQLKSGTASVVCLLNNFYPREAKVQWKVDNALQSGNSQE SVTEQDSKDSTYSLSSTLT LSKADYEKHKVYACEVTHQGLSSPVTKSFNRGEC |

In a further embodiment, the EGFR antibody is cetuximab, a hybrid mouse/human chimeric antibody comprising both heavy and light chain sequences as disclosed in (a) Li et al. (2005) Cancer Cell 7, 301-11; (b) Dubois et al. (2008) Anal. Chem. 80, 1737-45; and (c) IMGT database available at www.imqt.org; www.drugbank.ca or WO 2016/196682.

In a further embodiment the cetuximab antibody or antigen binding fragment thereof recognises and specifically binds EGFR and has heavy and light chain variable domains having at least 80%, 82%, 84%, 85%, 86%, 87%, 88%, 89%, 90%, 91%, 92%, 93%, 94%, 95%, 96%, 97%, 98%, 99%, or 100% sequence identity to SEQ ID NOS: 1 and 2.

In a further embodiment, fragments of EGFR binding antibodies may be selected as examples of L. Typical examples include but are not limited to cetuximab Fab (Li, S. et al (2005) Cancer Cell 7, 301-311); cetuximab scFv (U.S. Pat. No. 7,060,808); Panitumumab Fab (Sickmier E. A. et al (2016) PLoSOne 11, 9, e0163366); Panitumumab scFv (U.S. Pat. No. 6,235,883) and D2C7 scFv (US 2013/0022598; Clin Cancer Res 2013, 19(17), 4717-4727).

Anti-CD20 Antibodies

In a further embodiment, the antibody or antigen binding fragment is a CD20 binding epitope. Removal of CD20 expressing cells (e.g. B cells), is well known to have therapeutic benefit in the treatment of haematological cancers such as leukemias and lymphomas. Examples of suitable CD20 binding antibodies include but are not limited to rituximab, ocrelizumab, ofatumumab and obinutuzumab.

| | |
| --- | --- |
| Rituximab Heavy chain (SEQ ID NO: 3) | QVQLQQPGAELVKPGASVKMSCKASGYTFTSYNMHWVKQTPGRGLEWIGAIYPG NGDTSY NQKFKGKATLTADKSSSTAYMQLSSLTSEDSAVYYCARSTYYGGDWYFNVWGAG TTVTVS AASTKGPSVFPLAPSSKSTSGGTAALGCLVKDYFPEPVTVSWNSGALTSGVHTF PAVLQS SGLYSLSSVVTVPSSSLGTQTYICNVNHKPSNTKVDKKAEPKSCDKTHTCPPCP APELLG GPSVFLFPPKPKDTLMISRTPEVTCVVVDVSHEDPEVKFNWYVDGVEVHNAKTK PREEQY NSTYRVVSVLTVLHQDWLNGKEYKCKVSNKALPAPIEKTISKAKGQPREPQVYT LPPSRD ELTKNQVSLTCLVKGFYPSDIAVEWESNGQPENNYKTTPPVLDSDGSFFLYSKL TVDKSR WQQGNVFSCSVMHEALHNHYTQKSLSLSPGK |

-continued

| | |
|---|---|
| Rituximab Light chain (SEQ ID NO: 4) | QIVLSQSPAILSASPGEKVTMTCRASSSVSYIHWFQQKPGSSPKPWIYATSNLA SGVPVR FSGSGSGTSYSLTISRVEAEDAATYYCQQWTSNPPTFGGGTKLEIKRTVAAPSV FIFPPS DEQLKSGTASVVCLLNNFYPREAKVQWKVDNALQSGNSQESVTEQDSKDSTYSL SSTLTL SKADYEKHKVYACEVTHQGLSSPVTKSFNRGEC |

In a further embodiment, the CD20 antibody is rituximab, a hybrid mouse/human chimeric antibody comprising both heavy and light chain sequences as disclosed in (a) U.S. Pat. No. 5,736,137, (b) Wang, B. et al (2013) Analyst 138, 3058-3065 and (c) IMGT database available at www.imgt.org; www.drugbank.ca.

In a further embodiment the rituximab antibody or antigen binding fragment thereof recognises and specifically binds CD20 and has heavy and light chain variable domains having at least 80%, 82%, 84%, 85%, 86%, 87%, 88%, 89%, 90%, 91%, 92%, 93%, 94%, 95%, 96%, 97%, 98%, 99%, or 100% sequence identity to SEQ ID NOS: 3 and 4.

In a further embodiment, fragments of CD20 binding antibodies may be selected as examples of L. Typical examples include but are not limited to rituximab Fab (Du, J. et al (2007) *J. Biological Chem.* 282, 15073-15080).

In a further embodiment, the CD20 antibody or fragment thereof is selected from rituximab or rituximab Fab.

Pathogen Specific Antibody Targets

In an alternative embodiment, the antibody or antigen binding fragments are configured to bind to a specific pathogen. In a further embodiment, the antibody or antigen binding fragments are configured to bind *S. aureus* and *Pseudomonas aeruginosa* bacteria. Examples of suitable antibodies include but are not limited to those reported in WO 2015/196011, WO 2012/170807 and WO 2014/074528.

Conjugates

Any antibody or fragment thereof disclosed herein may be conjugated to the cyclic spacer linkers described herein containing one or more alpha-Gal. The invention pertains to the ability to choose the optimal number of alpha-Gal units per linker per conjugation site whilst retaining efficacy of the antibody or fragment thereof. The type of conjugation may be selected by one skilled in the art to enable the highest yield and purity of the isolated material based on the terminal functionality of the linker and the surface reactivity or selected reactive site of the antibody or fragment thereof. In some embodiments conjugation is facilitated by a thiol addition to a maleimide moiety. Alternatively conjugation may be facilitated by the amide bond formation between an amino group and an activated ester such as an NHS ester.

When a conjugate includes several reactive sites leading to multiple conjugation reactions, it is to be understood that the aforementioned ranges may refer to the actual or average number of linker molecules per antibody or fragment thereof.

As used herein, the term 'LAR' (Linker:Antibody Ratio) refers to the actual number or average number of linker molecules that have successfully conjugated to the antibody or fragment thereof. LAR is equivalent to the value of the integer defined herein as "z". Various methods of determining the linker loading are known in the art. In some embodiments the LAR is determined by the reaction of Mal-vc-PAB-MMAE as a surrogate payload for the linkers and analysed using HIC.

Conjugate Properties

In any of the various embodiments described herein, an antibody or fragment thereof will be capable of retaining its binding efficacy to its target whilst enabling optimal recruitment of anti-Gal. In one embodiment, cetuximab retains its ability to bind EGFR whilst being conjugated to an average of up to five, such as up to twenty, in particular up to thirty linker molecules.

In some embodiments, a conjugate of the invention may exhibit one or more of the following properties:

a) Conjugation of the linkers to the antibody or fragment thereof may not significantly alter the binding efficacy to the target over the unconjugated counterpart;

b) Conjugation of the alpha-Gal containing linkers may enable high levels of LAR without concomitantly high levels of aggregation due to the hydrophilic properties of the oligosaccharide;

c) Addition of the alpha-Gal containing linkers may enable the antibody or fragment thereof to be more stable;

d) A preference for heavy or light chain conjugation depending on the chosen linker and/or conjugation approach;

e) Conjugation of one chosen linker that comprises a high multiplicity of alpha-Gal units may exhibit optimal properties over several conjugation sites with equal loadings of alpha-Gal;

f) Conjugation of the linkers to the antibody or fragment thereof may lead to an enhanced pharmacokinetic profile.

Salts and Derivatives Thereof

A reference to a compound of formula (I) and sub-groups thereof also includes ionic forms, salts, solvates, isomers (including geometric and stereochemical isomers), tautomers, N-oxides, esters, isotopes and protected forms thereof, for example, as discussed below; preferably, the salts or tautomers or isomers or N-oxides or solvates thereof; and more preferably, the salts or tautomers or N-oxides or solvates thereof, even more preferably the salts or tautomers or solvates thereof. Hereinafter, compounds and their ionic forms, salts, solvates, isomers (including geometric and stereochemical isomers), tautomers, N-oxides, esters, isotopes and protected forms thereof as defined in any aspect of the invention (except intermediate compounds in chemical processes) are referred to as "compounds of the invention".

Compounds of formula (I) can exist in the form of salts, for example acid addition salts or, in certain cases salts of organic and inorganic bases such as carboxylate, sulfonate and phosphate salts. All such salts are within the scope of this invention, and references to compounds of formula (I) include the salt forms of the compounds. In one embodiment, the compound of formula (I) exists as the phosphate salt.

The salts of the present invention can be synthesized from the parent compound that contains a basic moiety by conventional chemical methods such as methods described in *Pharmaceutical Salts: Properties, Selection, and Use*, P.

Heinrich Stahl (Editor), Camille G. Wermuth (Editor), ISBN: 3-90639-026-8, Hardcover, 388 pages, August 2002. Generally, such salts can be prepared by reacting the base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, methanesulfonic (mesylate), ethanesulfonic, naphthalenesulfonic, valeric, acetic, propanoic, butanoic, malonic, glucuronic and lactobionic acids. One particular salt is the hydrochloride salt. Another particular salt is the hydrogensulfate salt, also known as a hemisulfate salt.

Salts further include, by way of example only, sodium, potassium, calcium, magnesium, ammonium, tetraalkylammonium, and the like.

Where the compounds of formula (I) contain an amine function, these may form quaternary ammonium salts, for example by reaction with an alkylating agent according to methods well known to the skilled person. Such quaternary ammonium compounds are within the scope of formula (I).

The compounds of the invention may exist as mono- or di-salts depending upon the pKa of the acid from which the salt is formed.

The salt forms of the compounds of the invention are typically pharmaceutically acceptable salts, and examples of pharmaceutically acceptable salts are discussed in Berge et al., 1977, "Pharmaceutically Acceptable Salts," J. Pharm. Sci., Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Pharmaceutically acceptable solvates of the compound of the invention are within the scope of the invention.

Compounds of formula (I) containing an amine function may also form N-oxides. A reference herein to a compound of formula (I) that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (mCPBA), for example, in an inert solvent such as dichloromethane.

It will be appreciated by those skilled in the art that certain protected derivatives of compounds of formula (I), which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". All such prodrugs of compounds of the invention are included within the scope of the invention. Examples of pro-drug functionality suitable for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within compounds of the invention.

Also included within the scope of the compound and various salts of the invention are polymorphs thereof.

Compounds of formula (I) may exist in a number of different geometric isomeric, and tautomeric forms and references to compounds of formula (I) include all such forms. For the avoidance of doubt, where a compound can exist in one of several geometric isomeric or tautomeric forms and only one is specifically described or shown, all others are nevertheless embraced by formula (I).

The present invention includes all pharmaceutically acceptable isotopically-labeled compounds of the invention, i.e. compounds of formula (I), wherein one or more atoms are replaced by atoms having the same atomic number, but an atomic mass or mass number different from the atomic mass or mass number usually found in nature.

Examples of isotopes suitable for inclusion in the compounds of the invention comprise isotopes of hydrogen, such as $^{2}$H (D) and $^{3}$H (T), carbon, such as $^{11}$C, $^{13}$O and $^{14}$O, fluorine, such as $^{18}$F, nitrogen, such as $^{13}$N and $^{15}$N, oxygen, such as $^{15}$O, $^{17}$O and $^{18}$O.

Certain isotopically-labelled compounds of formula (I), for example, those incorporating a radioactive isotope, are useful in drug and/or substrate tissue distribution studies.

The compounds of formula (I) can also have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^3$H (T), and carbon-14, i.e. $^{14}$C, are particularly useful for this purpose in view of their ease of incorporation and ready means of detection.

Substitution with heavier isotopes such as deuterium, i.e. $^2$H (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining target occupancy.

Isotopically-labeled compounds of formula (I) can generally be prepared by conventional techniques known to those skilled in the art or by processes analogous to those described in the accompanying Examples and Preparations using appropriate isotopically-labeled reagents in place of the non-labeled reagent previously employed.

Methods for the Preparation of Compounds of Formula (I)

In this section, as in all other sections of this application unless the context indicates otherwise, references to formula (I) also include all other sub-groups and examples thereof as defined herein.

The compounds pertaining to the invention described herein may be prepared in a stepwise synthetic sequence as illustrated in the Processes and Schemes below. The syntheses involve the preparation of various central constructs which then enable the choice of branching and length of linker with which to connect the two binding moieties. Compounds of formula (I) can be prepared in accordance with synthetic methods well known to the skilled person. For example, one skilled in the art will appreciate that the chemical steps and choice of protecting groups may be managed in any order to enable synthetic success.

In some embodiments, a compound of formula (A) may comprise a linker ($S_B$) that comprises one or more linker components. Exemplary linker components include but are not limited to 6-maleimidocaproyl (MC), maleimidopropanoyl (MP), valine-citrulline (vc) alanine-phenylalanine (ala-phe), N-succinimidyl 4-(2-pyridylthio)pentanoate (SPP) and 4-(n-malei midomethyl)cyclohexane 1-carboxylate (SMCC).

In some embodiments, a compound of formula (A) may comprise a linker ($S_B$) that is capable of reacting with a free thiol on an antibody to form a covalent bond. The compounds of the invention expressly contemplate but are not limited to antibody conjugates prepared with linker reagents: BMPEO, BMPS, EMCS, GMBS, HBVS, LC-SMCC, MBS, MPBH, SBAP, SIA, SIAB, SMCC, SMPB, sulfo-EMCS, sulfo-GMBS, sulfo-KMUS, sulfo-MBS, sulfo-SIAB, sulfo-SMCC, sulfo-SMPB and SVSB. Other functional groups besides pyrrolidine-2,5-dione (maleimide) which are reactive with a thiol group on an antibody include iodoacetamide, bromocetamide, vinyl pyridine disulphide, pyridyl disulphide, isocyanate, isothiocyanate, activated esters, sulfonyl chlorides and acid chlorides.

In some embodiments, a linker has the functionality that is capable of reacting with electrophilic groups on an antibody. Exemplary electrophilic groups include but are not limited to aldehyde, ketone and carbonyl groups. Additionally a heteroatom of the reactive functionality of the linker may react with an electrophilic group on an antibody. Typical examples include but are not limited to hydrazine, oxime, amino, hydrazide, thiosemicarbazone, hydrazine carboxylate and aryl hydrazide.

In some embodiments, a compound of formula (A) may comprise a linker ($S_B$) that is capable of reacting with a free amine on an antibody to form a covalent bond. The compounds of the invention expressly contemplate but are not limited to antibody conjugates prepared using carboxylic acid activating agents such as: N-hydroxysuccinimide (NHS), 2-succinimido-1,1,3,3-tetra-methyluronium tetrafluoroborate (TSTU), and benzotriazol-1-yl-oxytripyrrolidinophosphonium hexafluorophosphate (PyBOP).

According to a further aspect of the invention there is provided a process for preparing a compound of formula (I) as defined hereinbefore which comprises:

(a) preparing a compound of formula (IA) wherein $X_1$ represents —S— by reacting a compound of formula (III) wherein the antibody or antigen binding fragment contains at least one reactive thiol group with a compound of formula (II) wherein $S_1$ is terminated with maleimide:

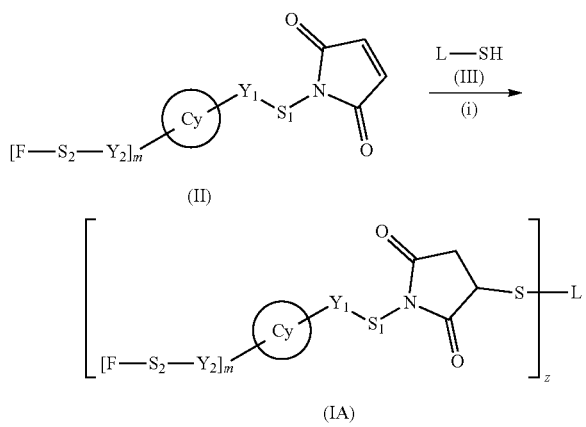

wherein F, $S_2$, $Y_2$, m, z, Cy, $Y_1$ and $S_1$ are as defined hereinbefore; or (b) preparing a compound of formula (IC) wherein $X_1$ represents —NH$_2$ and $S_1$ contains —S—CH$_2$—CH$_2$—CH$_2$—C(=NH)—, by reacting a compound of formula (IIIA) wherein the antibody or antigen binding fragment contains at least one reactive thiol group with a compound of formula (II) wherein $S_1$ is terminated with maleimide:

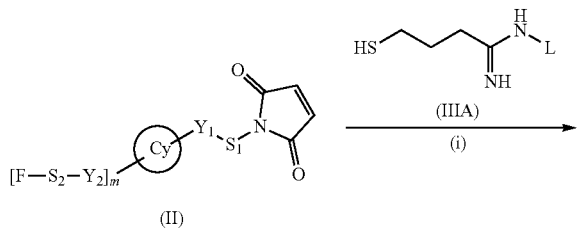

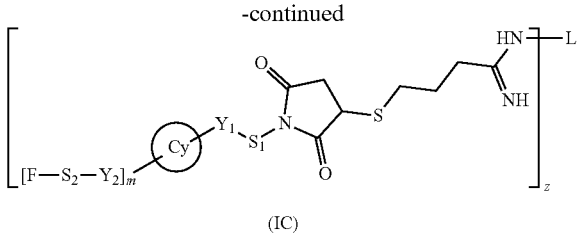

(IC)

wherein F, $S_2$, $Y_2$, m, z, Cy, $Y_1$, $S_1$ and L are as defined hereinbefore; or (c) preparing a compound of formula (IB) wherein $X_1$ represents —$NH_2$ by reacting a compound of formula (IIB) wherein $S_1$ is terminated with a N-hydroxysuccinimide group with compounds of formula (IIIB) wherein the antibody or antigen binding fragment contains at least one reactive amino group:

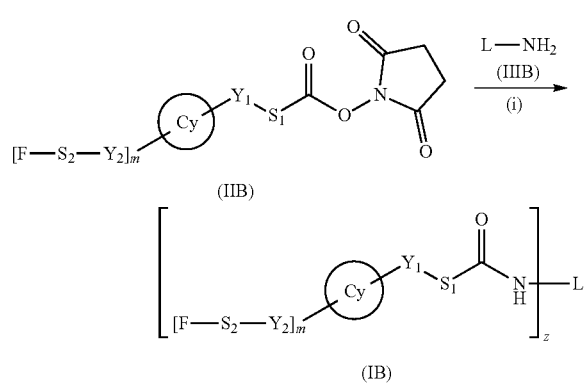

wherein F, $S_2$, $Y_2$, m, z, Cy, $Y_1$, $S_1$ and L are as defined hereinbefore; and/or (d) interconversion of a compound of formula (I) or protected derivative thereof to a further compound of formula (I) or protected derivative thereof.

Processes (a) and (b) typically comprise a thiol-maleimide reaction; a Michael addition reaction of a reactive thiol group with an α, β-unsaturated ketone such as maleimide.

Preferred conditions comprise incubation of the linker-maleimide intermediates with antibodies or fragments thereof that contain a reactive thiol, in a suitable buffer as described herein at room temperature. Typical Linker:Antibody ratios (LAR) are dependent on the number of free thiol groups present on the antibody or fragment thereof, but typically range from 2-8.

Process (c) typically comprises an amide bond formation reaction in the presence of an activated ester. Typical conditions comprise incubation of the linker-NHS ester with antibodies or fragments thereof that contain a reactive amino, in a suitable buffer at room temperature. Typical Linker:Antibody ratios (LAR) are dependent on the number of free amino groups present on the antibody or fragment thereof, but typically range from 2-20.

Process (d) typically comprises interconversion procedures known by one skilled in the art. For example, in compounds of formula (I), a first substituent may be converted by methods known by one skilled in the art into a second, alternative substituent. A wide range of well known functional group interconversions are known by a person skilled in the art for converting a precursor compound to a compound of formula (I) and are described in *Advanced Organic Chemistry* by Jerry March, 4$^{th}$ Edition, John Wiley & Sons, 1992. For example possible metal catalysed functionalisations such as using organo-tin reagents (the Stille reaction), Grignard reagents and reactions with nitrogen nucleophiles are described in 'Palladium Reagents and Catalysts' [Jiro Tsuji, Wiley, ISBN 0-470-85032-9] and Handbook of OrganoPalladium Chemistry for Organic Synthesis [Volume 1, Edited by Ei-ichi Negishi, Wiley, ISBN 0-471-31506-0].

If appropriate, the reactions previously described in processes (a) (b) and (c) are followed or preceded by one or more reactions known to the skilled of the art and are performed in an appropriate order to achieve the requisite substitutions defined above to afford other compounds of formula (I). Non-limiting examples of such reactions whose conditions can be found in the literature include:

protection of reactive functions,
deprotection of reactive functions,
halogenation,
dehalogenation,
dealkylation,
alkylation and arylation of amine, aniline, alcohol and phenol,
Mitsunobu reaction on hydroxyl groups,
cycloaddition reactions on appropriate groups,
reduction of nitro, esters, cyano, aldehydes,
transition metal-catalyzed coupling reactions,
acylation,
sulfonylation/introduction of sulfonyl groups,
saponification/hydrolysis of ester groups,
amidification or transesterification of ester groups,
esterification or amidification of carboxylic groups,
halogen exchange,
nucleophilic substitution with amine, thiol or alcohol,
reductive amination,
oxime formation on carbonyl and hydroxylamine groups,
S-oxidation,
N-oxidation,
salification.

Compounds of formula (III) may contain at least one reactive thiol group available for reaction. Generation of the reactive thiol group may be achieved through reduction of the antibody or antigen binding fragment with TCEP.

Preferred conditions comprise either 1.1 eq TCEP:Ab, 4.2 eq TCEP:Ab or 8 eq TCEP:Ab.

Alternatively, the generation of reactive thiol groups may be achieved through reaction of at least one lysine residue on the antibody or antigen binding fragment with a thiolating agent such as Traut's reagent (2-iminothiolane).

Preferred conditions comprise 12.2 eq of 2-iminothiolane:Ab for low LAR and 30.5 eq 2-iminothiolane:Ab for high LAR.

Compounds of formula (II) and (IIB) may be prepared according to the methods described in Scheme 1 from compounds of formula (V) and (VI), followed by reaction with succinimidyl 4-(N-maleimidomethyl)cyclohexane-1-carboxylate (SMCC) or di(N-succinimydyl)glutarate (DSG):

Scheme 1

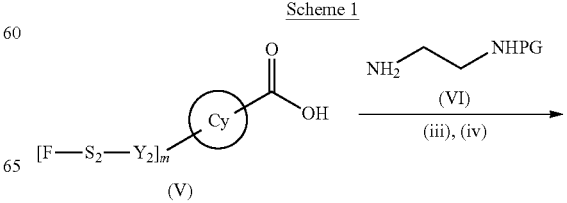

-continued

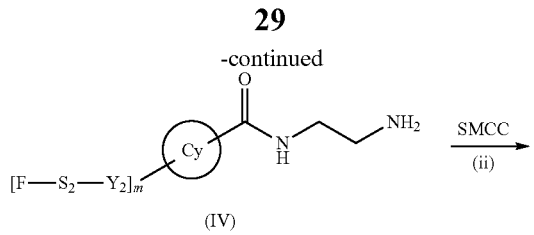

(IV)

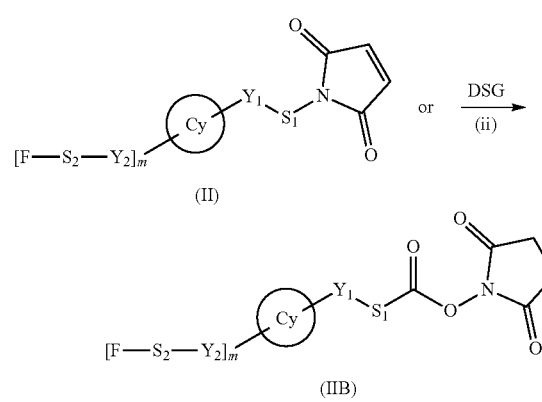

wherein PG is a protecting group such as monomethoxy trityl; $S_1$ is terminated with maleimide or NHS, $Y_1$ is CONH and $S_2$, $Y_2$, m, Cy, and F are as defined hereinbefore.

Compounds of formula (II) may be prepared from compounds of formula (IV), interconversion of a terminal amino group into a reactive maleimide group. Preferred conditions comprise reaction of the terminal amino group with succinimidyl 4-(N-maleimidomethyl)cyclohexane-1-carboxylate (SMCC) in DMSO at room temperature. Alternatively compounds of formula (IIB) may be prepared from compounds of formula (IV) by interconversion of a terminal amino group into a reactive NHS group. Preferred conditions comprise reaction with cross-linker di-(N-succinimidyl)glutarate in a suitable anhydrous organic solvent such as DMF and DMSO or a combination thereof.

Compounds of formula (IV) may be prepared from compounds of formula (V) and (VI), according to process steps (iii) and (iv), and amide bond formation step followed by a suitable deprotection step. A typical amide bond formation step comprises activation of a carboxylic acid with either phosphate containing reagents, triazine-based reagents or carbodiimide containing reagents in the presence of an organic base in an organic solvent. Preferred conditions comprise HATU ((1-[bis(dimethylamino)methylene]-1H-1, 2,3-triazolo[4,5-b]pyridinium 3-oxid hexafluorophosphate) with either triethylamine or diisopropylethylamine in DMF or a mixture of DMF and DMSO. Wherein PG comprises monomethoxytrityl, the deprotection reaction is mediated with acid. Preferred conditions comprise 0.2M aqueous HCl at room temperature.

Alternatively compounds of formula (II) may be prepared according to the methods described in Scheme 1A from compounds of formula (VA), followed by reaction with succinimidyl 4-(N-maleimidomethyl)cyclohexane-1-carboxylate (SMCC).

Scheme 1A

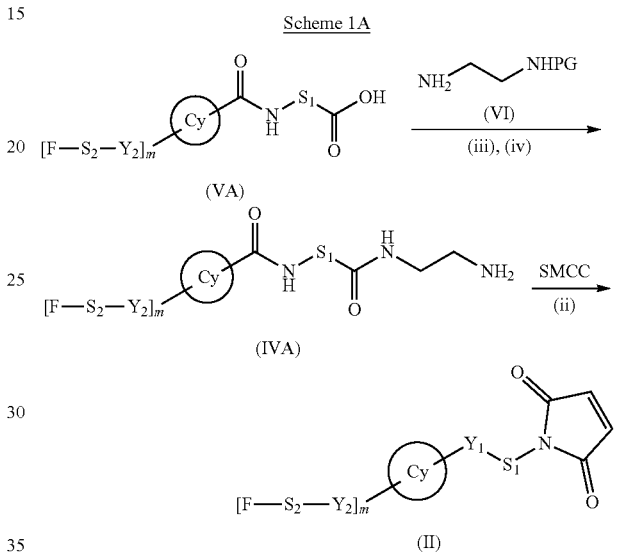

wherein PG is a protecting group such as monomethoxy trityl; $S_1$ is terminated with maleimide, $Y_1$ is CONH and $S_2$, $Y_2$, m, Cy, and F are as defined hereinbefore.

Compounds of formula (II) may be prepared from compounds of formula (VA) and (VI) according to process steps (iii) and (iv) as previously described in Scheme 1. Interconversion of the terminal amino group into a reactive maleimide group may be achieved as described for process step (ii) in Scheme 1 using SMCC.

Compounds of formula (V) and (VA) (wherein $S_2$ is terminated with —NHCO—$CH_2$—) may be prepared according to the methods described in Scheme 2 from compounds of formula (VIII), (IX) and (IXA).

Scheme 2

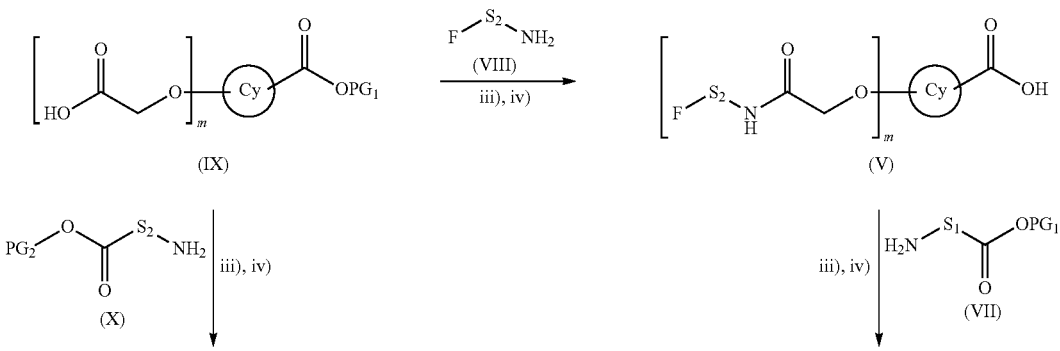

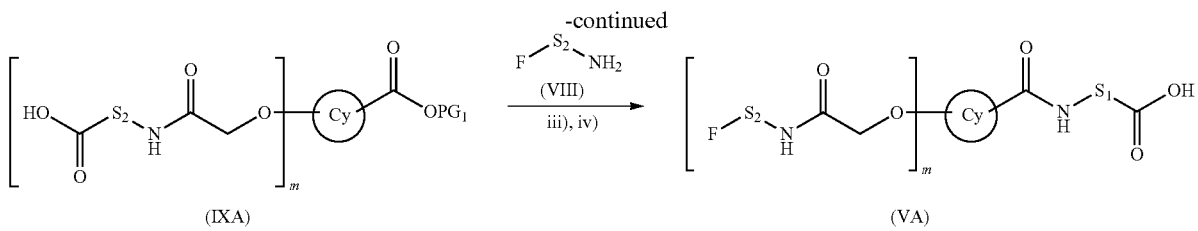

wherein m, Cy, $S_1$, $S_2$ and F are as defined hereinbefore, $PG_1$ is a protecting group comprising either tert-butyl, methyl, ethyl or benzyl and $PG_2$ is an orthogonal protecting group comprising either methyl, ethyl or tert-butyl.

Compounds of formula (V), (IXA) and (VA) may be prepared from compounds of formula (IX) according to process steps (iii) and (iv), an amide bond formation step followed by a suitable deprotection reaction. Wherein PG comprises benzyl, the deprotection reaction is mediated by catalytic hydrogenation. Preferred conditions comprise 10% Pd/C in MeOH/EtOH or water or any combination thereof under an atmosphere of hydrogen (from between 15-70 psi). Alternatively, deprotection may be mediated by a phase transfer reaction. Preferred conditions comprise TEA and water at room temperature for 16 hours.

Wherein PG comprises methyl, ethyl or tert-butyl, an acid or base mediated deprotection reaction as required by the protecting group is employed. Wherein acid mediated deprotection conditions are required, preferred conditions comprise TFA, 4M HCl in dioxane, or 37% HCl in water with a co-solvent of DCM or water as necessary. Wherein base mediated conditions are required, preferred conditions comprise either sodium or lithium hydroxide in aqueous media such as methanol or THF with water.

Compounds of formula (IX) may be prepared according to the methods described in Scheme 3 from compounds of formula (XI) and (XII).

Scheme 3

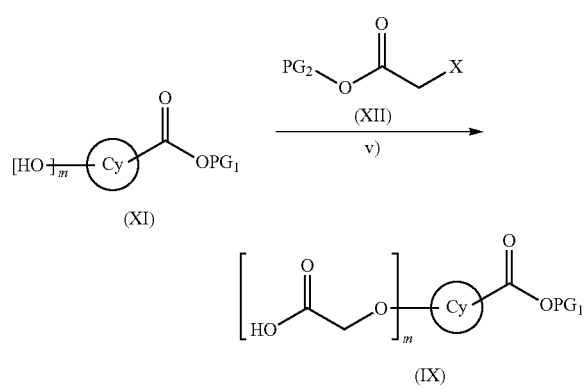

wherein m and Cy are as defined hereinbefore, $PG_1$ is a protecting group comprising either tert-butyl, methyl, ethyl or benzyl, $PG_2$ is an orthogonal protecting group comprising either methyl, ethyl or tert-butyl and X is Cl, Br or I.

Compounds of formula (IX) may be prepared from compounds of formula (XI) and (XII) according to process step (v), an alkylation reaction. Typical conditions comprise an inorganic base in a polar organic solvent at room temperature. Preferred conditions comprise potassium carbonate in DMF.

When Cy is bi-phenyl, or triphenyl, compounds of formula (XI) may be prepared by employment of a Suzuki reaction to construct the bi/tri-phenyl unit. Preferred conditions comprise tetrakistriphenyl phosphine palladium (0) or [1,1'-bis(diphenylphosphino)ferrocene]dichloropalladium (II) complex with dichloromethane with sodium carbonate, potassium acetate or sodium bicarbonate in dioxane and water at 100-110° C. When suitable required protecting groups are employed, such as TBS, such protecting groups may be deprotected using a fluoride mediated deprotection. Preferred conditions comprise TBAF in THF at room temperature.

Alternatively, wherein Cy is bi/tri-phenyl, compounds of formula (XI) may be prepared directly by employment of a Suzuki reaction to construct the bi/tri-phenyl unit using conditions as described above and herein.

Compounds of formula (III), (IIIA), (IIIB), (VI), (VIII), (XII), (VII), and (X) are either commercially available or prepared according to the methods described herein.

It will be appreciated that certain intermediates described herein represent novel compounds not previously known in the art. Thus, according to a further aspect of the invention there is provided an intermediate compound selected from a compound of formula (II), (IIB), (V), (VA), (IX) or (XI) as defined hereinbefore.

One skilled in the art will appreciate that one may choose the appropriate combination of steps described above to generate the highest yields for the Examples and Preparations described herein.

Pharmaceutical Compositions

While it is possible for the compound of formula (I) to be administered alone, it is preferable to present it as a pharmaceutical composition (e.g. formulation).

Thus, according to a further aspect, the invention provides a pharmaceutical composition, and methods of making a pharmaceutical composition comprising (e.g admixing) at least one compound of the invention together with one or more pharmaceutically acceptable excipients and optionally other therapeutic or prophylactic agents, as described herein. It will be appreciated that when the pharmaceutical composition comprises one or more further therapeutic agents, said agents may comprise further differing compounds of formula (I).

The pharmaceutically acceptable excipient(s) can be selected from, for example, carriers (e.g. a solid, liquid or semi-solid carrier), adjuvants, diluents, fillers or bulking agents, granulating agents, coating agents, release-controlling agents, binding agents, disintegrants, lubricating agents, preservatives, antioxidants, buffering agents, suspending agents, thickening agents, flavouring agents, sweeteners, taste masking agents, stabilisers or any other excipients conventionally used in pharmaceutical compositions. Examples of excipients for various types of pharmaceutical compositions are set out in more detail below.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity (i.e. generally recognised as safe (GRAS)), irritation, allergic response, or other problem or complication, commensurate with a reasonable benefit/risk ratio. Each carrier, excipient, etc. must also be "acceptable" in the sense of being compatible with the other ingredients of the formulation.

Pharmaceutical compositions containing compounds of the invention can be formulated in accordance with known techniques, see for example, Remington's Pharmaceutical Sciences, Mack Publishing Company, Easton, Pa., USA.

The pharmaceutical compositions can be in any form suitable for parenteral, intranasal, intrabronchial, sublingual, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump or syringe driver.

Pharmaceutical formulations adapted for parenteral administration include aqueous and non-aqueous sterile injection solutions which may contain anti-oxidants, buffers, bacteriostats, co-solvents, surface active agents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

The formulations may be presented in unit-dose or multi-dose containers, for example sealed ampoules, vials and prefilled syringes, and may be stored in a freeze-dried (lyophilised) condition requiring only the addition of the sterile liquid carrier, for example water for injections, immediately prior to use.

The pharmaceutical formulation can be prepared by lyophilising a compound of the invention. Lyophilisation refers to the procedure of freeze-drying a composition. Freeze-drying and lyophilisation are therefore used herein as synonyms.

Extemporaneous injection solutions and suspensions may be prepared from sterile powders, granules and tablets.

Pharmaceutical compositions of the present invention for parenteral injection can also comprise pharmaceutically acceptable sterile aqueous or non-aqueous solutions, dispersions, suspensions or emulsions as well as sterile powders for reconstitution into sterile injectable solutions or dispersions just prior to use.

Examples of suitable aqueous and non-aqueous carriers, diluents, solvents or vehicles include water, ethanol, polyols (such as glycerol, propylene glycol, polyethylene glycol, and the like), carboxymethylcellulose and suitable mixtures thereof, vegetable oils (such as sunflower oil, safflower oil, corn oil or olive oil), and injectable organic esters such as ethyl oleate. Proper fluidity can be maintained, for example, by the use of thickening or coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various anti-bacterial and antifungal agents, for example, paraben, chlorobutanol, phenol, sorbic acid, and the like. It may also be desirable to include agents to adjust tonicity such as sugars, sodium chloride, and the like. Prolonged absorption of the injectable pharmaceutical form may be brought about by the inclusion of agents which delay absorption such as aluminium monostearate and gelatin.

In one preferred embodiment of the invention, the pharmaceutical composition is in a form suitable for i.v. administration, for example by injection or infusion. For intravenous or subcutaneous administration, the solution can be dosed as is, or can be injected into an infusion bag (containing a pharmaceutically acceptable excipient, such as 0.9% saline or 5% dextrose), before administration.

In another preferred embodiment, the pharmaceutical composition is in a form suitable for subcutaneous (s.c.) administration.

The compound of the invention may be formulated with a carrier and administered in the form of nanoparticles, the increased surface area of the nanoparticles assisting their absorption. In addition, nanoparticles offer the possibility of direct penetration into the cell. Nanoparticle drug delivery systems are described in "Nanoparticle Technology for Drug Delivery", edited by Ram B Gupta and Uday B. Kompella, Informa Healthcare, ISBN 9781574448573, published 13 Mar. 2006. Nanoparticles for drug delivery are also described in J. Control. Release, 2003, 91 (1-2), 167-172, and in Sinha et al., Mol. Cancer Ther. August 1, (2006) 5, 1909.

The pharmaceutical compositions typically comprise from approximately 1% (w/w) to approximately 95% (w/w) active ingredient and from 99% (w/w) to 5% (w/w) of a pharmaceutically acceptable excipient or combination of excipients. Preferably, the compositions comprise from approximately 20% (w/w) to approximately 90% (w/w) active ingredient and from 80% (w/w) to 10% of a pharmaceutically acceptable excipient or combination of excipients. The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, pre-filled syringes, dragées, tablets or capsules.

The pharmaceutically acceptable excipient(s) can be selected according to the desired physical form of the formulation and can, for example, be selected from diluents (e.g solid diluents such as fillers or bulking agents; and liquid diluents such as solvents and co-solvents), disintegrants, buffering agents, lubricants, flow aids, release controlling (e.g. release retarding or delaying polymers or waxes) agents, binders, granulating agents, pigments, plasticizers, antioxidants, preservatives, flavouring agents, taste masking agents, tonicity adjusting agents and coating agents.

The skilled person will have the expertise to select the appropriate amounts of ingredients for use in the formulations. For example tablets and capsules typically contain 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral or subcutaneous formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

The compounds of the invention can also be formulated as solid dispersions. Solid dispersions are homogeneous extremely fine disperse phases of two or more solids. Solid solutions (molecularly disperse systems), one type of solid dispersion, are well known for use in pharmaceutical technology (see (Chiou and Riegelman, J. Pharm. Sci., 60, 1281-1300 (1971)) and are useful in increasing dissolution rates and increasing the bioavailability of poorly water-soluble drugs.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions. One example of a patient pack includes a prefilled syringe. Such pre-filled syringes already contain the drug substance. The front end portion of a pre-filled syringe to which a needle is to be attached is sealed with a nozzle cap. Prior to injection, the nozzle cap is removed from the front end portion and a needle is attached thereto. A gasket is then slid by pushing a plunger rod toward the front end portion so that the drug is expelled.

Compositions for nasal delivery include ointments, creams, sprays, patches, gels, liquid drops and inserts (for example intraocular inserts). Such compositions can be formulated in accordance with known methods.

Examples of formulations for rectal or intra-vaginal administration include pessaries and suppositories which may be, for example, formed from a shaped moldable or waxy material containing the active compound. Solutions of the active compound may also be used for rectal administration.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compound of the invention will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

The active compound will be administered to a patient in need thereof (for example a human or animal patient) in an amount sufficient to achieve the desired therapeutic effect.

Therapeutic Uses

According to a further aspect of the invention, there is provided a compound of formula (I) as defined herein for use in therapy.

It will be appreciated that the therapeutic use of the compounds of the invention is determined by the selection of the antibody or antigen binding fragment thereof.

For example, in the embodiment when the antibody or antigen binding fragment thereof is an EGFR antibody (e.g. cetuximab or nimotuzumab) or a fragment thereof the compound of formula (I) is for use in the treatment of cancer.

Thus, according to a further aspect of the invention there is provided a compound of formula (I) as defined herein wherein the antibody or antigen binding fragment thereof is an EGFR antibody (e.g. cetuximab or nimotuzumab) or a fragment thereof for use in the treatment of cancer.

According to a further aspect of the invention there is provided a method of treating cancer which comprises administering to an individual in need thereof a compound of formula (I) as defined herein wherein the antibody or antigen binding fragment thereof is EGFR antibody (e.g. cetuximab or nimotuzumab) or a fragment thereof.

Furthermore, in the embodiment when the antibody or antigen binding fragment thereof is a pathogen specific antibody or a fragment thereof, the compound of formula (I) is for use in the treatment of a bacterial infection.

Thus, according to a further aspect of the invention there is provided a compound of formula (I) as defined herein wherein the antibody or antigen binding fragment thereof is a pathogen specific antibody or a fragment thereof, for use in the treatment of a bacterial infection.

According to a further aspect of the invention there is provided a method of treating a bacterial infection which comprises administering to an individual in need thereof a compound of formula (I) as defined herein wherein the antibody or antigen binding fragment thereof is a pathogen specific antibody or a fragment thereof.

The compound of the invention is generally administered to a subject in need of such administration, for example a human or animal patient, preferably a human.

The compound of the invention will typically be administered in amounts that are therapeutically or prophylactically useful and which generally are non-toxic. However, in certain situations (for example in the case of life threatening diseases), the benefits of administering a compound of the invention may outweigh the disadvantages of any toxic effects or side effects, in which case it may be considered desirable to administer a compound of the invention in amounts that are associated with a degree of toxicity.

The compound of the invention may be administered over a prolonged term (i.e. chronic administration) to maintain beneficial therapeutic effects or may be administered for a short period only (i.e. acute administration). Alternatively they may be administered in a continuous manner or in a manner that provides intermittent dosing (e.g. a pulsatile manner).

A typical daily dose of the compound of the invention can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The compound of the invention can either be administered on a daily basis or on a repeat basis every 2, or 3, or 4, or 5, or 6, or 7, or 10 or 14, or 21, or 28 days for example. Alternatively, the compound of the invention can be administered by infusion, multiple times per day.

The compound of the invention may be administered in a range of doses, for example 1 to 1500 mg, 2 to 800 mg, or 5 to 500 mg, e.g. 2 to 200 mg or 10 to 1000 mg, particular examples of doses including 10, 20, 50 and 80 mg. The compound of the invention may be administered once or more than once each day. The compound of the invention can be administered continuously (i.e. taken every day without a break for the duration of the treatment regimen). Alternatively, the compound of the invention can be administered intermittently (i.e. taken continuously for a given period such as a week, then discontinued for a period such as a week and then taken continuously for another period such as a week and so on throughout the duration of the treatment regimen). Examples of treatment regimens involving intermittent administration include regimens wherein administration is in cycles of one week on, one week off; or two weeks on, one week off; or three weeks on, one week off; or two weeks on, two weeks off; or four weeks on two weeks off; or one week on three weeks off—for one or more cycles, e.g. 2, 3, 4, 5, 6, 7, 8, 9 or 10 or more cycles.

In one particular dosing schedule, a patient will be given an infusion of a compound of the invention for periods of one hour daily for up to ten days in particular up to five days for one week, and the treatment repeated at a desired interval such as two to four weeks, in particular every three weeks.

More particularly, a patient may be given an infusion of a compound of the invention for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

In a further particular dosing schedule, a patient is given a continuous infusion for a period of 12 hours to 5 days, and in particular a continuous infusion of 24 hours to 72 hours.

Ultimately, however, the quantity of compound of the invention administered and the type of composition used will be commensurate with the nature of the disease or physiological condition being treated and will be at the discretion of the physician.

It will be appreciated that the compound of the invention can be used as a single agent or in combination with other therapeutic agents. Combination experiments can be performed, for example, as described in Chou T C, Talalay P. Quantitative analysis of dose-effect relationships: the combined effects of multiple drugs or enzyme inhibitors. Adv Enzyme Regulat 1984; 22: 27-55.

Where the compound of the invention is administered in combination therapy with one, two, three, four or more other therapeutic agents (preferably one or two, more preferably one), the agents can be administered simultaneously or sequentially. In the latter case, the two or more agents will be administered within a period and in an amount and manner that is sufficient to ensure that an advantageous or synergistic effect is achieved. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s). These dosages may be administered for example once, twice or more per course of treatment, which may be repeated for example every 7, 14, 21 or 28 days.

It will be appreciated that the preferred method and order of administration and the respective dosage amounts and regimes for each component of the combination will depend on the particular other medicinal agent and compound of the invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound of the invention and the one or more other therapeutic agent(s) when given as a combination may be determined by the person skilled in the art. Said ratio and the exact dosage and frequency of administration depends on the particular compound of the invention and the other therapeutic agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compound of present invention. A particular weight ratio for the compound of the invention and another therapeutic agent may range from 1/10 to 10/1, more in particular from 1/5 to 5/1, even more in particular from 1/3 to 3/1.

Anti-Cancer Therapy

Examples of cancers (and their benign counterparts) which may be treated (or inhibited) include, but are not limited to tumours of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, colon, rectum and anus), liver (hepatocellular carcinoma), gall bladder and biliary system, exocrine pancreas, kidney, lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, cervix, myometrium, endometrium, thyroid (for example thyroid follicular carcinoma), adrenal, prostate, skin and adnexae (for example melanoma, basal cell carcinoma, squamous cell carcinoma, keratoacanthoma, dysplastic naevus); haematological malignancies (i.e. leukemias, lymphomas) and premalignant haematological disorders and disorders of borderline malignancy including haematological malignancies and related conditions of lymphoid lineage (for example acute lymphocytic leukemia [ALL], chronic lymphocytic leukemia [CLL], B-cell lymphomas such as diffuse large B-cell lymphoma [DLBCL], follicular lymphoma, Burkitt's lymphoma, mantle cell lymphoma, T-cell lymphomas and leukaemias, natural killer [NK] cell lymphomas, Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenousleukemia [AML], chronic myelogenousleukemia [CML], chronic myelomonocyticleukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocyticleukemia); tumours of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumours, benign and malignant histiocytomas, and dermatofibrosarcomaprotuberans; tumours of the central or peripheral nervous system (for example astrocytomas, gliomas and glioblastomas, meningiomas, ependymomas, pineal tumours and schwannomas); endocrine tumours (for example pituitary tumours, adrenal tumours, islet cell tumours, parathyroid tumours, carcinoid tumours and medullary carcinoma of the thyroid); ocular and adnexal tumours (for example retinoblastoma); germ cell and trophoblastic tumours (for example teratomas, seminomas, dysgerminomas, hydatidiform moles and choriocarcinomas); and paediatric and embryonal tumours (for example medulloblastoma, neuroblastoma, Wilms tumour, and primitive neuroectodermal tumours); or syndromes, congenital or otherwise, which leave the patient susceptible to malignancy (for example Xeroderma Pigmentosum).

In one embodiment, the cancer is a solid tumor. In a further embodiment, the cancer is breast cancer, ovarian cancer, cervical cancer, colorectal cancer, liver cancer, prostate cancer or lung cancer.

In one embodiment, the cancer comprises a haematological malignancy. In a further embodiment, the haematological malignancy is one of myeloma, non-Hodgkin's lymphoma or chronic lymphocytic leukaemia.

Examples of other anticancer therapeutic agents or treatments that may be administered together (whether concurrently or at different time intervals) with the compound of the invention include but are not limited to:
  Topoisomerase I inhibitors;
  Antimetabolites;
  Tubulin targeting agents;
  DNA binder and topoisomerase II inhibitors;
  Alkylating Agents;
  Monoclonal Antibodies;
  Anti-Hormones;
  Signal Transduction Inhibitors;
  Proteasome Inhibitors;
  DNA methyl transferases;
  Cytokines and retinoids;
  Chromatin targeted therapies;
  Radiotherapy; and
  Other therapeutic or prophylactic agents, such as immunotherapy agents.

The compound of the invention may also be administered in conjunction with non-chemotherapeutic treatments such as radiotherapy, photodynamic therapy, gene therapy; surgery and controlled diets.

For use in combination therapy with another chemotherapeutic agent, the compound of the invention and one, two, three, four or more other therapeutic agents can be, for example, formulated together in a dosage form containing two, three, four or more therapeutic agents i.e. in a unitary pharmaceutical composition containing all components. In an alternative embodiment, the individual therapeutic agents may be formulated separately and presented together in the form of a kit, optionally with instructions for their use.

Anti-Infective Therapy

Examples of infective agents include any pathogen such as a bacteria, fungus, parasite or virus. Thus, in one embodiment, the disease or disorder mediated by and/or caused by an infective agent is bacterial infection.

Examples of such as bacterial infection include infection by the following bacteria: *Staphylococcus* sp. such as *Staphylococcus aureus* (including methicillin resistant *Staphylococcus aureus* (MRSA)), Clostridia sp (e.g. *Clostridium difficile, Clostridium tetani* and *Clostridium botulinum*), *Enterobacter* species, *Mycobacterium tuberculosis, Shigella* sp. such as *Shigelladysenteriae, Campylobacter* sp. such as *Campylobacterjejuni, Enterococcus* sp. such as *Enterococcus faecalis, Bacillus anthracis, Yersinia pestis, Bordetella pertussis, Streptococcal species, Salmonella thyphimurim, Salmonella enterica, Chlamydia* species, *Treponemapallidum, Neisseria gonorrhoeae, Borreliaburgdorferi, Vibrio cholerae, Corynebacterium diphtheriae, Helicobacter pylori*, Gram-negative pathogens, such as *Acinetobacter baumannii, Pseudomonas aeruginosa, Klebsiella pneumoniae*, and *Escherichia coli* (and including strains that are resistant to one or more classes of antibiotics, especially multi-drug resistant (MDR) strains).

Vaccine Therapy

According to a further aspect of the invention, there is provided a vaccine comprising an immunoconjugate as defined herein.

According to a further aspect of the invention, there is provided an adjuvant comprising an immunoconjugate as defined herein.

EXAMPLES

The invention will now be illustrated, but not limited, by reference to the specific embodiments described in the following examples. Compounds are named using an automated naming package such as AutoNom (MDL) or ChemDraw or are as named by the chemical supplier.

The following synthetic procedures are provided for illustration of the methods used; for a given preparation or step the precursor used may not necessarily derive from the individual batch synthesised according to the step in the description given.

Analytical Methods
LCMS
System 1
LCMS Agilent 1100 (quaternary pump); mass spectrometer: Waters Micromass ZQ Column: XBridge C18 4.6×50 mm, 5 μm.

Solvent: A=water; B=acetonitrile, C=10 mm ammonium formate in water; D=0.05% formic acid in acetonitrile Column temperature: 25° C., injection volume: 5 μL

| LCMS Method A: 4.5 minute acidic run | | | | | |
|---|---|---|---|---|---|
| Time (mins) | A (%) | B (%) | C (%) | D (%) | Flow (mL/min) |
| 0 | 95 | 0 | 0 | 5 | 2.0 |
| 3.5 | 0 | 95 | 0 | 5 | 2.0 |
| 4.5 | 0 | 95 | 0 | 5 | 2.0 |
| 4.6 | 95 | 0 | 0 | 5 | 2.0 |

| LCMS Method B: 4.5 minute buffered run | | | | | |
|---|---|---|---|---|---|
| Time (mins) | A (%) | B (%) | C (%) | D (%) | Flow (mL/min) |
| 0 | 0 | 5 | 95 | 0 | 2.0 |
| 3.5 | 0 | 95 | 5 | 0 | 2.0 |
| 4.5 | 0 | 95 | 5 | 0 | 2.0 |
| 4.6 | 0 | 5 | 95 | 0 | 2.0 |

| LCMS Method C: 8 minute acidic run | | | | | |
|---|---|---|---|---|---|
| Time (mins) | A (%) | B (%) | C (%) | D (%) | Flow (mL/min) |
| 0 | 95 | 0 | 0 | 5 | 2.0 |
| 3.5 | 5 | 90 | 0 | 5 | 2.0 |
| 8.0 | 5 | 90 | 0 | 5 | 2.0 |
| 8.10 | 95 | 0 | 0 | 5 | 2.0 |

System 2

LCMS Agilent 1100 (quaternary pump); mass spectrometer: PE SCIEX API 2000 MS/MS Column: Agilent Poroshell 120 column, SB-C18, 4.6 mm×30 mm, 2.7 μm Solvent: A=water; B=0.1% formic acid in acetonitrile Column temperature: 20° C., injection volume: 5 μL

| LCMS Method D: 4.5 minute acidic run | | | | | |
|---|---|---|---|---|---|
| Time (mins) | A (%) | B (%) | C (%) | D (%) | Flow (mL/min) |
| 0.5 | 95 | 5 | 0 | 5 | 2.0 |
| 1.5 | 0 | 100 | 0 | 5 | 2.0 |
| 4.0 | 0 | 100 | 0 | 5 | 2.0 |
| 4.3 | 95 | 5 | | | |
| 4.5 | 95 | 5 | 0 | 5 | 2.0 |

NMR

NMR details were recorded on either an Oxford Instruments AS400.

Abbreviations

Wherein the following abbreviations have been used, the following meanings apply:

AcOH is acetic acid;
aq. is aqueous;
br s is broad singlet;
δ is chemical shift in ppm;
d is doublet;
dd is doublet of doublets;
ddd is doublet of doublets of doublets;
DCM is dichloromethane;
DIPEA is diisopropylethylamine;
DMF is dimethylformamide;
DMSO is dimethylsulphoxide;
DMSO-$d_6$ is perdeuterated dimethylsulphoxide NMR solvent;
DSG is di-(N-succinimydyl)glutarate;
EtOH is ethanol;
EtOAc is ethyl acetate;
HATU is O-(7-azabenzotriazol-1-yl)-N,N,N',N'-tetramethyluronium hexafluorophosphate;
HPLC is high pressure liquid chromatography;
IMS is industrial methylated spirit (typically 5%-10% MeOH in EtOH);
μ is micro;
m is multiplet;
Mal is maleimide;
MeCN is acetonitrile;
MeOH is methanol;
mins is minutes;
mL is millilitre;
MMTr is monomethoxytrityl;
MS is mass spectrometry;
$NH_3$ is ammonia or ammonium hydroxide (28% aqueous solution);
NHS is N-hydroxysuccinimide; or N-hydroxysuccinimidyl;
NMR is nuclear magnetic resonance;
Pd/C is (typically 5%-10%) palladium on charcoal hydrogenation catalyst (water-wet);
Pd(PPh$_3$)$_4$ is tetrakis triphenylphosphine palladium (0);
ppm is parts per million;
q is quartet;
Rt is retention time;
s is singlet;
SMCC is succinimidyl 4-(N-maleimidomethyl)cyclohexane-1-carboxylate;
t is triplet;
TBAF is tetra-n-butylammonium fluoride;
TBME is tert-butyl methyl ether;
TEA is triethylamine;
TBS is tert-butyldimethylsilyloxy;
TFA is trifluoroacetic acid and
THF is tetrahydrofuran.

Wherein alpha-Gal is referred to, the following intermediate applies:

3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amine

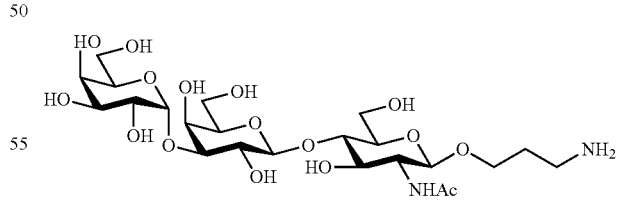

This intermediate may be prepared according to the methods described by Bovin et al (Mendeleev Communications (2002), (4), 143-145).

Preparations 1-19 describe the methods used to prepare intermediates from the key linker molecules required for conjugation into the Examples, as described by processes (a)-(d) and Schemes 1, 1A, 2 and 3 as described hereinbefore.

Preparation 1

4'-(2-((3-(((2R,3R,4R,5S,6R)-3-Acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-N-(2-(4-((2,5-dioxo-2,5-dihydro-1H-pyrrol-1-yl)methyl)cyclohexane-1-carboxamido)ethyl)-[1,1'-biphenyl]-3-carboxamide

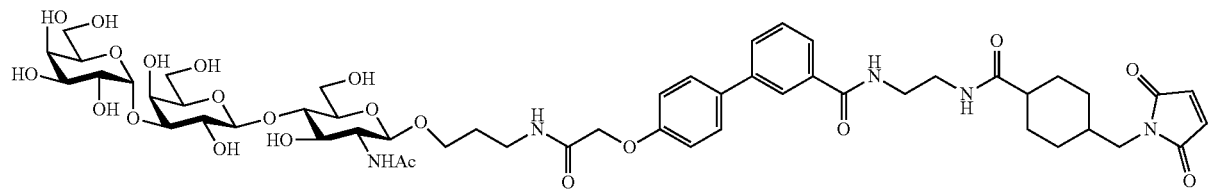

To a solution of 4'-(2-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-N-(2-aminoethyl)-[1,1'-biphenyl]-3-carboxamide (Preparation 3, 5.0 mg, 2.26 μmol) in DMSO (400 μL) was added a solution of SMCC (2.2 mg, 6.57 μmol) in DMSO (100 μL). The resulting solution was stirred at room temperature for 18 hours and then dried under vacuum. The crude residue was used directly in the next step.

LCMS Method B: Rt=1.97 mins, ES$^+$ MS m/z 1118.5 [M+H]$^+$

Preparation 2

2,2',2''-((5'-((2-(4-((2,5-Dioxo-2,5-dihydro-1H-pyrrol-1-yl)methyl)cyclohexane-1-carboxamido)ethyl)carbamoyl)-[1,1'-biphenyl]-3,3',5-triyl)tris(oxy))tris(N-(3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)acetamide)

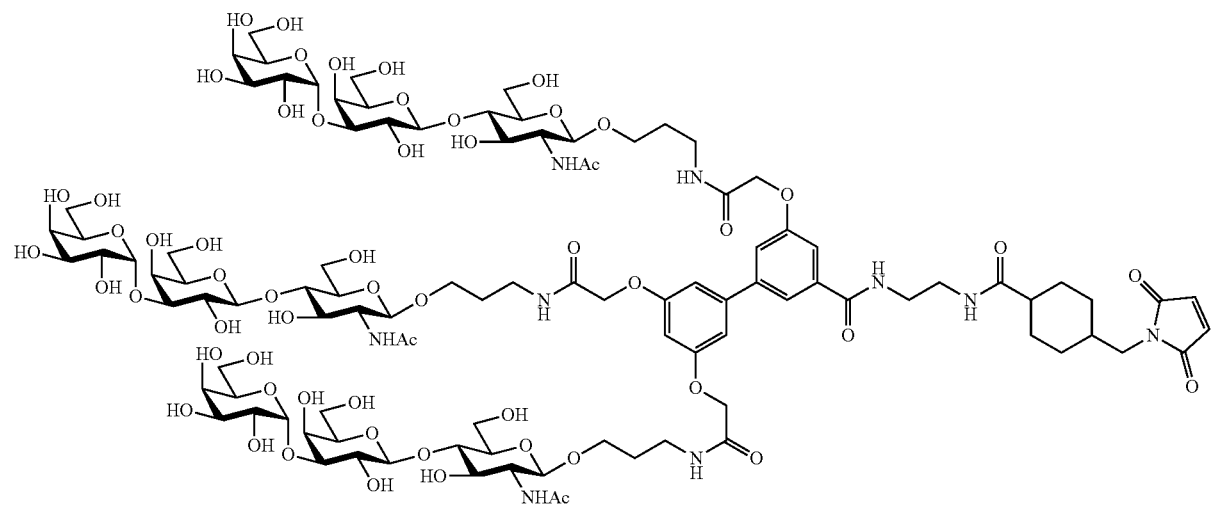

To a solution of 2,2',2''-((5'-((2-aminoethyl)carbamoyl)-[1,1'-biphenyl]-3,3',5-triyl)tris(oxy))tris(N-(3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)acetamide) (Preparation 4, 5.0 mg, 2.26 µmol) in DMSO (400 µL) was added a solution of SMCC (0.69 mg, 2.05 µmol) in DMSO (100 µL). The resulting solution was stirred at toom temperature for 18 hours and then dried under vacuum. The crude residue was taken on directly to the next step.

LCMS Method B: Rt=1.57 mins, ES+ MS m/z 1218.5 [M+2H]+/2, theoretical mass: 2435.4

Preparation 3

4'-(2-((3-(((2R,3R,4R,5S,6R)-3-Acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-N-(2-aminoethyl)-[1,1'-biphenyl]-3-carboxamide

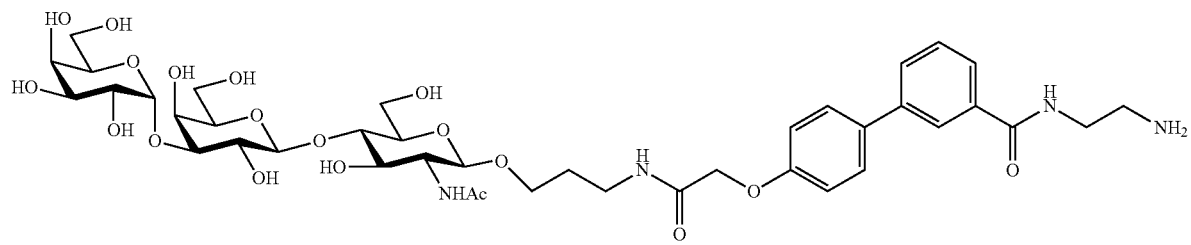

Step 1

To a solution of 4'-(2-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-[1,1'-biphenyl]-3-carboxylic acid (Preparation 6, 38.3 mg, 44.7 µmol) in DMF (0.5 mL) was added Et₃N (21.8 µL, 156.4 µmol) followed by a solution of N¹-((4-methoxyphenyl)diphenylmethyl)ethane-1,2-diamine (Preparation 19, 19.3 mg, 58.1 µmol) in DMF (0.5 mL). The reaction was stirred at room temperature for 1.5 hours.

Step 2

0.2 M HCl (aq) was added dropwise until pH 3-4 and the solution was stirred for 18 hours at room temperature. The reaction was concentrated in vacuo and purified using reverse phase column chromatography eluting with 5-40% MeCN in water with 0.1% ammonia to afford the title compound as a colourless solid (12.4 mg, 28%).

LCMS Method B: Rt=1.32 mins, ES+ MS m/z 899.3 [M+H]+

Preparation 4

2,2',2''-((5'-((2-Aminoethyl)carbamoyl)-[1,1'-biphenyl]-3,3',5-triyl)tris(oxy))tris(N-(3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)acetamide)

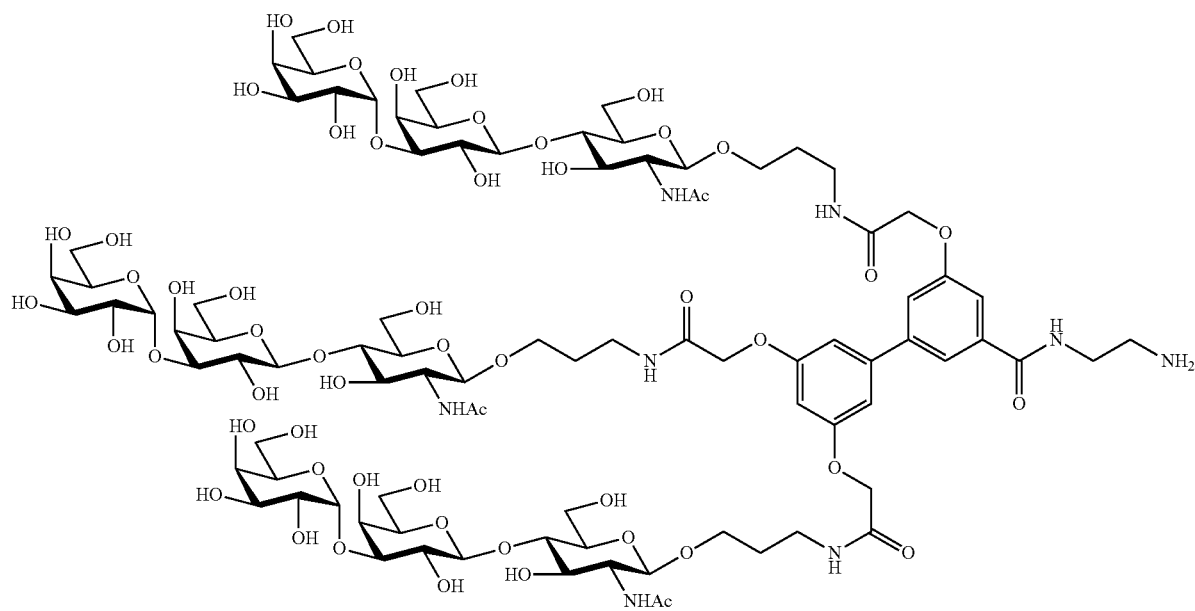

Step 1

To a solution of 3',5,5'-tris(2-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-[1,1'-biphenyl]-3-carboxylic acid (Preparation 5, 66.0 mg, 30.4 μmol) in DMF (0.5 mL) was added Et$_3$N (14.8 μL, 106.4 μmol) followed by a solution of $N^1$-((4-methoxyphenyl)diphenylmethyl)ethane-1,2-diamine (Preparation 19, 13.1 mg, 39.5 μmol) in DMF (0.5 mL). The reaction was stirred at room temperature for 1.5 hours.

Step 2

0.2 M HCl (aq) was added dropwise until pH 3-4 and the solution was stirred for 18 hours at room temperature. The reaction was concentrated in vacuo and purified using reverse phase column chromatography eluting with 5-40% MeCN in water with 0.1% ammonia to afford the title compound as a colourless solid (47.0 mg, 70%).

LCMS Method B: Rt=1.57 mins, ES$^+$ MS m/z 1106.9 [M+2H]$^+$/2, theoretical mass: 2216.1

Preparation 5

3',5,5'-Tris(2-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-[1,1'-biphenyl]-3-carboxylic acid

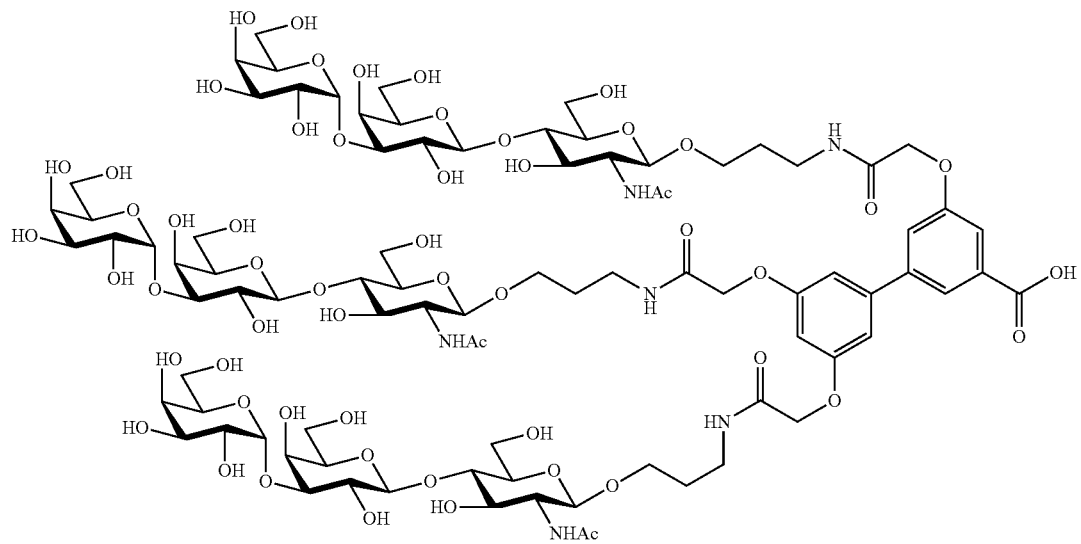

Method A

To benzyl 3',5,5'-tris(2-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-[1,1'-biphenyl]-3-carboxylate (Preparation 7, 71.2 mg, 31.4 μmol) dissolved in MeOH/water (1:1 v/v, 7.1 mL) was added 10% Pd/C (7.1 mg). The reaction was hydrogenated at 50 psi with stirring for 3 hours at room temperature. The reaction was filtered through Dicalite and concentrated in vacuo. The residue was dissolved in water (2 mL), stirred with SiliCycle DMT resin (50 mg) for 30 minutes and filtered to afford a colourless solution. The solution was concentrated in vacuo to afford the title compound as a colourless solid (61.2 mg, 89%).

LCMS Method B: Rt=1.27 mins, ES$^+$ MS m/z 1088.4 [M+2H]$^+$/2, theoretical mass: 2174.4 MALDI-ToF 2195.8 [M−H+Na]$^+$ Preparation 3 may also be prepared according to the following Method

Method B

To benzyl 3',5,5'-tris(2-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-[1,1'-biphenyl]-3-carboxylate (Preparation 7, 278 mg, 123 μmol) dissolved in water (7 mL) was added TEA (7 mL) and the reaction was stirred vigorously for 16 hours at room temperature. The reaction was concentrated in vacuo and purified using reverse phase column chromatography eluting with 5-40% MeCN/water with 0.1% NH₃ to afford the title compound as a colourless solid (224 mg, 83%).

Preparation 6

4'-(2-((3-(((2R,3R,4R,5S,6R)-3-Acetamido-5-(((2S, 3R,4S,5S,6R)-3,5-dihydroxy-6-(hydroxymethyl)-4- (((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl) tetrahydro-2H-pyran-2-yl)oxy)propyl)amino)-2-oxoethoxy)-[1,1'-biphenyl]-3-carboxylic acid

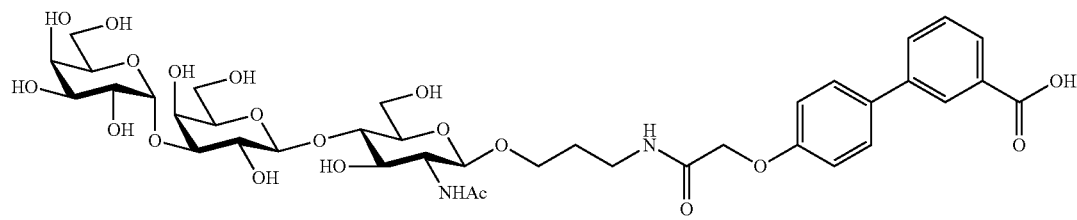

To benzyl 4'-(2-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-[1,1'-biphenyl]-3-carboxylate (Preparation 8, 93.5 mg, 98.7 µmol) dissolved in MeOH/water (1:1 v/v, 5 mL) was added Pd/C (10%, 10 mg). The reaction was put under an atmosphere of hydrogen (50 psi) and stirred for 3 hours at room temperature. The catalyst was removed by filtration through a syringe filter and the solvent removed under reduced pressure to give the crude product which was purified using reverse phase column chromatography eluting with 5-40% MeCN/water with 0.1% NH₃ to afford the title compound as a colourless solid (71.6 mg 84%).

LCMS Method A: Rt=1.83 mins, ES⁺ MS m/z 857.57 [M+H]⁺

Preparation 7

Benzyl 3',5,5'-tris(2-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-[1,1'-biphenyl]-3-carboxylate

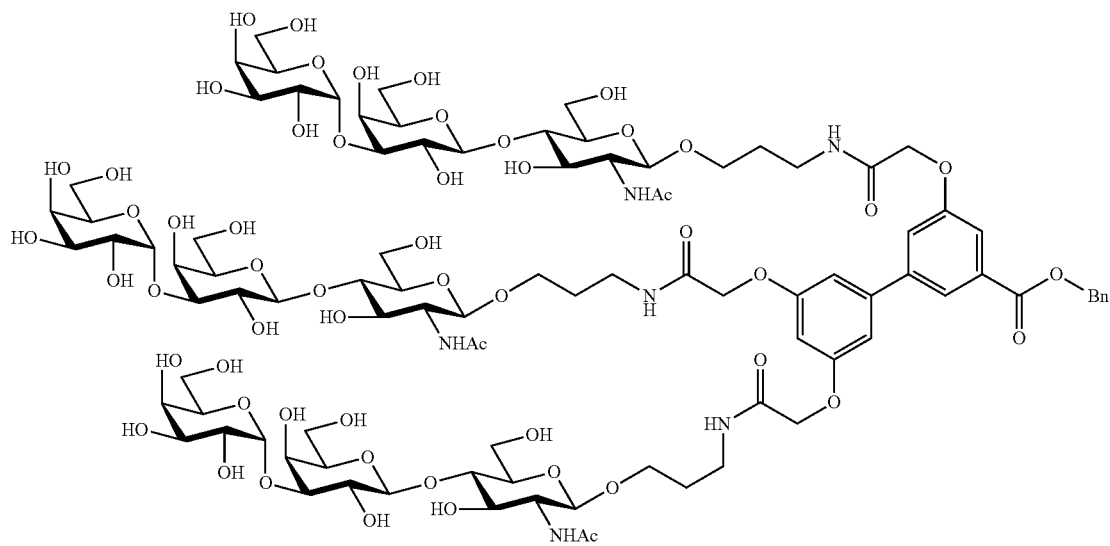

To alpha-Gal (100 mg, 166 μmol) dissolved in DMSO (1.25 mL) and DMF (3.75 mL) was added triethylamine (52.1 μL, 374 μmol) and 2,2',2"-((5'-((benzyloxy)carbonyl)-[1,1'-biphenyl]-3,3',5-triyl)tris(oxy))triacetic acid (Preparation 9, 21.2 mg, 41.5 μmol). A solution of HATU (63.1 mg, 166 μmol) was added as a solution in DMF (1.25 mL) was added and the reaction stirred for 16 hours at room temperature under nitrogen. The reaction was concentrated in vacuo and purified using reverse phase column chromatography eluting with 10-40% MeCN in water with 0.1% NH$_3$ to afford the title compound as a colourless solid (71.2 mg, 76%). LCMS Method B: Rt=1.80 mins, ES$^+$ MS m/z 1313.3 [M+2H]$^+$/2, theoretical mass: 2624.3

Preparation 8

Benzyl 4'-(2-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-[1,1'-biphenyl]-3-carboxylate

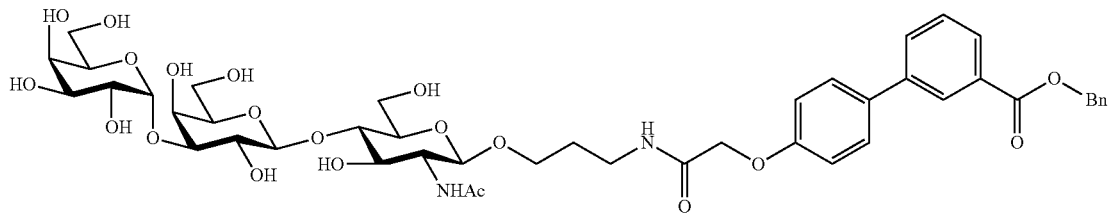

To 2-((3'-((benzyloxy)carbonyl)-[1,1'-biphenyl]-4-yl)oxy)acetic acid (Preparation 10, 55.0 mg, 152 μmol) in DMF (7.5 mL) was added TEA (63.4 μL, 455 μmol) followed by alpha-Gal (119 mg, 197 μmol) in DMSO (500 μL). HATU (86.6 mg, 228 μmol) was added as a solution in DMF (500 μL), and the reaction was left to stir for 16 hours under nitrogen at room temperature. The reaction was concentrated in vacuo and purified using reverse phase column chromatography eluting with 7-60% MeCN/water with 0.1% NH$_3$ to afford the title compound as a colourless solid (93.5 mg, 65%).

LCMS Method B: Rt=2.54 mins, ES$^+$ MS m/z 947.62 [M+H]$^+$

Preparation 9

2,2',2"-((5'-((Benzyloxy)carbonyl)-[1,1'-biphenyl]-3,3',5-triyl)tris(oxy))triacetic acid

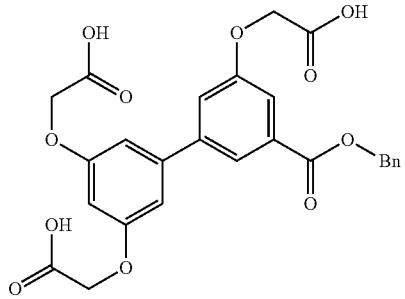 [SMILES: O=C(O)COc1cc(OCC(=O)O)cc(-c2cc(OCC(=O)O)cc(C(=O)OCc3ccccc3)c2)c1]

A solution of tri-tert-butyl 2,2',2"-((5'-((benzyloxy)carbonyl)-[1,1'-biphenyl]-3,3',5-triyl)tris(oxy))triacetate (Preparation 11, 100 mg, 147 μmol) dissolved in DCM/TFA/water (10/10/1 v/v/v, 5 mL) was stirred for 16 hours at room temperature. The reaction was concentrated in vacuo, dissolved in MeOH (1 mL) and precipitated with water (10 mL). The precipitate was collected by filtration, washed with water and dried under vacuum to afford the title compound as a colourless solid (57.8 mg. 77%).

LCMS Method A: Rt=2.48 mins, ES$^-$ MS m/z 509.3 [M–H]$^-$ $^1$H NMR (400 MHz, DMSO-d$_6$): δ ppm 13.05 (3H, br s), 7.90 (1H, s), 7.55-7.45 (3H, m), 7.45-7.30 (4H, m), 6.80 (2H, d), 6.50 (1H, t), 5.40 2H, s), 4.85 (2H, s). 4.75 (4H, s).

Preparation 10

2-((3'-((Benzyloxy)carbonyl)-[1,1'-biphenyl]-4-yl)oxy)acetic acid

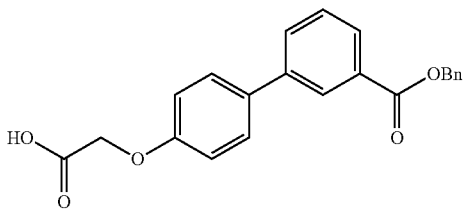 [SMILES: O=C(O)COc1ccc(-c2cccc(C(=O)OCc3ccccc3)c2)cc1]

The title compound was prepared according to the method described for Preparation 9 using Preparation 12 and purified using reverse phase column chromatography eluting with 5-40% MeCN/water with 0.1% NH$_3$.

LCMS Method B: Rt=2.43 mins, ES$^+$ MS m/z 363.2 [M+H]$^+$ $^1$H NMR (400 MHz, DMSO-d$_6$): δ ppm 13.00 (1H, s), 8.15 (1H, t), 7.90-7.85 (2H, m), 7.65-7.55 (3H, m), 7.50-7.45 (2H, m), 7.45-7.30 (3H, m), 7.00-6.95 (2H, m), 5.40 (2H, s), 4.70 (2H, s).

Preparation 11

Tri-tert-butyl 2,2',2''-((5'-((benzyloxy)carbonyl)-[1,1'-biphenyl]-3,3',5-triyl)tris(oxy))triacetate

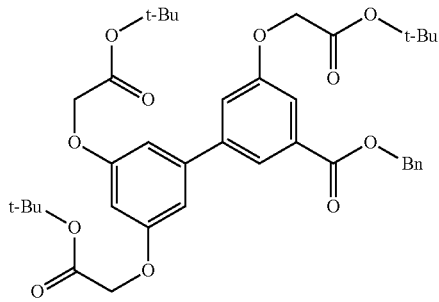 [SMILES: CC(C)(C)OC(=O)COc1cc(OCC(=O)OC(C)(C)C)cc(-c2cc(OCC(=O)OC(C)(C)C)cc(C(=O)OCc3ccccc3)c2)c1]

To benzyl 3',5,5'-trihydroxy-[1,1'-biphenyl]-3-carboxylate (Preparation 13, 356 mg, 1.06 mmol) dissolved in DMF (10 mL) was added tert-butyl bromoacetate (625 μL, 4.23 mmol) and potassium carbonate (1.17 g, 8.47 mmol). The resulting suspension was stirred for 16 hours under nitrogen before concentration in vacuo. The residue was dissolved in water (10 mL) and extracted with EtOAc (2×10 mL). The combined organic layers were washed with brine (10 mL), 2M aqueous NaOH (10 mL), dried over MgSO$_4$ and concentrated in vacuo. The residue was purified using silica gel column chromatography eluting with 7-60% EtOAc in heptane to afford the title compound as a clear colourless gum (618 mg, 86%).

LCMS Method C: Rt=4.34 mins, no mass ion observed $^1$H NMR (400 MHz, CDCl$_3$): δ ppm 7.85 (1H, s), 7.55-7.50 (1H, m), 7.45-7.25 (6H, m), 6.70 (2H, d), 6.45-6.40 (1H, m), 5.35 (2H, s), 4.55 (2H, s), 4.50 (4H, s), 1.45 (27H, s)

Preparation 12

Benzyl 4'-(2-(tert-butoxy)-2-oxoethoxy)-[1,1'-biphenyl]-3-carboxylate

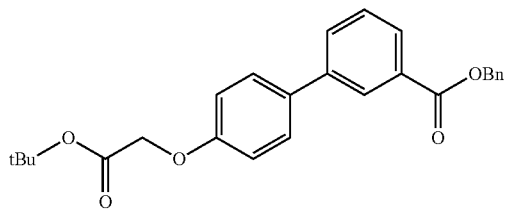 [SMILES: CC(C)(C)OC(=O)COc1ccc(-c2cccc(C(=O)OCc3ccccc3)c2)cc1]

To a solution of benzyl 4'-hydroxy-[1,1'-biphenyl]-3-carboxylate (Preparation 14, 368 mg, 1.21 mmol) and tert-butyl bromoacetate (178 μL, 1.21 mmol) in DMF (5 mL) was added potassium carbonate (200 mg, 1.45 mmol) and the reaction was stirred at room temperature for 20 hours followed by 50° C. for 2 hours. The reaction was concentrated in vacuo and the resulting residue partitioned between water (20 mL) and DCM (20 mL). The organic layer was separated and the aqueous layer extracted again with DCM (20 mL). The combined organic extracts were washed with water (10 mL), dried over sodium sulphate and concentrated in vacuo. The residue was purified by silica gel column chromatography eluting with 0-15% EtOAc in hexane to afford the title compound as an oil (510 mg, 100%).

LCMS Method D: Rt=3.85 mins, no mass ion observed $^1$H NMR (400 MHz, CDCl$_3$): δ ppm 8.25 (1H, t), 8.01-7.99 (1H, dt), 7.76-7.71 (1H, m), 7.58-7.31 (8H, m), 7.06-6.95 (2H, m), 5.39 (2H, s), 4.56 (2H, s), 1.50 (9H, s).

Preparation 13

Benzyl 3',5,5'-trihydroxy-[1,1'-biphenyl]-3-carboxylate

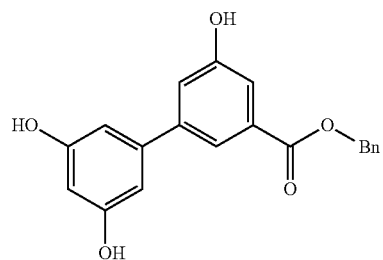 [SMILES: O=C(OCc1ccccc1)c1cc(O)cc(-c2cc(O)cc(O)c2)c1]

To a solution of crude benzyl 3',5'-bis((tert-butyldimethylsilyl)oxy)-5-hydroxy-[1,1'-biphenyl]-3-carboxylate (Preparation 16, 1.27 g, 2.46 mmol) dissolved in THF (12 mL) was added TBAF solution (1M in THF, 6.15 mL, 6.15 mmol) dropwise. The reaction was stirred at room temperature under nitrogen for 90 minutes before diluting with EtOAc (100 mL). The organic phase was washed with water (2×50 mL), dried over MgSO$_4$ and concentrated in vacuo. The residue was purified using silica gel column chromatography eluting with 5% MeOH in DCM to afford the title compound as a pale brown solid (356 mg, 43% over 3 steps).

LCMS Method A: Rt=2.66 mins, ES$^-$ MS m/z 335.3 [M−H]$^-$ $^1$H NMR (400 MHz, CD$_3$OD): δ ppm 7.60 (1H, t), 7.45-7.40 (2H, m), 7.40-20 (4H, m), 7.15-7.10 (1H, m), 6.45 (2H, d), 6.20 (1H, t), 5.30 (2H, s).

Preparation 14

Benzyl 4'-hydroxy-[1,1'-biphenyl]-3-carboxylate

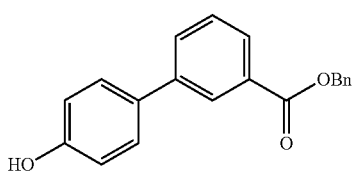 [SMILES: O=C(OCc1ccccc1)c1cccc(-c2ccc(O)cc2)c1]

To a solution of benzyl chloride (295 µL, 2.56 mmol) in DMF (5 mL) was added 4'-hydroxybiphenyl-3-carboxylic acid (500 mg, 2.33 mmol) and potassium carbonate (322 mg, 2.33 mmol). The reaction mixture was stirred at room temperature for 20 hours before concentrating in vacuo. The residue was partitioned between water (20 mL) and diethyl ether (20 mL). The organic layer was separated and the aqueous layer extracted again with diethyl ether (20 mL). The combined organic extracts were washed with water (10 mL), dried over sodium sulphate and concentrated in vacuo. The residue was purified by silica gel column chromatography eluting with 0-30% EtOAc in hexane to afford the title compound as a white solid (378 mg, 53%).

LCMS Method D: Rt=3.48 mins, ES$^+$ MS m/z 305.0 [M+H]$^+$ $^1$H NMR (400 MHz, CDCl$_3$): δ ppm 8.26-8.24 (1H, m), 8.03-7.98 (1H, m), 7.75-7.71 (1H, m), 7.51-7.43 (5H, m), 7.42-7.31 (3H, m), 6.95-6.90 (2H, m), 5.40 (2H, s).

Preparation 15

Benzyl 3-bromo-5-hydroxybenzoate

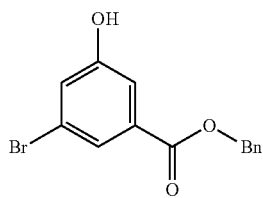 [SMILES: O=C(OCc1ccccc1)c1cc(O)cc(Br)c1]

To a solution of 3-bromo-5-hydroxybenzoic acid (4.08 g, 18.8 mmol) dissolved in DMF (25 mL) was added K$_2$CO$_3$ (2.60 g, 18.8 mmol) and after 5 minutes benzyl bromide (2.24 mL, 18.8 mmol) was added dropwise over 10 minutes. The reaction was stirred at room temperature under nitrogen for 16 hours. Additional K$_2$CO$_3$ (520 mg, 3.76 mmol) and benzyl bromide (450 µL, 3.79 mmol) were added and the reaction stirred for 3 hours. The reaction was concentrated in vacuo and the residue was partitioned between EtOAc (30 mL) and water (30 mL). The aqueous layer was extracted with EtOAc (2×20 mL) and the combined organic layers washed with brine (30 mL). The organic layer was dried over MgSO$_4$ and concentrated in vacuo. The residue was purified by silica gel column chromatography eluting with 5% EtOAc in heptane to afford the title compound as a colourless solid (3.88 g, 67%).

LCMS Method A: Rt=3.36 mins, ES$^-$ MS m/z 307.2 [M−H]$^-$ $^1$H NMR (400 MHz, CDCl$_3$): δ ppm 7.75 (1H, t), 7.50-7.45 (1H, m), 7.45-7.30 (5H, m), 7.20 (1H, t), 5.30 (2H, s), 5.30 (1H, br s).

Preparation 16

Benzyl 3',5'-bis((tert-butyldimethylsilyl)oxy)-5-hydroxy-[1,1'-biphenyl]-3-carboxylate

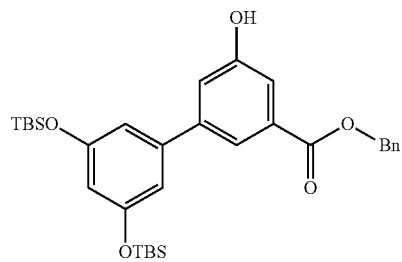 [SMILES: CC(C)(C)[Si](C)(C)Oc1cc(O[Si](C)(C)C(C)(C)C)cc(-c2cc(O)cc(C(=O)OCc3ccccc3)c2)c1]

A mixture of benzyl 3-bromo-5-hydroxybenzoate (Preparation 15, 755 mg, 2.46 mmol), sodium carbonate (912 mg, 8.60 mmol) and ((5-(4,4,5,5-tetramethyl-1,3,2-dioxaborolan-2-yl)-1,3-phenylene)bis(oxy))bis(tert-butyldimethylsilane) (Preparation 17, 1.87 g, 2.95 mmol) dissolved in dioxane/water (30 mL, 5:1 v/v) was degassed for 30 minutes with nitrogen. Pd(PPh$_3$)$_4$ (284 mg, 246 µmol) was added and the reaction heated to 100° C. for 90 minutes under nitrogen. After cooling to room temperature, EtOAc (100 mL) and water (50 mL) were added. The layers were separated and the aqueous phase was backwashed with EtOAc (2×25 mL). The combined organic phases were dried over MgSO$_4$ and concentrated in vacuo. The residue was treated with heptane (100 mL) and the resulting mixture sonicated for 5 minutes, before filtering to remove the solid. The filtrate was concentrated in vacuo to afford the crude title compound as a clear brown oil (1.27 g) that was used directly in the next step.

LCMS Method C: Rt=5.47 mins, ES$^+$ MS m/z 565.4 [M+H]$^+$

Preparation 17

((5-(4,4,5,5-Tetramethyl-1,3,2-dioxaborolan-2-yl)-1,3-phenylene)bis(oxy))bis(tert-butyldimethylsilane)

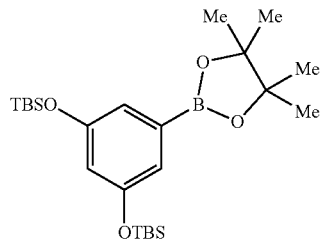 [SMILES: CC1(C)OB(c2cc(O[Si](C)(C)C(C)(C)C)cc(O[Si](C)(C)C(C)(C)C)c2)OC1(C)C]

A solution of 1,3-bis((tert-butyldimethylsilyl)oxy)benzene (Preparation 18, 1.00 g, 2.95 mmol and bis(pinacolato)diboron (750 mg, 2.95 mmol) dissolved in isohexane (15 mL) were degassed for 1 hour using nitrogen. [Ir(OMe)(COD)]$_2$ (19.6 mg, 59.1 µmol) and 4,4'-di-tert-butyl-2,2'-bipyridine (15.9 mg, 59.0 µmol) were added and the reaction sealed and heated to 110° C. for 16 hours. The reaction was cooled, concentrated in vacuo and used directly in the next step (1.87 g).

LCMS Method C: Rt=6.19 mins, ES⁺ MS m/z 465.4 [M+H]⁺

¹H NMR (400 MHz, CDCl₃): δ ppm 6.85 (2H, d), 6.40 (1H, t), 1.25 (12H, s), 0.95 (18H, s), 0.15 (12H, s).

Preparation 18

1,3-Bis((tert-butyldimethylsilyl)oxy)benzene

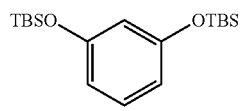 [SMILES: CC(C)(C)[Si](C)(C)Oc1cccc(O[Si](C)(C)C(C)(C)C)c1]

To resorcinol (2.00 g, 18.2 mmol) and imidazole (3.71 g, 54.5 mmol) dissolved in DCM (40 mL) was added tert-butyldimethylchlorosilane (8.21 g, 54.5 mmol). A precipitate formed and further DCM (40 mL) was added, before stirring for 16 hours at room temperature under nitrogen. The reaction was filtered and the filtrate was concentrated in vacuo. The residue was purified using silica gel column chromatography eluting with 0-10% EtOAc in heptane to afford the title compound as a colourless oil (6.18 g, >99%).

LCMS Method C: Rt=5.39 mins, ES⁺ MS m/z 339.3 [M+H]⁺

¹H NMR (400 MHz, CDCl₃): δ ppm 6.95 (1H, t), 6.35 (2H, dd), 6.25 (1H, t), 1.85 (18H, s), 0.10 (12H, s).

Preparation 19

N¹-((4-Methoxyphenyl)diphenylmethyl)ethane-1,2-diamine

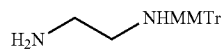

To a solution of ethylene diamine (54.0 mL, 809.6 mmol) in DCM (175 mL) was added slowly a solution of MMT chloride (25.0 g, 81.0 mmol) in DCM (175 mL) over 1 hour with stirring. The resulting solution was stirred at room temperature for 16 hours. The reaction was washed with 10% aqueous potassium carbonate solution (400 mL and brine (400 mL). The organic layer was collected, dried over magnesium sulfate and concentrated in vacuo to afford the title compound as a viscous pale yellow oil (26.1 g, 97%).

LCMS Method B: Rt=2.73 mins, no ionization observed

¹H NMR (400 MHz, CDCl₃): δ ppm 7.52-7.42 (4H, m), 7.40-7.34 (2H, m), 7.31-7.22 (4H, m), 7.20-7.15 (2H, m), 6.84-6.77 (2H, m), 3.80 (3H, s), 2.84-2.78 (2H, m), 2.27-2.18 (2H, m).

Preparation 20

4'-(2-((2-(3-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-3-oxopropoxy)ethyl)amino)-2-oxoethoxy)-N-(2-(3-(2-(2,5-dioxo-2,5-dihydro-1H-pyrrol-1-yl)ethoxy)propanamido)ethyl)-[1,1'-biphenyl]-3-carboxamide

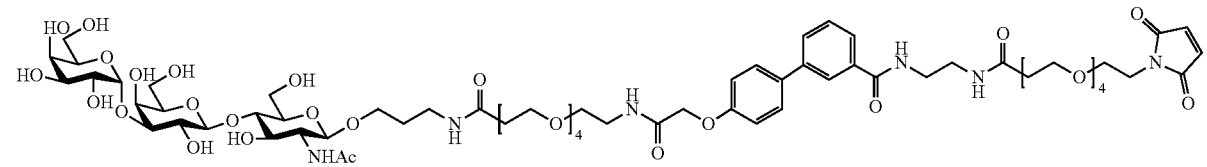

A solution of Preparation 24 in DMF (100 mM) was added to an equal volume of Mal-PEG4-NHS in DMF (80 mM, 0.8 eq) and the reaction was left to stand at room temperature for 2 hours. The reaction was stored as a final concentration of 50 mM and used directly in the conjugation step.

Preparation 21

3,3',3''-((((2,2',2''-((5'-((2-(3-(2-(2,5-dioxo-2,5-di-hydro-1H-pyrrol-1-yl)ethoxy)propanamido)ethyl) carbamoyl)-[1,1'-biphenyl]-3,3',5-triyl)tris(oxy))tris (acetyl))tris(azanediyl))tris(ethane-2,1-diyl))tris (oxy))tris(N-(3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy) propyl)propanamide)

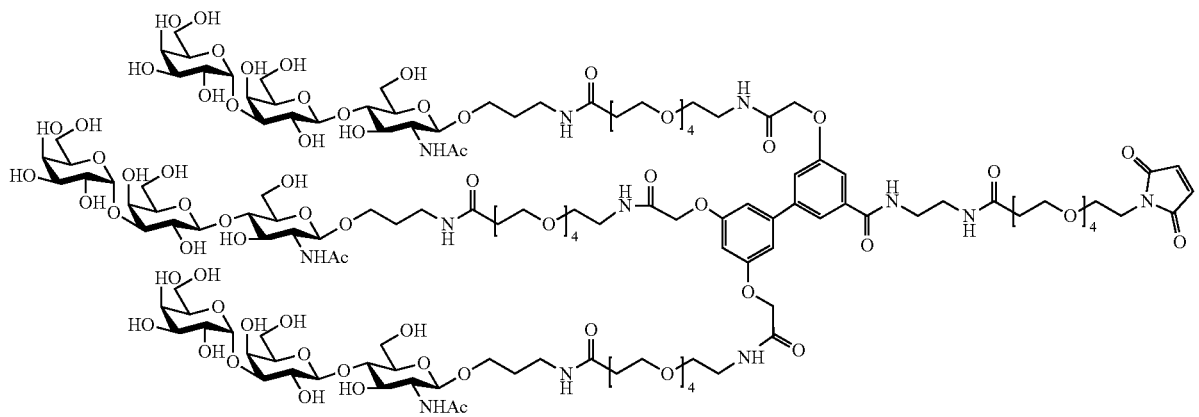

A solution of Preparation 25 in DMF:DMSO (3:1, 25 mM) was added to an equal volume of Mal-PEG4-NHS in DMF (80 mM, 0.8 eq) and the reaction was left to stand at room temperature for 2 hours. The reaction was stored as a final concentration of 20 mM and used directly in the conjugation step.

Preparation 22

2,5-dioxopyrrolidin-1-yl 5-((2-(4'-(2-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-[1,1'-biphenyl]-3-carboxamido)ethyl)amino)-5-oxopentanoate

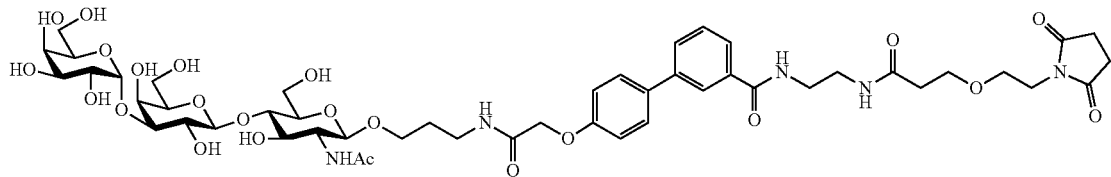

4'-(2-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-N-(2-aminoethyl)-[1,1'-biphenyl]-3-carboxamide (Preparation 3, 21.76 mg, 24 mmol) was dissolved in 1:1 anhydrous DMF:DMSO (1062 µL) with stirring. Di-(N-succinimidyl)glutarate (39.49 mg, 120 mmol) was added as a 300 mM solution in 1:1 anhydrous DMF:DMSO (400 µL). The reaction was stirred for 1 hour at room temperature under a positive nitrogen atmosphere. The reaction was purified using reverse phase column chromatography (10×250 mm Hichrom ACE 10) eluting with 1-50% MeCN in 1% TFA in water. The desired fractions were lyophilised to dryness over 24 hours to afford the title compound as a colourless glass (23 mg, 88%).

MS m/z 1110.3 [M+H]$^+$

Preparation 23

2,5-dioxopyrrolidin-1-yl 5-oxo-5-((2-(3',5,5'-tris(2-((2-(3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-3-oxopropoxy)ethyl)amino)-2-oxoethoxy)-[1,1'-biphenyl]-3-carboxamido)ethyl)amino)pentanoate

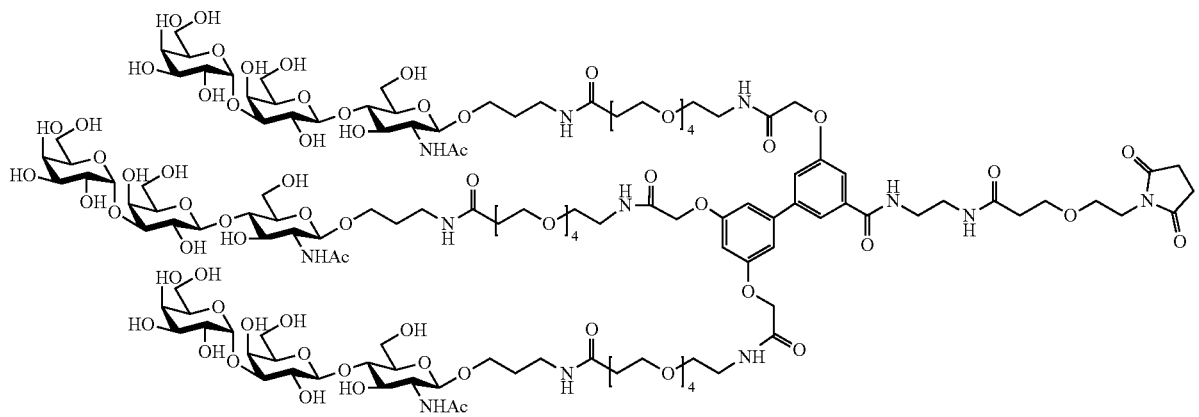

The title compound was prepared according to the method described for Preparation 22 using Preparation 25 and taken directly into the conjugation step.

Preparation 24

4'-(2-((2-(3-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-3-oxopropoxy)ethyl)amino)-2-oxoethoxy)-N-(2-aminoethyl)-[1,1'-biphenyl]-3-carboxamide

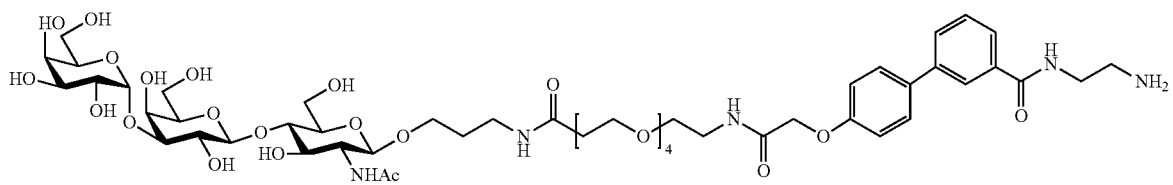

The title compound was prepared according to the method described for Preparation 3 using 4'((2,2-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-2-18-dioxo-6,9,12,15-tetraoxa-3,19-diazadocosyl)oxy)-[1,1'-biphenyl]-3-carboxylic acid (WO2017060729).

LCMS (Method B): Rt=1.66 minutes; ES+ MS m/z 1145.4 [M+H]+

Preparation 25

3,3',3"-(((((2,2',2"-((5'-((2-aminoethyl)carbamoyl)-[1,1'-biphenyl]-3,3',5-triyl)tris(oxy))tris(acetyl))tris(azanediyl))tris(ethane-2,1-diyl))tris(oxy))tris(N-(3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)propanamide)

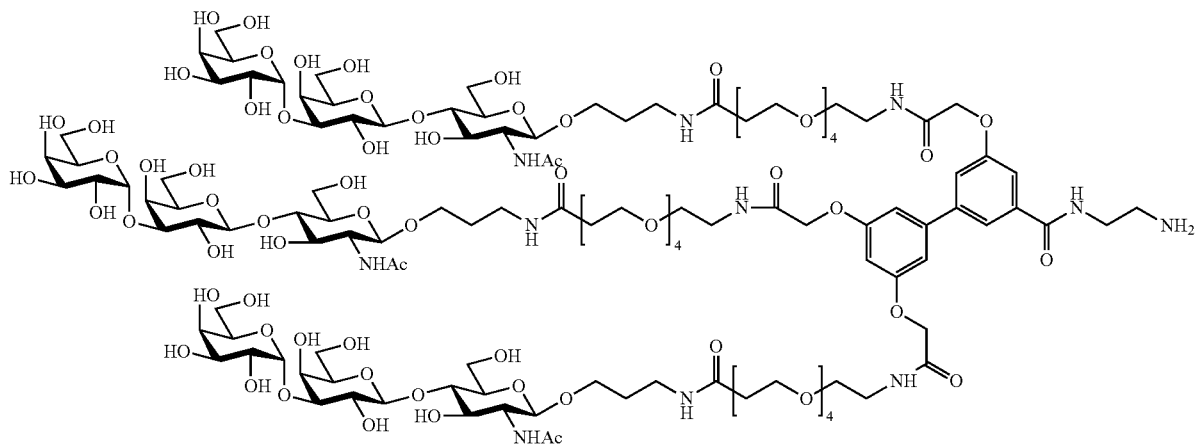

The title compound was prepared according to the method described for Preparation 3 using 3',5,5'-tris((2,2-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)2,18-dioxo-6,9,12,15-tetraoxa-3,19-diazadocosyl)oxy)-[1,1'-biphenyl]-3-carboxylic acid (WO2017060729).

LCMS (Method B): Rt=1.52 minutes; ES+ MS m/z 1479.0 [M+2H]+/2; theoretical mass: 2958.0

EXAMPLES

Materials and Methods:
vcMMAE (vcE): ADCB TOX001, 10 mM in DMA
TCEP—Biovectra Cat 1300 Lot: 42359
N-Acetyl Cysteine—Sigma A7250 Lot: WXBC3104V
Dimethylacetamide—Sigma-Aldrich 271012 Lot: STBF9638V
KNE buffer: 50 mM KPI, 50 mM NaCl, 2 mM EDTA, pH 7.5
PBS: Sigma, P5368 #SLBQ7495, reconstituted using WFI: Sigma W3500 #RNBF6963 1.76 M HEPES, pH 10.8
2-Iminothiolane HCl: Sigma I6256 #SLBS1775V
Polysorbate 80: Sigma-Aldrich P8074 #BCBG4547V
LAR is Linker:Antibody Ratio
DAR is Drug:Antibody Ratio
SEC is size exclusion chromatography Monomer Content by Size Exclusion HPLC (SEC)

The aggregate content of each conjugate was assessed by chromatography on a TOSOH TSKgel G3000SWXL 7.8 mm×30 cm, 5 μm column at 0.5 mL/min in 10% IPA, 0.2M Potassium Phosphate, 0.25M Potassium Chloride, pH 6.95. Samples were loaded neat and data collected at 214, 252 and 280 nm. All reported data are at 280 nm.

Hydrophobic Interaction Chromatography (HIC)

HIC was performed on a TOSOH Butyl-NPR 4.6 mm×3.5 cm, 2.5 μm column at 0.8 mL/min with a 12-minute linear gradient between Mobile Phase A—1.5M $(NH_4)_2SO_4$, 25 mM NaPi, pH 6.95±0.05 and Mobile Phase B—75% 25 mM NaPi, pH 6.95±0.05, 25% IPA. Samples were loaded neat up to a maximum loading of 10 uL and data collected at 280, 252 and 214 nm; all reported data are 214 nm.

Polymeric Reverse Phase Chromatography (PLRP)

Reverse phase was performed on a Polymer Labs PLRP-S 2.1 mm×50 mm, 5 μm, 1000 Å column at 0.25 mL/min/80° C. with a 25-minute linear gradient between 0.1% TFA 25% MeCN and 0.1% TFA 50% MeCN. Samples were reduced by mixing 10 ug with 5 uL 0.1M DTT and making up to 50 uL with 0.5 M Tris/Cl, pH 8.0 and incubating at 37° C. for 15 minutes. Reduced samples were diluted 1:1 with 49% acetonitrile, 49% water, 2% formic acid to stop reduction and stabilize the sample pending PLRP analysis. 20 uL of this sample was loaded onto the column for analysis and all data is reported at 214 nm.

Note: HIC and PLRP are not able to resolve individual linker loadings due to the hydrophilicity of alpha-Gal. The Linker:Ab Ratio (LAR) was determined by vcE chase of an aliquot of the initial thiol-reactive antibody and the completed reaction mixture.

Data for the respective Examples is exemplified in FIGS. 1-3 and 12-17.

Antibody Conjugates (Cetuximab)

Cetuximab (Merck Serono; Lot No: 223155, exp: September 2020, with a molecular weight of 152,000 Da was used for the conjugations below. Calculations were based on an $Abs_{0.1\%}$ 280 nm of 1.45 $cm^{-1}$ $mg/mL^{-1}$, a UV analysis of 4.7 mg/mL and calibration curves by SEC at 214 nm.

General Method for Reduction of Cetuximab Followed by Conjugation to Maleimide Containing Linkers (Examples 1-4)

Cetuximab (4.7 mg/mL) was supplemented with 6% 0.5 M Tris-Cl, 0.025 M EDTA, pH 8.5, and incubated with 1.1 eq TCEP:mAb (for average LAR=2) or 4.2 TCEP:mAb (for average LAR=5) at room temperature for 90 minutes and 120 minutes respectively.

To analyse the extent of reduction, an aliquot of the reduced sample was conjugated with a molar excess of surrogate payload Mal-vc-PAB-MMAE to determine DAR (using HIC analysis).

To the reduced sample was added 8 eq of linker-maleimide and the reaction was incubated for 60 minutes at room temperature. Following incubation, the reaction was quenched by the addition of N-acetyl cysteine (10 mM aqueous solution) for 30 minutes. The samples were purified with G25 resin into PBS and the remaining unbound linker was removed with 10 DIA volumes of membrane diafiltration using Vivaspin6 device.

Example 1

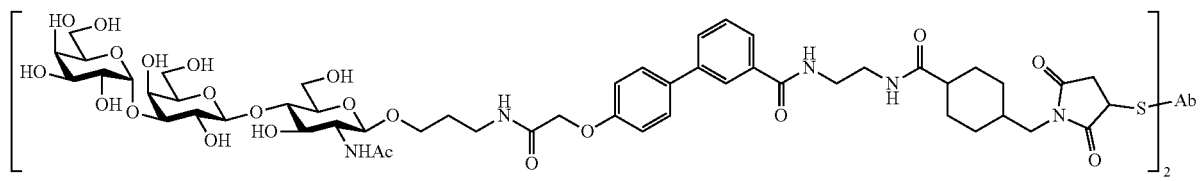

Av. LAR: 2; Av. total no of alpha-Gal units: 2%
Monomer [SEC]: 98.8% (see FIG. 3)
Precursor: Preparation 1

Example 2

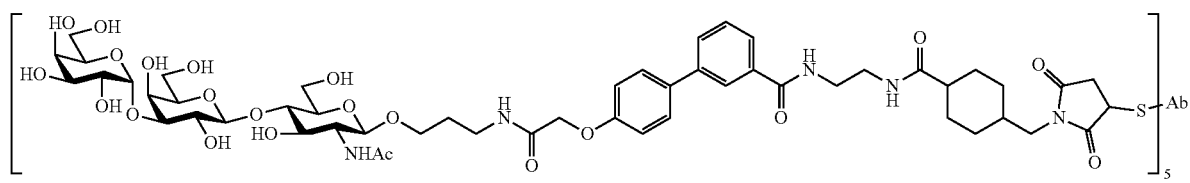

Av. LAR: 5; Av. total no of alpha-Gal units: 5%
Monomer [SEC]: 99.4% (see FIG. 3)
Precursor: Preparation 1

Example 3

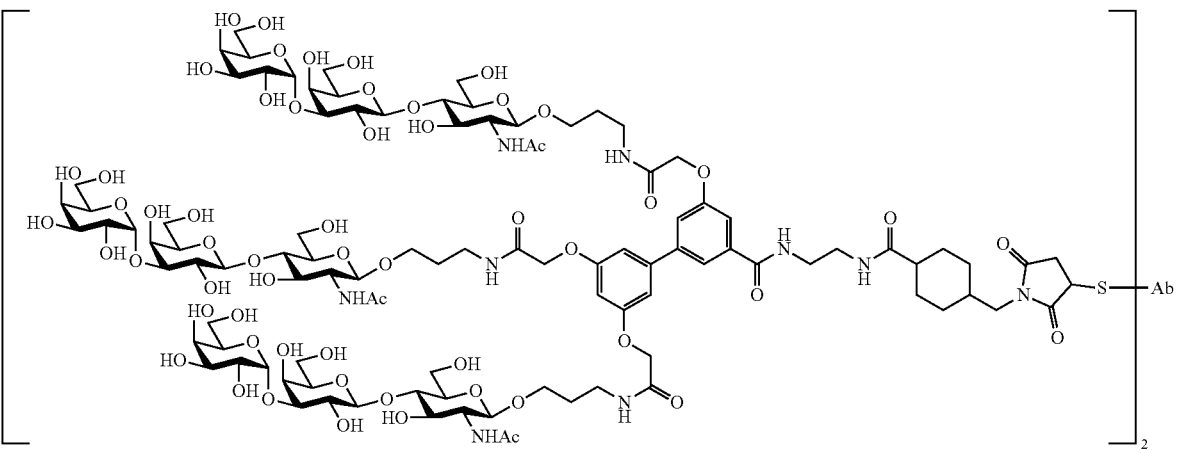

Av. LAR: 2; Av. total no of alpha-Gal units: 6%
Monomer [SEC]: 99.5% (see FIG. 3)
Precursor: Preparation 2

Example 4

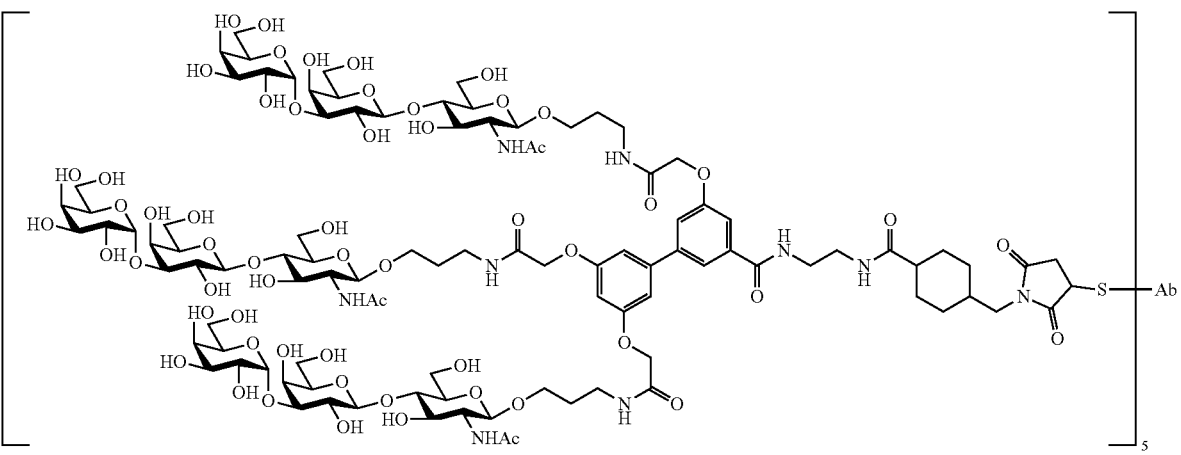

Av. LAR: 5; Av. total no of alpha-Gal units: 15%
Monomer [SEC]: 99.0% (see FIG. 3)
Precursor: Preparation 2

General Method for Interconversion of Cetuximab Lysine to Thiol Followed by Conjugation to Maleimide-Containing Linkers (Examples 5-8)

Cetuximab (4.7 mg/mL) was bound to Protein A resin (GE Healthcare, HiTrap MabSelect SURE 1 mL) then column washed with 50 mM KPI, 50 mM NaCl, 2 mM EDTA, pH 7.5 and the mAb eluted with 4CV 0.1M Glycine at pH 3. The eluted fractions containing the target protein (pooling by UV280 absorbance) were supplemented with 20% 1.76M HEPES at pH 10.8. Cetuximab was then incubated with 12.2 eq 2-iminothiolane:mAb (for low LAR samples) or 30.5 eq 2-iminothiolane:mAb (for high LAR samples) for 120 minutes at 23° C.

An aliquot of the samples was buffer exchanged in 5 mM His, 50 mM Trehalose pH 6.0 and conjugated with a molar excess of surrogate payload Mal-vc-PAB-MMAE to determine DAR. The remaining thiolation mixture was quenched through NAP25 buffer exchange into 5 mM His, 50 mM Trehalose at pH 6.0 prior to coupling. The linker-maleimide conjugation was performed using 4 eq linker-maleimide:thiol with final 5% DMA for 120 minutes at 23° C. Upon incubation, the samples were buffer exchanged into PBS through G25 resin. The excess linker was removed through 10DV membrane diafiltration (Vivaspin6).

The quantity of free thiol can be monitored throughout the experiment using Ellman's assay.
Example 5
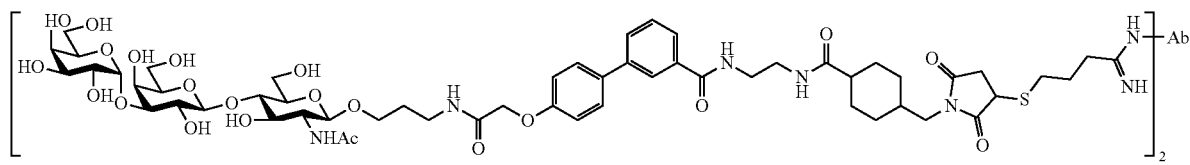
Av. LAR: 2; Av. total no of alpha-Gal units: 2%
Monomer [SEC]: 95.0% (see FIG. 3)
Precursor: Preparation 1
Example 6
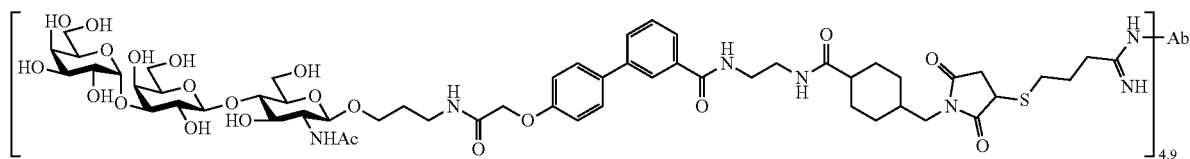
Av. LAR: 4.9; Av. total no of alpha-Gal units: 4.9%
Monomer [SEC]: 90.3% (see FIG. 3)
Precursor: Preparation 1
Example 7
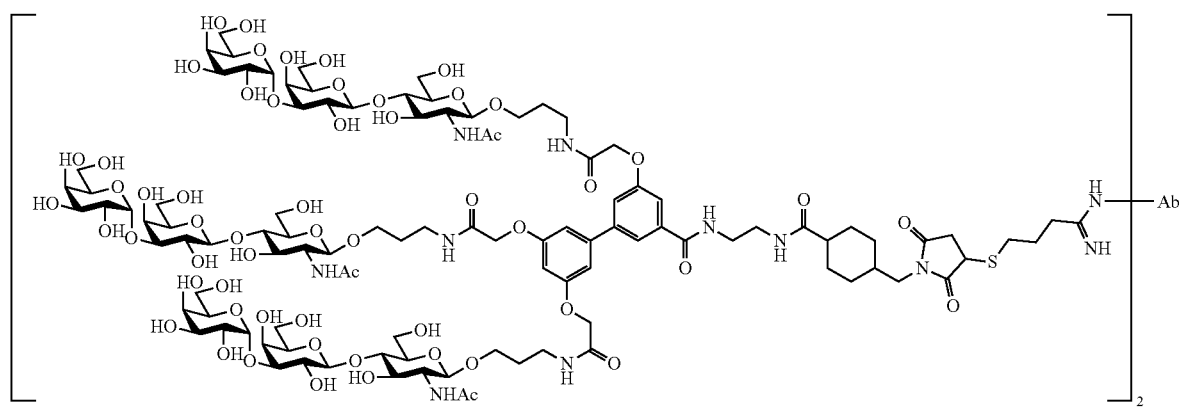

Av. LAR: 2; Av. total no of alpha-Gal units: 6%
% Monomer [SEC]: 90.4% (see FIG. 3)
Precursor: Preparation 2

Example 8

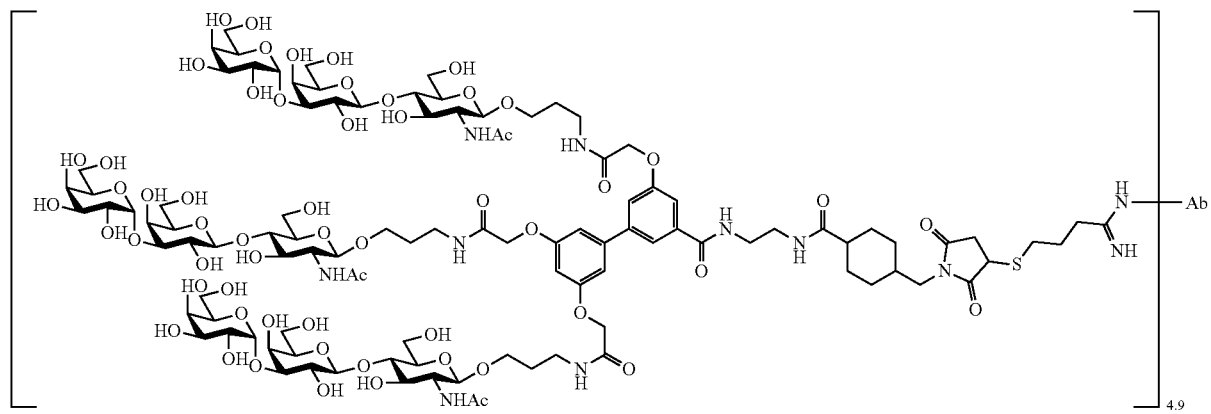

Av. LAR: 4.9; Av. total no of alpha-Gal units: 14.7%
% Monomer [SEC]: 80.8% (see FIG. 3)
Precursor: Preparation 2

General Method for Reduction of Cetuximab Followed by Conjugation to Maleimide-Containing Linkers for Obtaining Average LAR=8 (Examples 9-11)

Cetuximab (4.7 mg/mL) was supplemented with 6% 0.5 M Tris-Cl, 0.025 M EDTA (pH 8.5) to approximately pH=7.5 and incubated with 8 eq TCEP:mAb at room temperature for 90 minutes.

To analyse the extent of reduction, an aliquot of the reduced sample was conjugated with a molar excess of surrogate payload Mal-vc-PAB-MMAE to determine DAR (using HIC analysis).

To the reduced sample was added either 16 or 32 eq of linker-maleimide and the reaction was incubated for 60 minutes at room temperature. Following incubation, the reaction was quenched by the addition of N-acetyl cysteine (10 mM aqueous solution) for 30 minutes and the samples were purified with G25 resin into PBS and the remaining unbound linker was removed with 10 DIA volumes of membrane diafiltration using Vivaspin6 30 kDa PES device.

Example 9

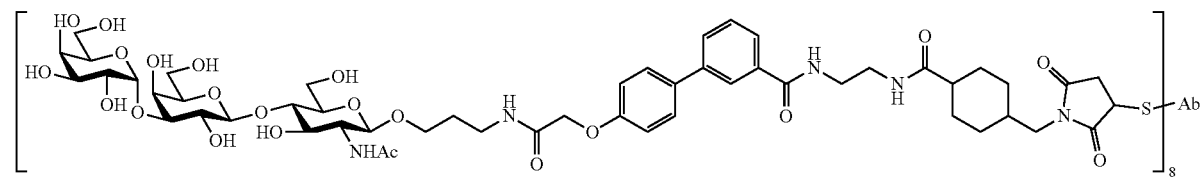

Av. LAR: 8; Av. total no of alpha-Gal units: 8
SEC Analysis: Rt=15.3 minutes, 98.3% monomer content
Precursor: Preparation 1

Example 10

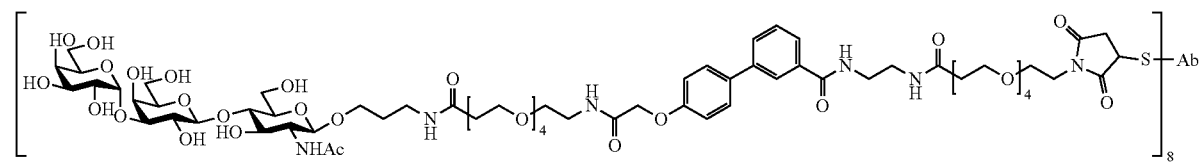

Av. LAR: 8; Av. total no of alpha-Gal units: 8
SEC Analysis: Rt=14.8 minutes, 98.5% monomer content
Precursor: Preparation 20

Example 11

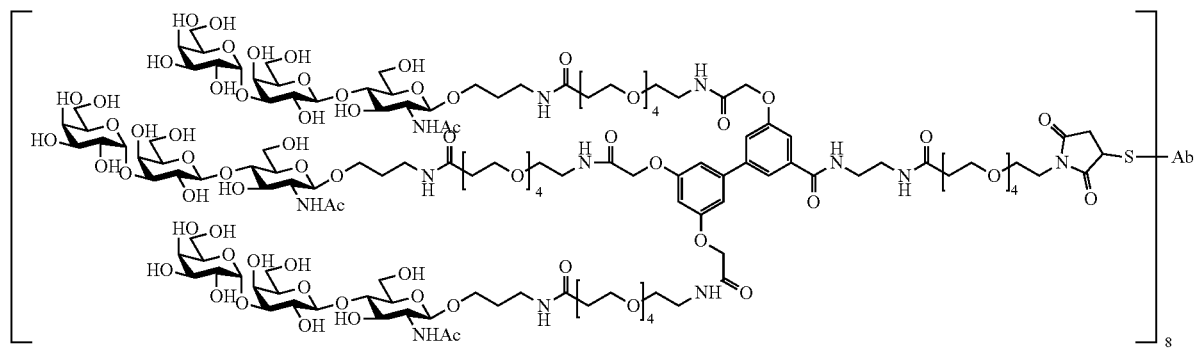

Av. LAR: 8; Av. total no of alpha-Gal units: 8
SEC Analysis: Rt=14.1 minutes, 97.0% monomer content
Precursor: Preparation 21

General Method for Direct Lysine Conjugation of Cetuximab to N-Hydroxysuccinimide Containing Linkers (Examples 12-16)

Cetuximab (20 mg) was bound to Protein A resin (GE Healthcare, HiTrap MabSelect Sure, 1 mL) and column washed with a solution of 50 mM KPi, 50 mM NaCl and 2 mM EDTA at pH=8. The antibody was eluted with 100 mM citrate buffer at pH=3 and buffer exchanged into Lysine conjugation buffer (50 mM NaPi, 150 mM NaCl, 2 mM EDTA, pH=8) with concentration to approximately 6 mg/mL. The solution was analysed by SEC to afford cetuximab in a solution suitable for lysine conjugation (18.2 mg, 91% yield, at 6.4 mg/mL, 100% monomer content).

The above solution of cetuximab was incubated with either 5, 10, 15, 20 or 38 molar equivalents of Preparation 22 with 6% v/v DMF co-solvent for 2 hours at 30° C. The reaction was quenched by the addition of glycine to 1 mM and the conjugates were buffer exchanged into PBS and diafiltered to remove excess linker.

Example 12

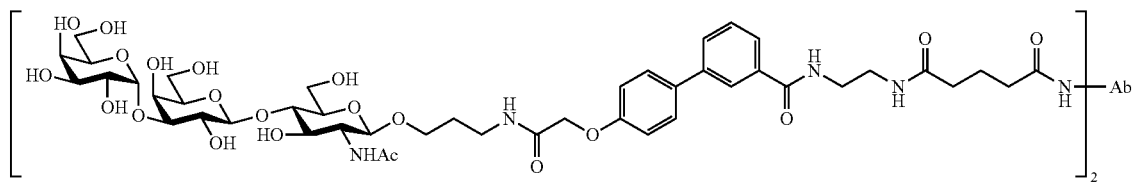

Av. LAR: 2; Av. total no of alpha-Gal units: 2
SEC Analysis: Rt=15.0 minutes. Monomer content not determined.
Precursor: Preparation 22 (5 eq)

Example 13

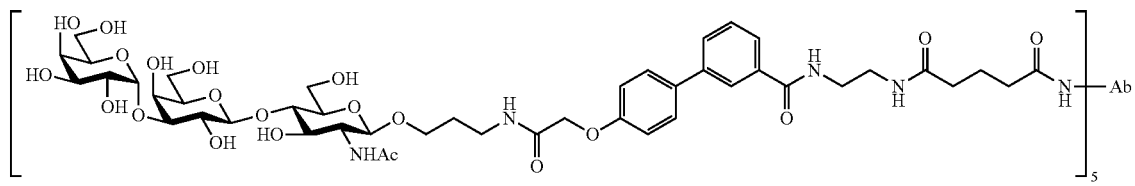

Av. LAR: 5; Av. total no of alpha-Gal units: 5
SEC Analysis: Rt=14.9 minutes. Monomer content not determined.
Precursor: Preparation 22 (10 eq)

Example 14

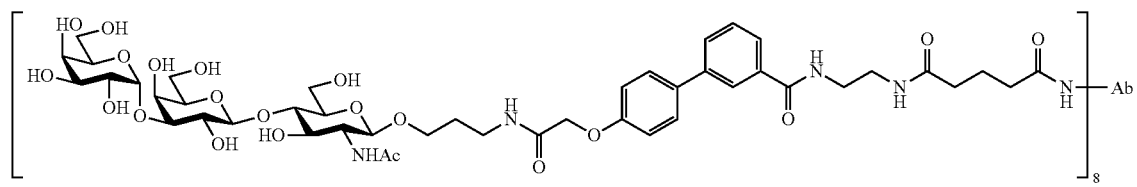

Av. LAR: 8; Av. total no of alpha-Gal units: 8
SEC Analysis: Rt=14.8 minutes. Monomer content not determined.
Precursor: Preparation 22 (15 eq)

Example 15

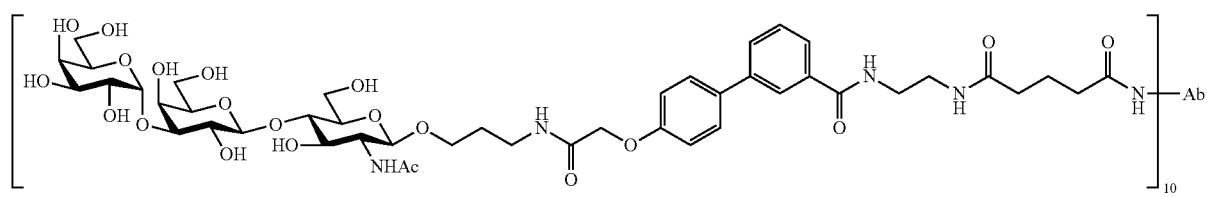

Av. LAR: 10; Av. total no of alpha-Gal units: 10
SEC Analysis: Rt=14.7 minutes. Monomer content not determined.
Precursor: Preparation 22 (20 eq)

Example 16

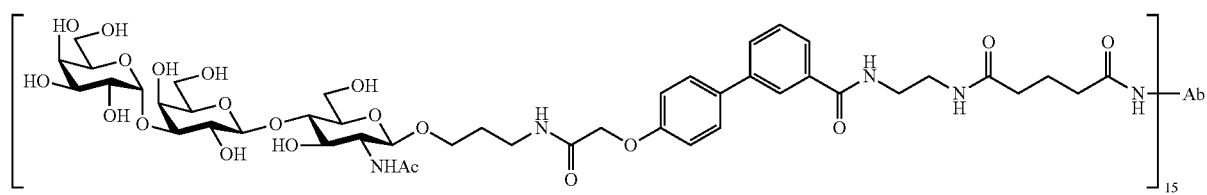

Av. LAR: 15; Av. total no of alpha-Gal units: 15
SEC Analysis: Rt=14.2 minutes, 94.3% monomer content
Precursor: Preparation 22 (38 eq)

Example 17

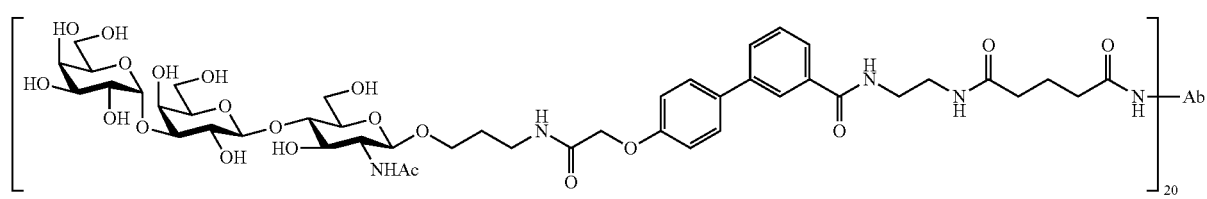

Example 17 was prepared according to General Method 3 using 60 equivalents of Preparation 22 (with 10% v/v DMF) for 2 hours followed by a further 40 eq of Preparation 22 (with 4% v/v DMF) for 2 hours.

Av. LAR: 20; Av. total no of alpha-Gal units: 20
SEC Analysis: Rt=13.9 minutes, 98.4% monomer content
Precursor: Preparation 22

Fab Fragment Conjugates (Cetuximab)

Digestion of Cetuximab to Cetuximab-Fab

Cetuximab (60 mg, 4.7 mg/mL) was buffer exchanged into digestion buffer (20 mM NaPi, 20 mM cysteine, 10 mM EDTA at pH=7) and concentrated to 3 mL at 20 mg/mL. Immobilised papain (3 mL, Thermo Fisher #20341, loading: 250 ug/mL resin, activity: 16-40 BAEE/mg papain) was equilibrated in digestion buffer and incubated with the concentrated cetuximab at 37° C. for 15 hours. The digest products were collected by filtration and eluted through a protein A column. The non-binding Fab fragments passed through the column and the flow through was collected. The Fab fragments were subject to discontinuous diafiltration via vivaspin centrifugation (10 kDa MWCO filter) into 50 mM NaPi, 150 mM NaCl and 2 mM EDTA at pH=8. The final concentration achieved was 5.6 mg/mL (see FIG. 16).

General Method for Reduction of Cetuximab-Fab Followed by Conjugation to Maleimide-Containing Linkers to Obtain LAR=2 (Examples 18 and 19)

Cetuximab-Fab at 5.6 mg/mL in conjugation buffer (50 mM NaPi, 150 mM NaCl and 2 mM EDTA at pH=8) was reduced by the addition of 5 molar equivalents of TCEP (10 mM in water) for 90 minutes at room temperature. A solution of Preparation 20 (5 molar equivalents) or Preparation 21 (7.5 molar equivalents) were added and the reaction incubated for 1 hour at room temperature. The conjugates were buffer exchanged and diafiltered with PBS to afford the desired materials. The conjugates were analysed by SEC and SDS-PAGE.

Example 18

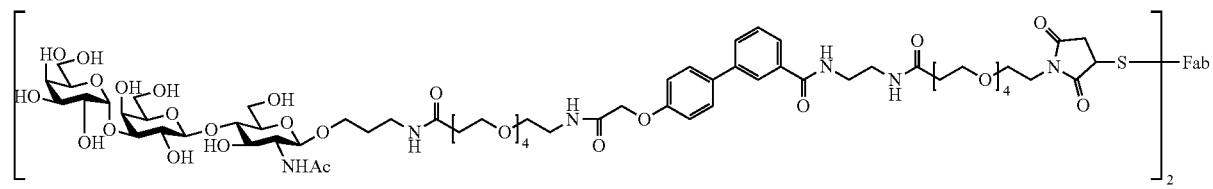

Av. LAR: 2; Av. total no of alpha-Gal units: 2
SEC Analysis: Rt=18.2 minutes, 94.7% monomer content
Precursor: Preparation 20

Example 19

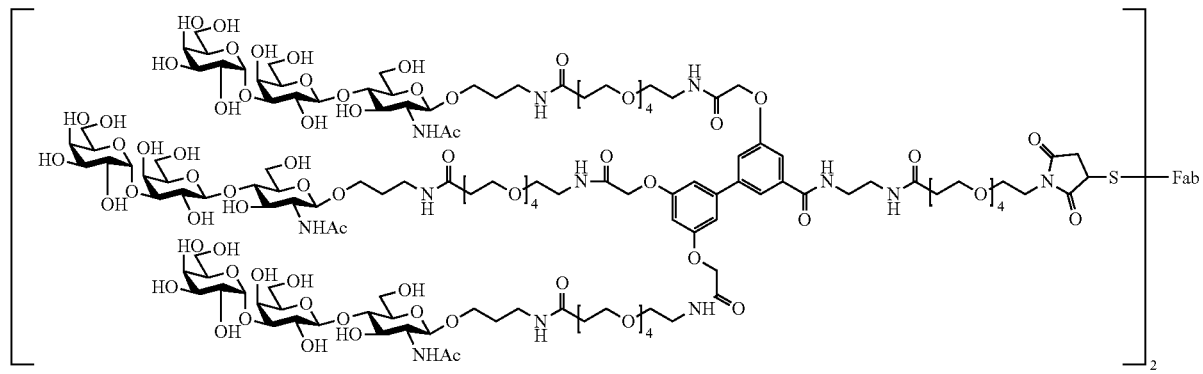

Av. LAR: 2; Av. total no of alpha-Gal units: 6
SEC Analysis: Rt=17.4 minutes, 91.7% monomer content
Precursor: Preparation 21

General Method for Lysine Conjugation of Cetuximab-Fab to NHS-Containing Linkers to Obtain an Average LAR=7-14 (Examples 20-24)

Cetuximab-Fab at 5.6 mg/mL in conjugation buffer (50 mM NaPi, 150 mM NaCl and 2 mM EDTA at pH=8) was incubated with Preparation 22 (15, 30 and 40 equivalents) and Preparation 23 (20 equivalents) with 9% v/v DMF co-solvent at 30° C. for 2 hours. The reaction was quenched by the addition of glycine to 1 mM concentration and the conjugates were buffer exchanged into PBS and diafiltered to remove excess linker.

Example 20

Av. LAR: 7; Av. total no of alpha-Gal units: 7
SEC Analysis: Rt=18.0 minutes, 99% monomer content
Precursor: Preparation 22 (15 eq)

Example 21

Av. LAR: 5; Av. total no of alpha-Gal units: 15
SEC Analysis: Rt=17.4 minutes, 99% monomer content
Precursor: Preparation 23 (20 eq)

Example 22

Av. LAR: 11; Av. total no of alpha-Gal units: 11
SEC Analysis: Rt=17.3 minutes, 96.9% monomer content
Precursor: Preparation 22 (30 eq)

Example 23

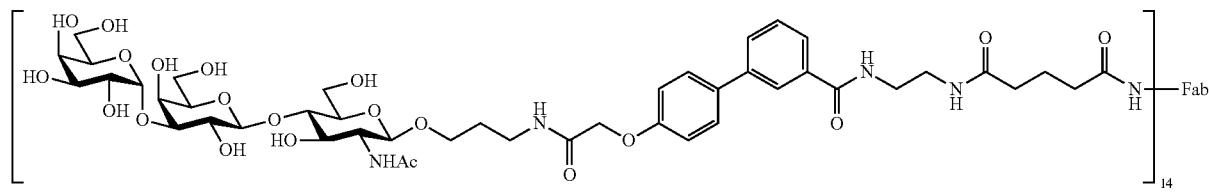

Av. LAR: 14; Av. total no of alpha-Gal units: 14
SEC Analysis: Rt=17.1 minutes, 95.7% monomer content
Precursor: Preparation 22 (40 eq)

Example 24

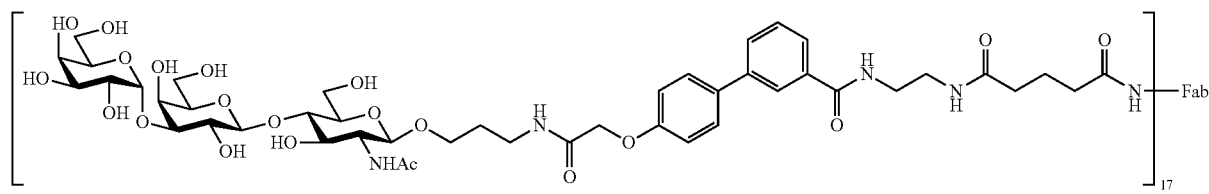

Example 24 was prepared according to General Method 4 using 60 equivalents of Preparation 22 (with 20% v/v DMF) for 2 hours followed by a further 40 eq of Preparation 22 (with 4% v/v DMF) for 2 hours.

Av. LAR: 17; Av. total no of alpha-Gal units: 17

SEC Analysis: Rt=15.9 minutes, 90.2% monomer content

Precursor: Preparation 22 (60+40 eq)

Antibody Conjugates (Rituximab)

Rituximab (Roche-Rituxan, Lot No: B6105B92UI) formulated in polysorbate 80 (0.7 mg/mL) with sodium citrate dehydrate (7.35 mg/mL) sodium chloride (9 mg/mL) and water.

General Method for Direct Lysine Conjugation of Rituximab to N-Hydroxysuccinimide Containing Linkers (Example 25)

Rituximab was pH adjusted to pH=7.9 with 500 mM phosphate buffer (50 mM NaPi, 150 mM NaCl, 2 mM EDTA, pH=8).

The above solution of rituximab was incubated with 40 molar equivalents of Preparation 22 with 10% v/v DMF co-solvent for 2 hours at 30° C. followed by a second addition of 40 molar equivalents of Preparation 22 (with 4% v/v DMF). The reaction was quenched by the addition of glycine to 1 mM and the conjugates were buffer exchanged into PBS and diafiltered to remove excess linker.

Example 25

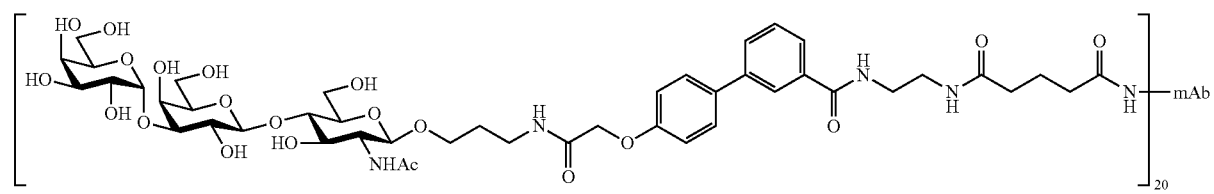

Av. LAR: 20; Av. total no of alpha-Gal units: 20
SEC Analysis: Rt=14.4 minutes, 98.5% monomer content
Precursor: Preparation 22
Fab Fragment Conjugates (Rituximab)
Digestion of Rituximab to Rituximab-Fab Rituximab (60 mg, 4.7 mg/mL) was buffer exchanged into digestion buffer (20 mM NaPi, 20 mM cysteine, 10 mM EDTA at pH=7) and concentrated to 20 mg/mL. Immobilised papain (w/w 1/160, Thermo Fisher #20341, loading: 250 ug/mL resin, activity: 16-40 BAEE/mg papain) was equilibrated in digestion buffer and incubated with the concentrated rituximab at 37° C. for 5-18 hours. The digest products were collected by filtration and eluted through a protein A column. The non-binding Fab fragments passed through the column and the flow through was collected. The Fab fragments were subject to discontinuous diafiltration via vivaspin centrifugation (10 kDa MWCO filter) into 50 mM NaPi, 150 mM NaCl and 2 mM EDTA at pH=8. The final concentration achieved was 11.7 mg/mL.

The above solution of rituximab-Fab was incubated with 40 molar equivalents of Preparation 22 with 25% v/v DMF co-solvent for 2 hours at 30° C. followed by a second addition of 40 molar equivalents of Preparation 22 (with 9% v/v DMF). The reaction was quenched by the addition of glycine to 1 mM and the conjugates were buffer exchanged into PBS and diafiltered to remove excess linker.

Example 26

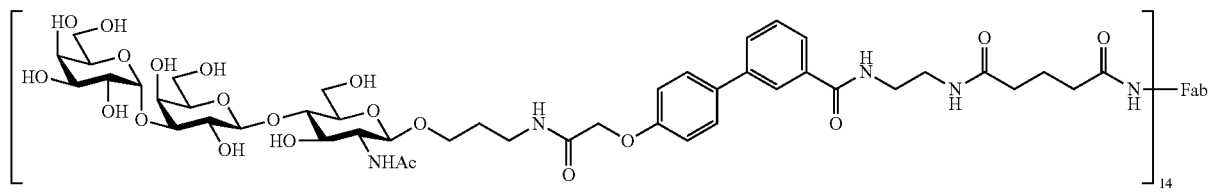

Av. LAR: 14; Av. total no of alpha-Gal units: 14
SEC Analysis: Rt=16.9 minutes, 87.5% monomer content
Precursor: Preparation 22

Flow Cytometry Assay Using Alpha-Galactosyl IgM Antibody

Flow cytometry was used to demonstrate binding of L (as cetuximab) to a receptor on a human cell line and F (as the carbohydrate molecule capable of binding to a human anti-alpha-galactosyl antibody). A431 cells are used to capture the EGFR binding mAb (cetuximab) as it is well known that the cells significantly over-express the EGFR receptor. A secondary phycoerythrin (PE) labelled anti-human IgM antibody was used to detect binding of the alpha-galactosyl IgM antibody to the compound.

A431 cells (ATCC CRL-1555) were harvested and resuspended at $5 \times 10^6$ cells/mL in phosphate buffered saline (PBS) (Sigma D8662)+0.1% BSA (Bovine Serum Albumin—Sigma A2153). $5 \times 10^5$ cells were then incubated with compound at various concentrations as described below or buffer alone at room temperature, shaking at 450 rpm for 1 hour.

The cells were washed with 2×200 µL PBS+0.1% BSA, prior to adding 50 µL of an Anti-alpha galactosyl IgM antibody (Absolute Antibody Ab00532-15.0) at 32 µg/mL in PBS+0.1% BSA and incubating at 4° C. for 1 hour. The cells were further washed with 2×200 µL PBS+0.1% BSA before being treated with 100 µL 1:40 dilution of Anti-Human IgM-PE (Biolegend 314508) at 4° C. for 1 hour. After a final wash of 2×200 µL PBS+0.1% BSA the cells were resuspended in 200 µL PBS+0.1% BSA and evaluated on a flow cytometer (FC500 Beckman Coulter). Data from all samples were analysed in the Kaluza software package (Beckman Coulter).

Figure 4:
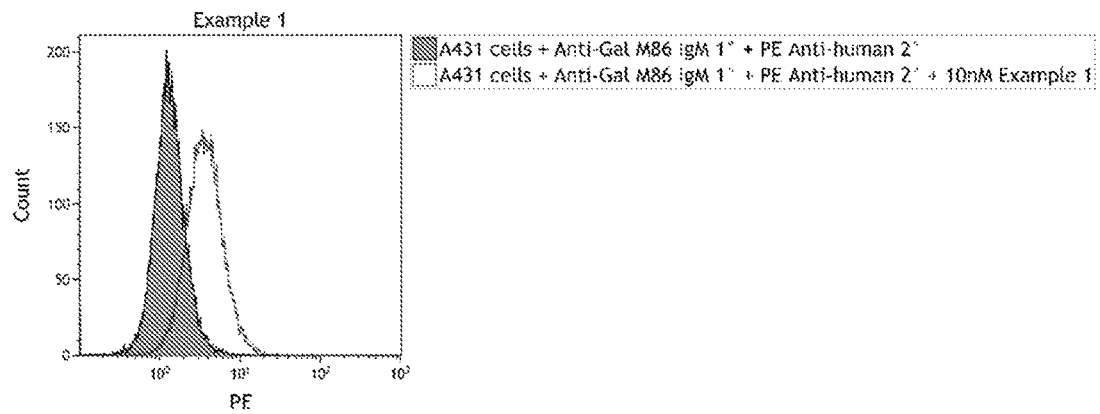
FIG. 4: M86 IgM data for the compounds of Examples 1-8.
Figure 4:
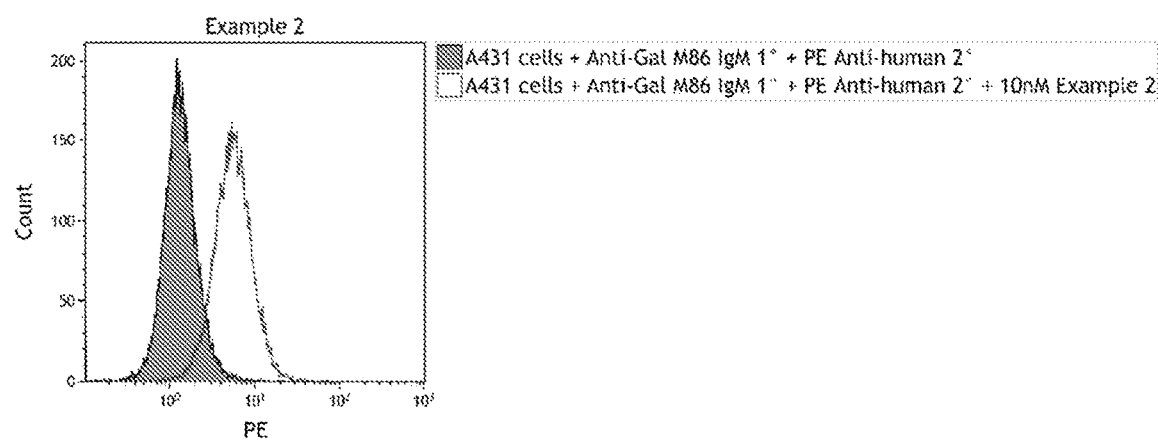
Figure 4:
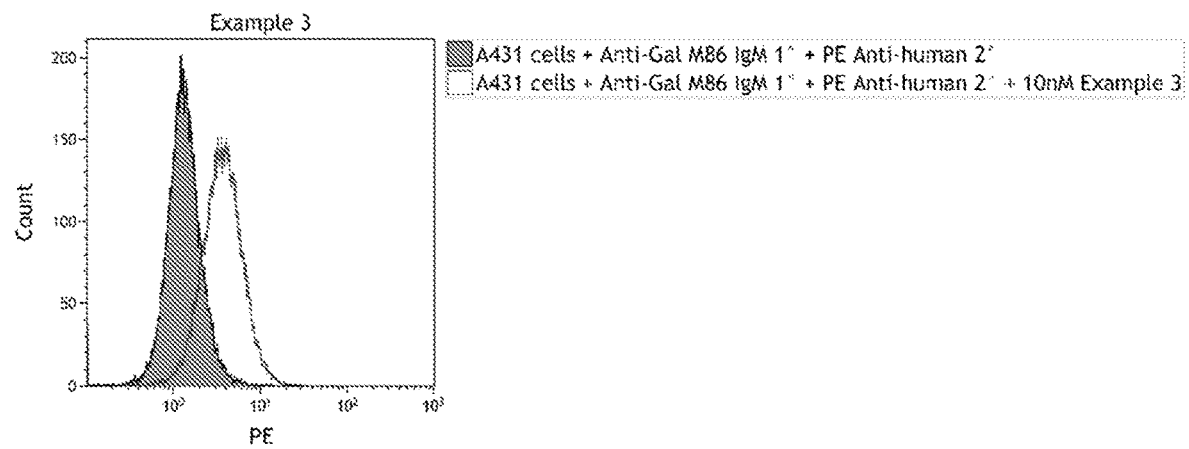

FIG. 4 demonstrates the capture of anti-alpha galactosyl IgM antibodies to the cell surface using Example 1 (FIG. 4A), Example 2 (FIG. 4B), Example 3 (FIG. 4C), Example 4 (FIG. 4D), Example 5 (FIG. 4E), Example 6 (FIG. 4F), Example 7 (FIG. 4G) and Example 8 (FIG. 4H) at 10 nM. The shift in fluorescence intensity (PE) occurs due to the binding event at each end of the molecule.

Flow Cytometry Assay Using Alpha-Galactosyl IgG Antibody

Flow cytometry was used to demonstrate binding of L (as cetuximab) to a receptor on a human cell line and F (as the carbohydrate molecule capable of binding to a human anti-alpha-galactosyl antibody). A431 cells are used to capture the EGFR binding mAb (cetuximab) as it is well known that the cells significantly over-express the EGFR receptor. A phycoerythrin (PE) labelled alpha-galactosyl IgG antibody was used to detect binding of the compound.

A431 cells (ATCC CRL-1555) were harvested and resuspended at $5 \times 10^6$ cells/mL in phosphate buffered saline (PBS) (Sigma D8662)+0.1% BSA (Bovine Serum Albumin—Sigma A2153). $5 \times 10^5$ cells were then incubated with compound at 10 nM, buffer alone or 10 nM Cetuximab at room temperature, shaking at 450 rpm for 1 hour. The cells were washed with 2×200 µL PBS+0.1% BSA, prior to adding 50 µL of PE labelled Anti-alpha galactosyl IgG antibody at 575 µg/mL in PBS+0.1% BSA and incubating at 4° C. for 1 hour. The Anti-alpha galactosyl IgG antibody (Absolute Antibody Ab00532.10.0) has been customed labelled with PE by Cambridge Research Biochemicals. After a final wash of 2×200 µL PBS+0.1% BSA the cells were resuspended in 200 µL PBS+0.1% BSA and evaluated on a flow cytometer (FC500 Beckman Coulter). Data from all samples were analysed in the Kaluza software package (Beckman Coulter).

Figure 5:
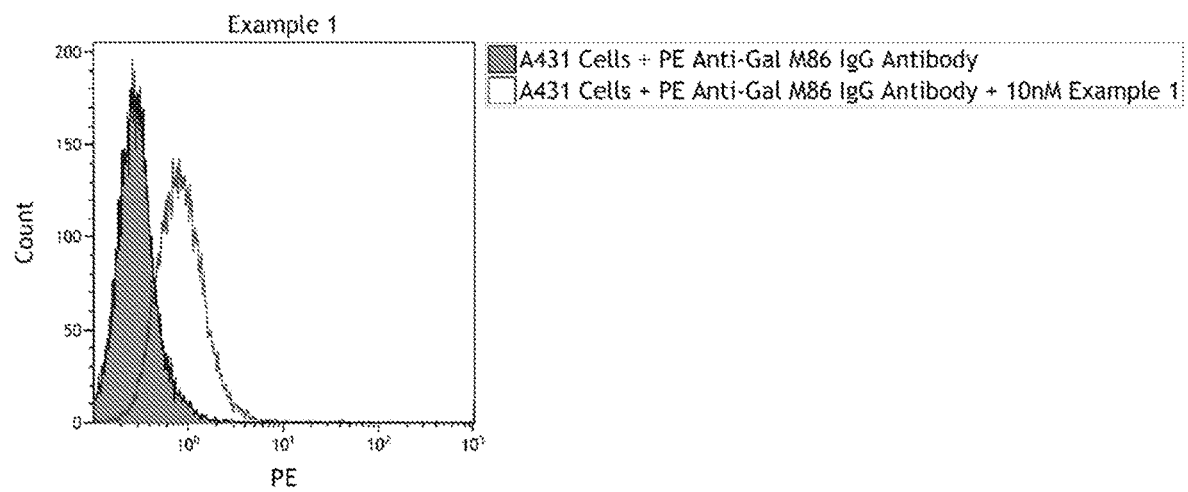
FIG. 5: M86 IgG data for the compounds of Examples 1-4.
Figure 5:
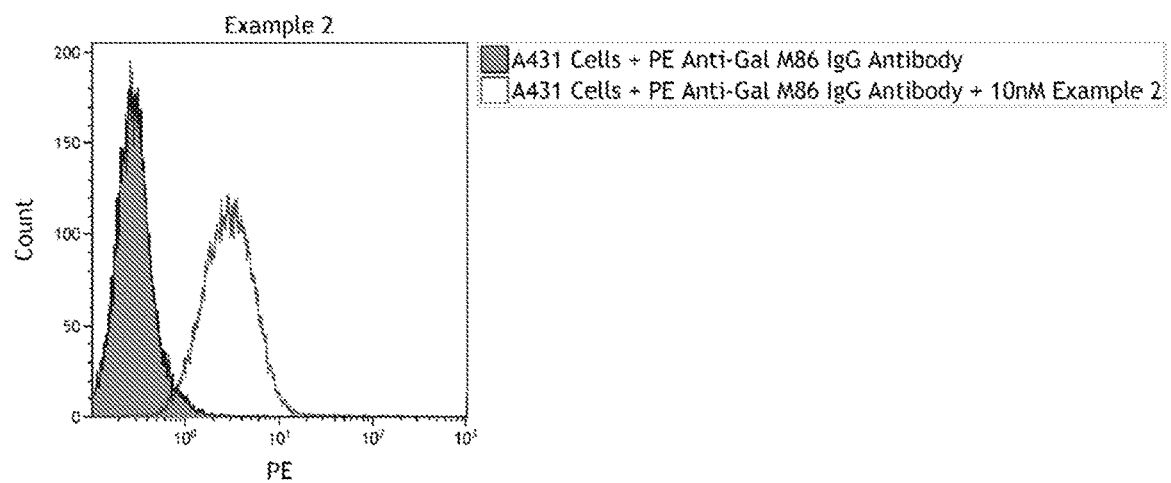

FIG. 5 demonstrates the capture of anti-alpha galactosyl IgG antibodies to the cell surface using Example 1 (FIG. 5A), Example 2 (FIG. 5B), Example 3 (FIG. 5C) and Example 4 (FIG. 5D) at 10 nM compared to buffer alone. The shift in fluorescence intensity (PE) occurs due to the binding event at each end of the molecule.

Figure 6:
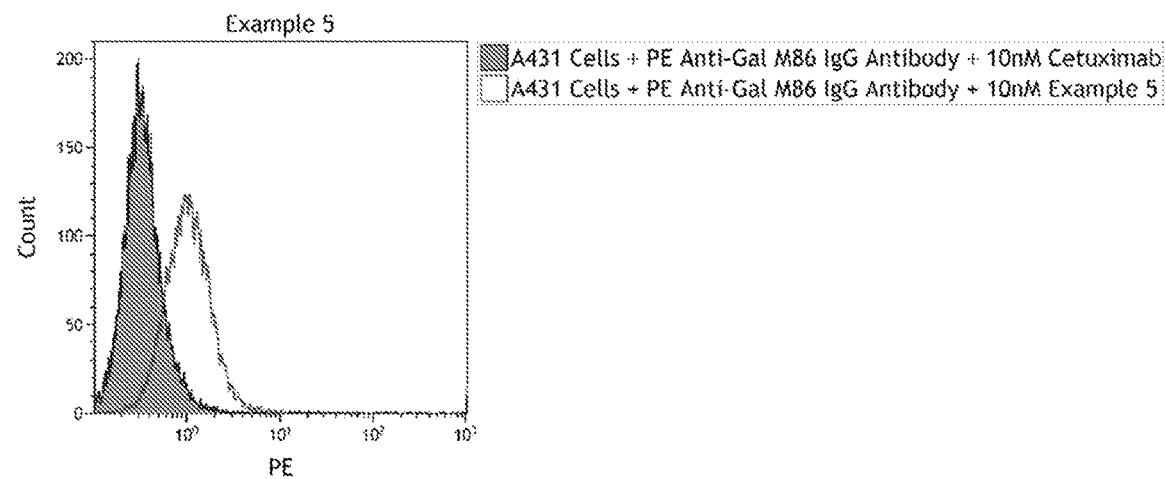
FIG. 6: Demonstrates the capture of anti-alpha galactosyl IgM antibodies to the cell surface using Example 5 (FIG. 6A), Example 6 (FIG. 6B), Example 7 (FIG. 6C) and Example 8 (FIG. 6D) at 10 nM compared to 10 nM Cetuximab.
Figure 6:
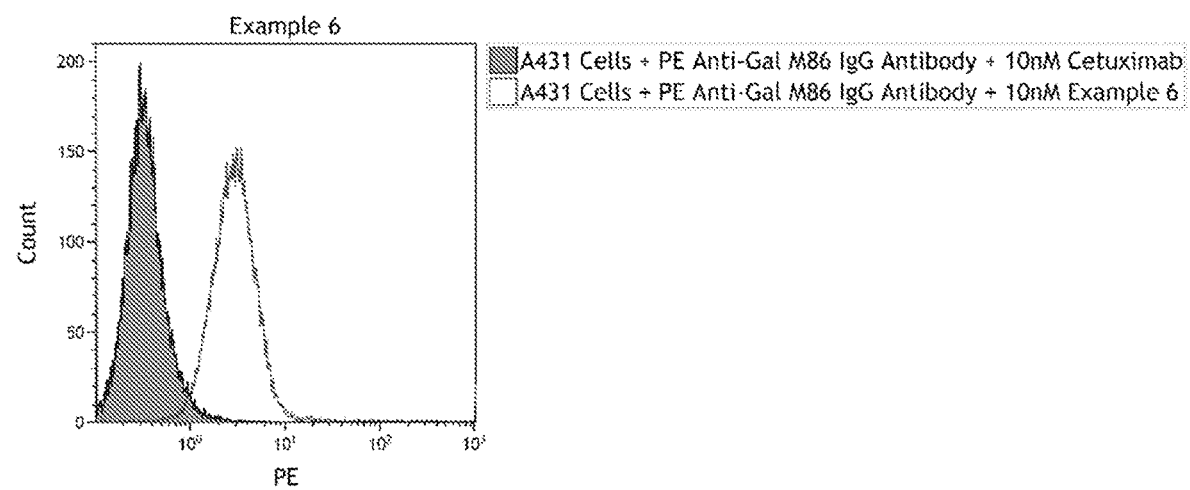

FIG. 6 demonstrates the capture of anti-alpha galactosyl IgG antibodies to the cell surface using Example 5 (FIG. 6A), Example 6 (FIG. 6B), Example 7 (FIG. 6C) and Example 8 (FIG. 6D) at 10 nM compared to 10 nM Cetuximab. The shift in fluorescence intensity (PE) occurs due to the binding event at each end of the molecule.

Flow Cytometry Assay Using Alpha-Galactosyl IgG Antibodies from hIVIG and A431 Cells Flow cytometry was used to demonstrate binding of L (as Fab fragment) to EGFR expressed on a human cell line (A431) and F (as the carbohydrate molecule capable of binding to a human anti-alpha-galactosyl antibody). A secondary phycoerythrin (PE) labelled anti-human IgG antibody was used to detect binding of the alpha-galactosyl IgG antibody to the compound.

A431 cells (ATCC CRL-1555) were harvested and resuspended at $5 \times 10^6$ cells/mL in phosphate buffered saline (PBS) (Sigma D8662)+0.1% BSA (Bovine Serum Albumin—Sigma A2153). $5 \times 10^5$ cells were then incubated with a range of compound concentrations up to 1000 nM, buffer alone or 1000 nM unconjugated Fab Fragment at room temperature, shaking at 450 rpm for 1 hour. The cells were washed with $2 \times 200$ μL PBS+0.1% BSA, prior to adding 50 μL of hIVIG anti-Gal IgG (70 μg/ml) (custom purification from human IVIG) in PBS+0.1% BSA and incubating at 4° C. for 1 hour.

The cells were washed with $2 \times 200$ μL PBS+0.1% BSA, prior to adding 100 μL of secondary anti-IgG-PE (clone HP6017, Biolegend 409393). The cells were incubated at 4° C. for 30 minutes in dark.

After a final wash of $2 \times 200$ μL PBS+0.1% BSA the cells were resuspended in 200 μL PBS+0.1% BSA and evaluated on a flow cytometer (FC500 Beckman Coulter). Data from all samples were analysed in the Kaluza software package (Version 1.5a, Beckman Coulter).

FIG. 7 demonstrates the dose related, compound driven recruitment of anti-Gal IgG antibodies from hIVIG to A431 cells for Examples 18-23 compared with the unconjugated Fab fragment where minimal recruitment is observed.

Flow Cytometry Assay Using Alpha-Galactosyl IgM Antibodies and A431 Cells

Compounds were tested at a range of concentrations, up to 1000 nM, following the flow cytometry assay protocol above, comparing to cetuximab and/or the unconjugated Fab fragment.

FIG. 8 demonstrates the dose related, compound driven recruitment of alpha-galactosyl IgM antibodies to A431 cells, compared with the unconjugated Fab fragment and/or cetuximab.

Flow Cytometry Assay Using C3b Antibodies

Flow cytometry was used to demonstrate binding of the compounds to a cell line of interest and recruitment of the C3b complement component to the cell.

A431 cells were used to capture the EGFR binding antibody or antibody fragment, as it is well known that the cells significantly over-express the EGFR receptor.

Anti-C3b antibody conjugated to phycoerythrin (PE) was used to detect recruitment of C3b molecules to cells from serum after addition of compound at varying concentrations.

A431 cells (ATCC CRL-1555) were harvested and resuspended at $5 \times 10^6$ cells/mL in phosphate buffered saline (PBS) (Sigma D8662)+0.1% BSA (Bovine Serum Albumin—Sigma A2153). $5 \times 10^5$ cells were then incubated with a range of compound concentrations up to 10000 ng/ml, buffer alone or varying concentrations of Cetuximab Fab Fragment and/or Cetuximab at room temperature, shaking at 450 rpm for 1 hour. The cells were washed with $2 \times 200$ μL PBS+0.1% BSA, prior to adding 100 μL PBS and 100 μL 20% Human Serum (HS) (Patricell 23590) or Heat Inactivated Human Serum (HIHS) with 25 μg/ml M86 IgM (Absolute Antibody) and incubating at 37° C. for 25 minutes.

The cells were washed with $2 \times 200$ μL PBS+0.1% BSA, prior to adding 100 μL of anti-C3b-PE (3E7/C3b, Biolegend 846104). The cells were incubated at 4° C. for 30 minutes in dark. After a final wash of $2 \times 200$ μL PBS+0.1% BSA the cells were resuspended in 200 μL PBS+0.1% BSA and evaluated on a flow cytometer (FC500 Beckman Coulter). Data from all samples were analysed in the Kaluza software package (Version 1.5a, Beckman Coulter).

FIG. 9 demonstrates the level of C3b deposition on A431 cells with varying concentrations of Examples 13-17, 20, 22, 23 and 24, compared to cetuximab Fab fragment and/or cetuximab. <5 fold shift over background was observed for all examples when heat inactivated human serum was employed (representative HI HS data is shown here).

Phagocytosis of Target Cells by Macrophages

Phagocytosis was used to demonstrate the functional effect of the binding of L (as the Fab fragment of cetuximab) to a receptor on a cell line and F (as the carbohydrate molecule capable of binding to a human anti-alpha-galactosyl antibody). A431 cells, reported to express EGFR were used as target cells. Monocyte derived macrophages were used as effector cells. Purified hIVIG was used a source of anti-Gal antibodies. The measured increase in integrated intensity occurs due to the phagocytosis of the target cells. No such increase is observed under control conditions (cells alone or in the presence of the unconjugated Fab fragment). Effector cells were differentiated in situ in 96-well-plates (Corning 3603). Briefly, blood from each healthy donor retained in a leukoreduction system chamber was purchased from the National Health Service (Addenbrooke's Hospital, Cambridge, UK). Peripheral blood mononuclear cells (PBMCs) were isolated using the Lymphoprep™ system following manufacturer's instructions (STEMCELL Technologies 07861). Monocytes were isolated from PBMCs by positive selection using the EasySep™ Human CD14 Positive Selection Kit II (STEMCELL Technologies 17858), re-suspended in ImmunoCult™-SF Macrophage Medium (STEMCELL Technologies 10961) supplemented with Recombinant human GM-CSF (Peprotech 300-03) at 100 ng/ml and plated at 20,000 cells/well in a cell culture incubator (5% $CO_2$, 37° C.). After 5 days of differentiation, macrophages were polarised towards the M1 phenotype with 100 ng/ml IFN-γ (Peprotech 300-02) and 1 ng/ml lipopolysaccharide (Invitrogen tlrl-eblps) for a further two days. A431 cells (ATCC CRL-1555) were cultured in Dulbecco's Modified Eagle's Medium (Gibco® 61965-026) supplemented with 10% Fetal Bovine Serum (Gibco® 10500-064), and used as target cells. Target cells were harvested using a Cell Dissociation Buffer (Gibco® 13151014), counted and labelled 10 mM pHrodo Green STP ester (Thermo Fisher Scientific P35369) at 1 μl per $1.0 \times 10^6$ cells of for 30 mins at 37° C. Cells were washed in complete medium, counted and then treated with a range of concentrations of Example 23, Example 20 or Cetuximab-Fab for 1 hr at RT with shaking.

Cells were then washed in medium free medium Incubate with 70 μg/ml hIVIG (custom purification from human IVIG) for 30 mins on ice, washed in Dulbecco's Phosphate Solution (Gibco® 14190-094) and co-cultured with effector cells (target:effector ratio 5:1) for up to 12 hours at 37° C. in the IncuCyte® (Sartorius). Images were acquired every two hours. Data were analysed using the IncuCyte®ZOOM software (Version 2016A, Sartorius). Graphs were produced with GraphPad Prism (version 6).

Figure 10:
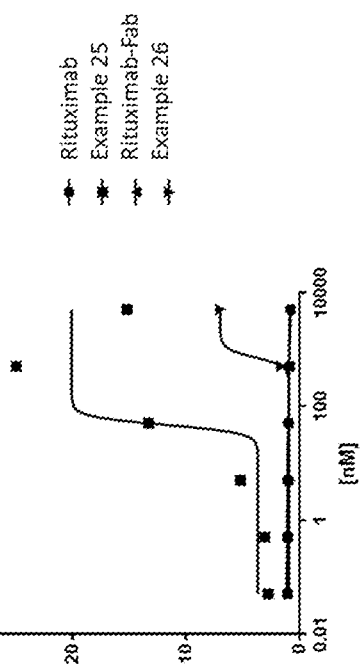
FIG. 10: Phagocytosis data for the compounds of Examples 20 and 23.

FIG. 10: demonstrates representative compound mediated phagocytosis in the presence of 1 nM Example 20 and Example 23, compared to the unconjugated Fab fragment. The target cells (EGFR expressing A431 cells) were phagocytosed by the effector cells (macrophages). The increase in the integrated intensity occurs due to the compound driven phagocytosis of the target cells.

Flow Cytometry Assay Using Alpha-Galactosyl IgM Antibody on Raji Cells

Flow cytometry was used to demonstrate binding of L (as Rituximab or rituximab Fab) to a receptor on a human cell line and F (as the carbohydrate molecule capable of binding to a human anti-alpha-galactosyl antibody). Raji cells are used to capture the CD20 binding mAb or Fab as it is well known that the cells significantly over-express the CD20 receptor. A secondary phycoerythrin (PE) labelled anti-human IgM antibody was used to detect binding of the alpha-galactosyl IgM antibody to the compound.

Raji cells (ATCC® CCL-86™) were harvested and resuspended at $5 \times 10^6$ cells/mL in phosphate buffered saline (PBS) (Gibco® 14190-094)+0.1% BSA (Bovine Serum Albumin—Sigma A2153). $5 \times 10^5$ cells were then incubated with compound at various concentrations as described below or buffer alone at room temperature, shaking at 450 rpm for 1 hour.

The cells were washed with 2×200 µL PBS+0.1% BSA, prior to adding 50 µL of an Anti-alpha galactosyl IgM antibody (Absolute Antibody Ab00532-15.0) at 32 µg/mL in PBS+0.1% BSA and incubating at 4° C. for 1 hour. The cells were further washed with 2×200 µL PBS+0.1% BSA before being treated with 100 µL 1:40 dilution of Anti-Human IgM-PE (Biolegend 314508) at 4° C. for 1 hour. After a final wash of 2×200 µL PBS+0.1% BSA the cells were resuspended in 200 µL PBS+0.1% BSA and evaluated on a flow cytometer (BD FACSVerse™, BD). Data from all samples were analysed in the FlowJo®, LLC software package. Graphs were produced with GraphPad Prism (version 6).

Figure 11:
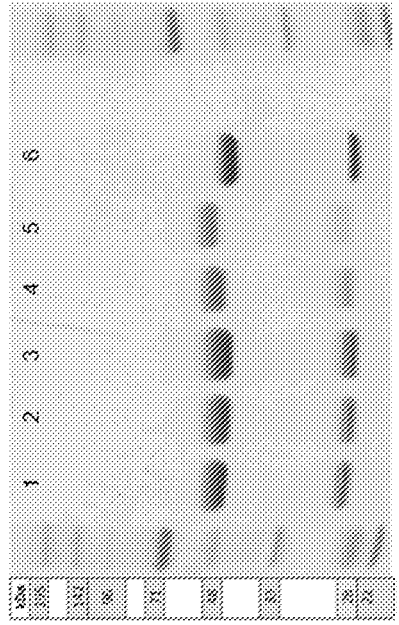
FIG. 11: is a dose titration for the compounds of Examples 25 and 26 recruiting anti-galactosyl M86 IgM antibodies to Raji cells
FIG. 12: Reducing SDS-PAGE gel analysis for cetuximab conjugate Examples 9 to 11 (FIG. 12A), Examples 12 to 16 (FIG. 12B) and Example 17 (FIG. 12C).
Figure 12A:
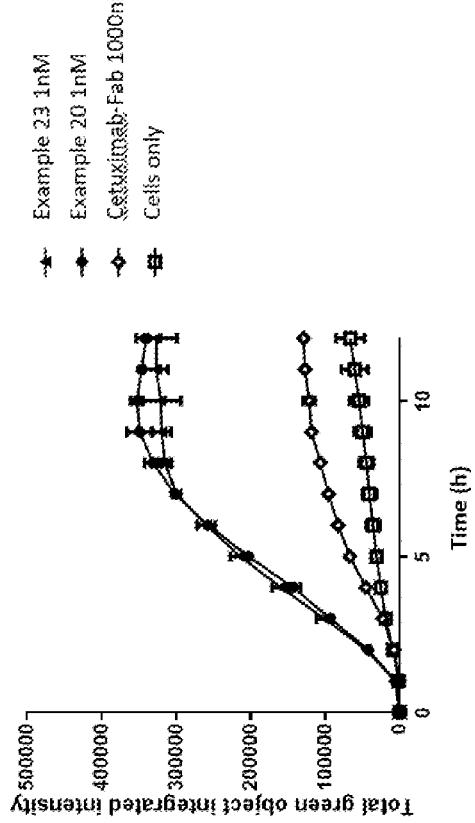
Figure 12B:
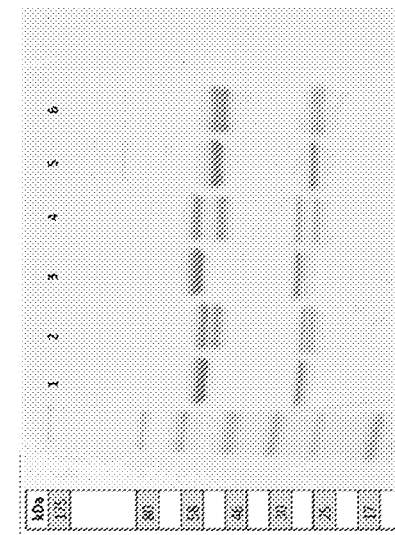
Figure 13A:
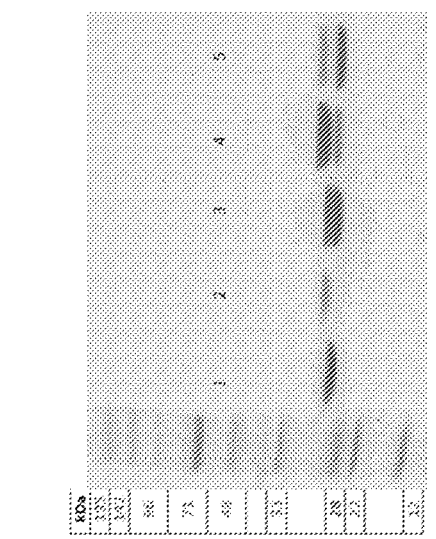
FIG. 13: Reducing SDS-PAGE gel analysis for cetuximab-Fab conjugates (Examples 18-24).
Figure 13C:
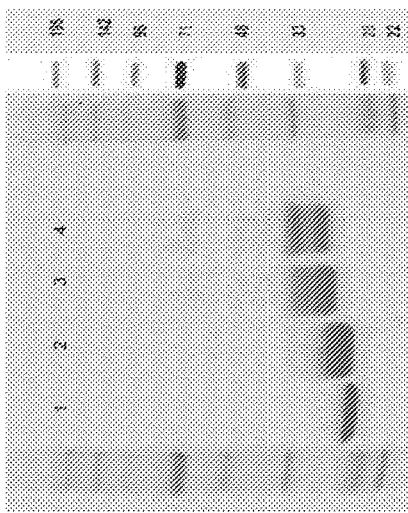
Figure 12C:
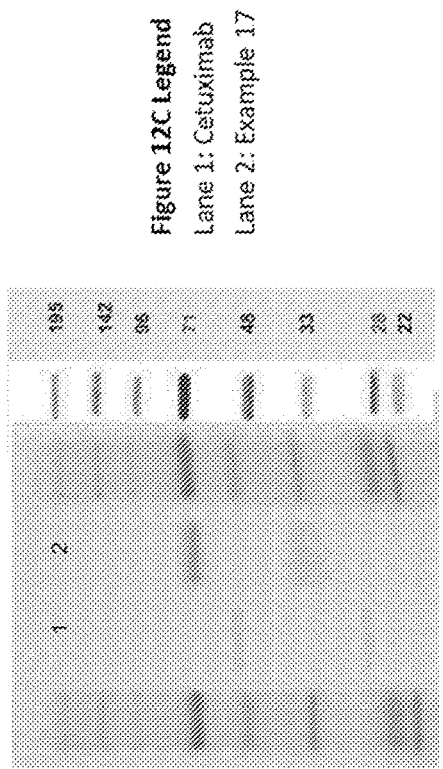
Figure 13B:
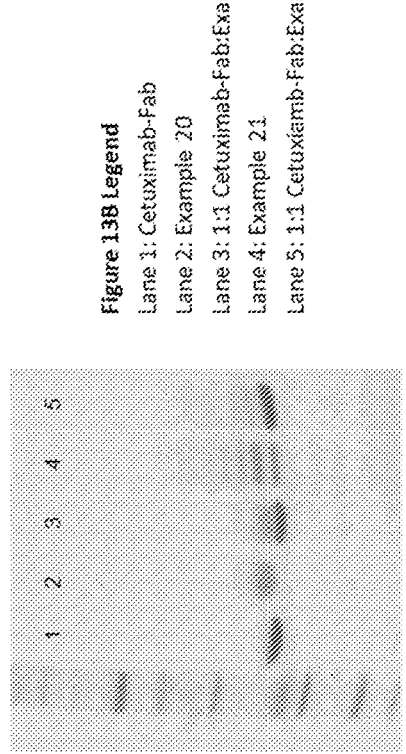
Figure 13D:
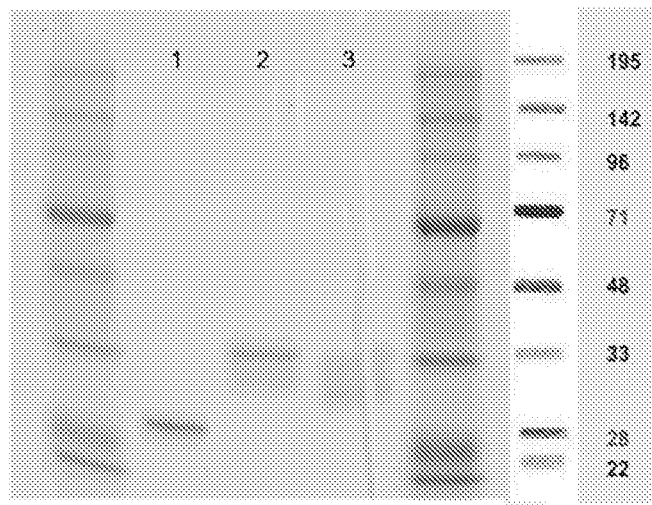
Figure 14A:
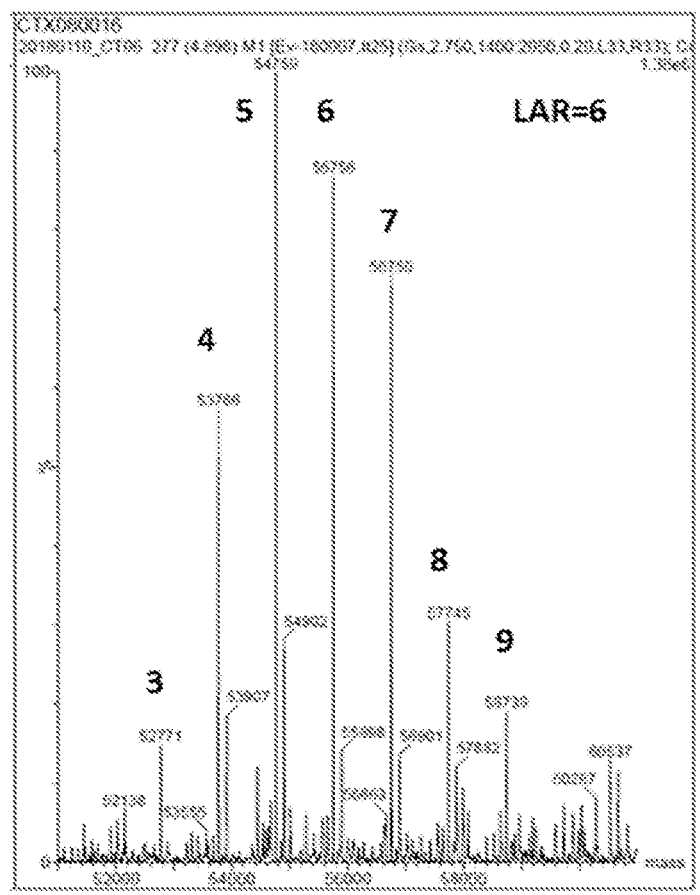
FIG. 14: MS Analysis for Examples 20 (FIG. 14A), 22 (FIG. 14B) and 23 (FIG. 14C).
Figure 14B:
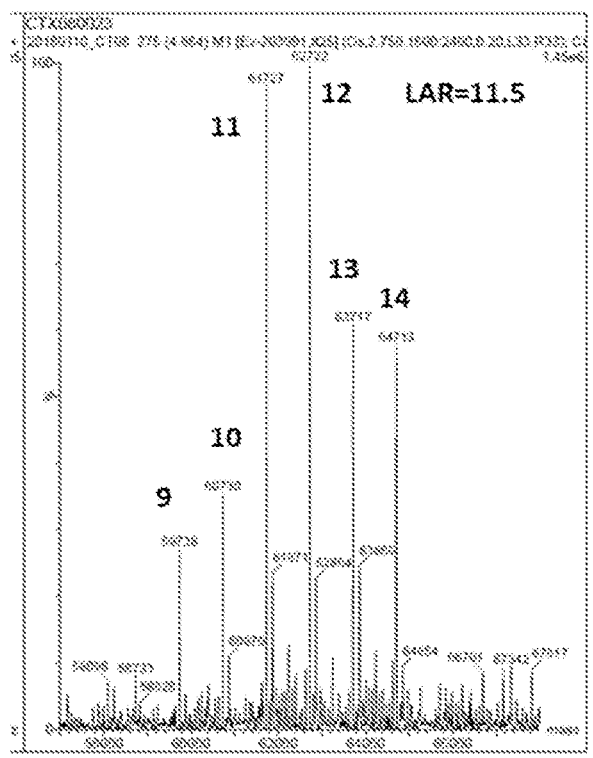
Figure 14C:
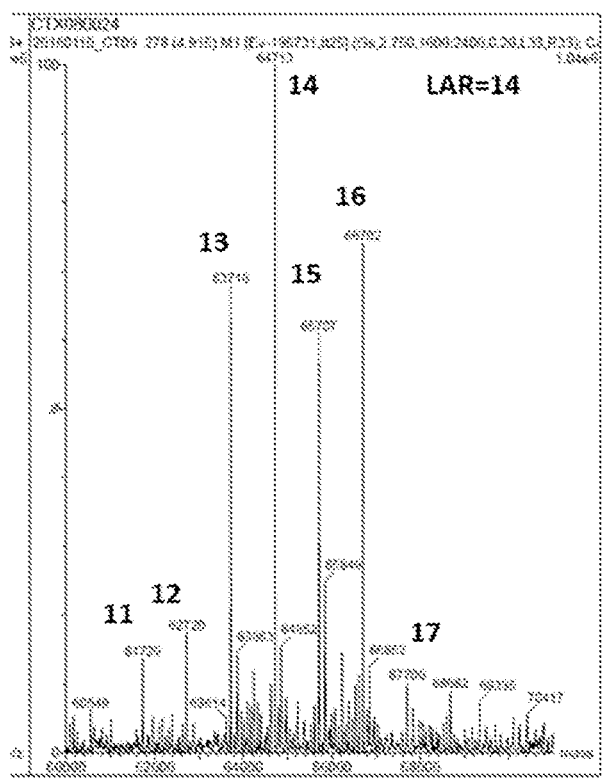
Figure 16B:
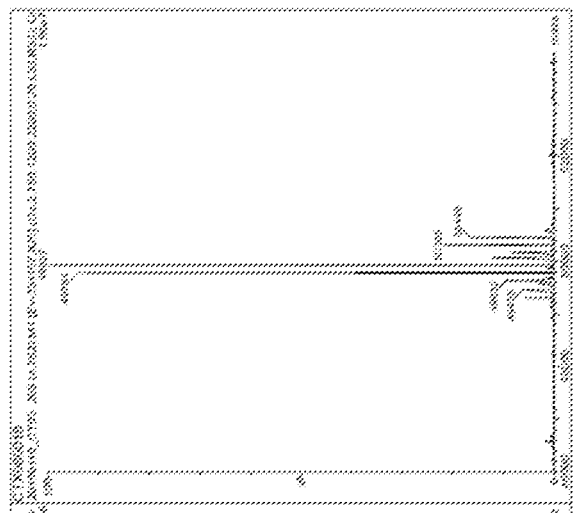
FIG. 16: SDS-PAGE (FIG. 16A), MS (FIG. 16B) and SEC (FIG. 16C) Analysis of cetuximab-Fab.
Figure 16A:
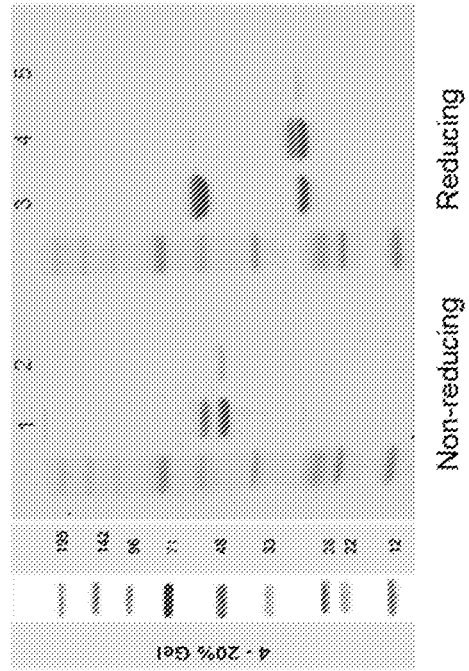
Figure 16C:
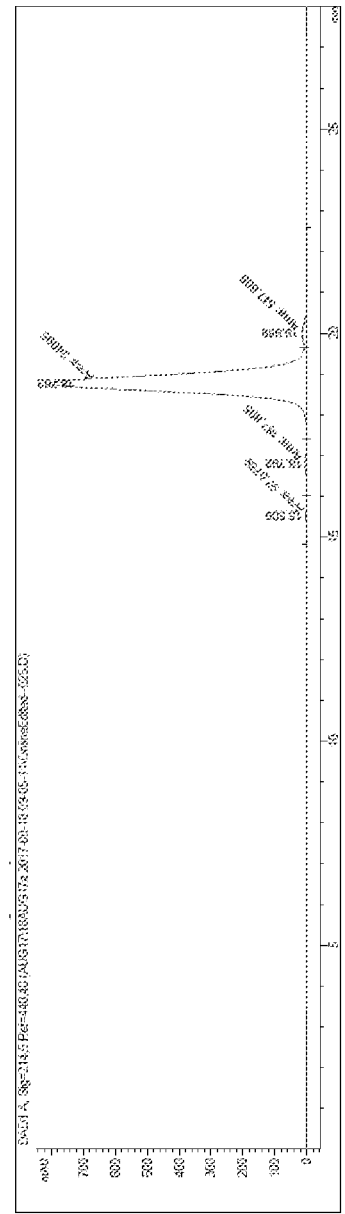

FIG. 11 demonstrates the dose related, compound driven recruitment of alpha-galactosyl IgM antibodies to Raji cells, compared with rituximab and its Fab fragment.

The invention claimed is:
1. A compound of formula (I) or a pharmaceutically acceptable salt thereof:

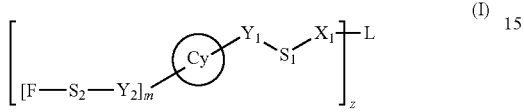

(I)

wherein L represents a binding moiety selected from an antibody or antigen binding fragment thereof;

$S_1$ represents a spacer selected from a —$(CH_2)_a$— or —$(CH_2)_b$—$(CH_2$—$CH_2$—$O)_c$—$(CH_2)_d$— group, wherein one to ten of said —$CH_2$— groups may optionally be substituted by one or more groups selected from —O—, —S—, =N(H)—, —C(=O)—, —C(O)NH—, —NHC(O)—, cyclohexyl or pyrrolidine-2,5-dione;

a represents an integer selected from 1 to 35;
b represents an integer selected from 0 to 5;
c represents an integer selected from 1 to 20;
d represents an integer selected from 1 to 20;

$S_2$ represents a spacer selected from a —$(CH_2)_e$— or —$(CH_2)_f$—$(CH_2$—$CH_2$—$O)_g$—$(CH_2)_h$— group, wherein one to three of said —$CH_2$— groups may optionally be substituted by one or more groups selected from —N(H)—, —C(O)NH— and —NHC(O)—;

e represents an integer selected from 1 to 15;
f represents an integer selected from 1 to 10;
g represents an integer selected from 1 to 20;
h represents an integer selected from 1 to 5;
z represents an integer selected from 1 to 30;
$X_1$ represents an antibody or antigen binding fragment attachment moiety;
$Y_1$ and $Y_2$ independently represent a bond, —O—, —S—, —NH—, —NHC(O)—, —C(O)NH—, —OC(O)—, —C(O)O—, —SC(O)—, —C(O)S—, —NHSO_2—, —SO_2NH— or —NHC(O)NH— group;
F represents a carbohydrate molecule capable of binding to a human anti-alpha-galactosyl antibody;
m represents an integer selected from 1 to 5; and
Cy represents phenyl, biphenyl, triphenyl, wherein when Cy represents biphenyl or triphenyl said —$Y_1$—$S_1$—$X_1$-L group may be present on any of said phenyl rings and said [F—$S_2$—$Y_2]_m$— group or groups may be present on any of said phenyl rings.

2. The compound as defined in claim 1, wherein:
$S_1$ represents a spacer selected from:
—$(CH_2)_a$—, wherein one to five of said —$CH_2$— groups may optionally be substituted by one or more groups selected from —S—, =N(H)—, —C(=O)—, —NHC(O)—, cyclohexyl or pyrrolidine-2,5-dione;
—$(CH_2)_b$—$(CH_2$—$CH_2$—$O)_c$—$(CH_2)_d$—, wherein one to five of said —$CH_2$— groups may optionally be substituted by one or more groups selected from —NHC(O)— or pyrrolidine-2,5-dione; and/or
wherein $X_1$ represents —S— or —N(H)—; and/or
wherein a represents an integer selected from 1 to 30; or 2 to 30; or 2, 4, 6, 9, 11, 18 or 30; or 6 to 30; or 6, 11, 18 or 30; or 5 to 15; or 6 to 11; or 6, 7 or 11; or 6; or 7; or 11; and/or
wherein b represents an integer selected from 0 to 3; or 0 or 3; or 1 to 3; or 2 or 3; or 3; and/or
wherein c represents an integer selected from 1 to 15; or 1 to 12; or 4 to 12; or 4 or 12; or 4; and/or
wherein d represents an integer selected from 1 to 15; or 2 to 13; or 2, 5 or 13; or 13; or 3; and/or
wherein $Y_1$ represents a bond, —C(O)NH— or —O—; or —C(O)NH—; and/or
wherein $S_2$ represents a spacer selected from:
—$(CH_2)_e$—, wherein one or two of said —$CH_2$— groups are optionally substituted by one or two groups selected from —N(H)—, —C(O)NH— and —NHC(O)—; or
—$(CH_2)_f$—$(CH_2$—$CH_2$—$O)_g$—$(CH_2)_h$—, wherein one to three of said —$CH_2$— groups are optionally substituted by one to three —NHC(O)— groups;
or $S_2$ represents a spacer selected from:
—$(CH_2)_e$—, wherein one or two of said —$CH_2$— groups are optionally substituted by a —C(O)NH— or —NHC(O)— group or —$(CH_2)_f$—$(CH_2$—$CH_2$—$O)_g$—$(CH_2)_h$—, wherein one or two of said —$CH_2$— groups are optionally substituted by a —C(O)NH— or —NHC(O)— group;
or $S_2$ represents a spacer selected from:
—$(CH_2)_e$—, wherein one or two of said —$CH_2$— groups are optionally substituted by one or two —NHC(O)— groups; or
—$(CH_2)_f$—$(CH_2$—$CH_2$—$O)_g$—$(CH_2)_h$—, wherein one to three of said —$CH_2$— groups are optionally substituted by one to three —NHC(O)— groups;
or $S_2$ represents a spacer selected from:
—$(CH_2)_e$—, wherein one or two of said —$CH_2$— groups are optionally substituted by one or two groups selected from —N(H)—, —C(O)NH— and —NHC(O)—; or
—$(CH_2)_f$—$(CH_2$—$CH_2$—$O)_g$—$(CH_2)_h$—, wherein one to three of said —$CH_2$— groups are optionally substituted by one to three —NHC(O)— groups;
or $S_2$ represents a spacer selected from:
—$(CH_2)_e$—, wherein one or two of said —$CH_2$— groups are optionally substituted by one or two groups selected from —N(H)—, —C(O)NH— and —NHC(O)—;
or $S_2$ represents a spacer selected from:
—$(CH_2)_e$—, wherein one of said —$CH_2$— groups is optionally substituted by a —NHC(O)— group; or
—$(CH_2)_f$—$(CH_2$—$CH_2$—$O)_g$—$(CH_2)_h$—, wherein two of said —$CH_2$— groups are optionally substituted by an —NHC(O)— group; and/or
wherein e represents an integer selected from 1 to 10; or 3 to 10; or 3, 5, 9 or 10; or 5 to 9; or 5 or 9; or 4 to 10; or 4, 5 or 10; or 5; and/or wherein f represents an integer selected from 1 to 8; or 2 to 8; or 2 to 6; or 4 to 8; or 4 or 8; or 4; and/or wherein g represents an integer selected from 1 to 15; or 4 to 12; or 4 or 12; or 1 to 5; or 1 to 4; or 4; and/or wherein h represents an integer selected from 1 to 4; or 4; and/or wherein $Y_2$ represents a bond, —O— or —NHC(O)—; or a bond or —O—; or —O—; and/or wherein m represents an integer selected from 1 to 4; or 1 to 3; 1 or 3; or 2 or 3; or 1 or 2; or 1; or 2; or 3; or 4; and/or wherein z represents an integer selected from 2 to 20; or 2; or 5; or 7; or 8; or 10; or 11; or 14; or 15; or 17; or 20; and/or wherein Cy represents biphenyl.

3. A compound as defined in claim 1, wherein:

L represents a binding moiety selected from an antibody or antigen binding fragment thereof;

$S_1$ represents a spacer selected from:

—$(CH_2)_a$—, wherein 2, 3 or 5 of said —$CH_2$— groups may optionally be substituted by one or more groups selected from —S—, =N(H)—, —C(=O)—, —NHC(O)—, cyclohexyl or pyrrolidine-2,5-dione; or —$(CH_2)_b$—$(CH_2$—$CH_2$—$O)_c$—$(CH_2)_d$—, wherein two of said —$CH_2$— groups may optionally be substituted by one or more groups selected from —NHC(O)— or pyrrolidine-2,5-dione;

a represents an integer selected from 6, 7 or 11;
b represents an integer selected from 3;
c represents an integer selected from 4;
d represents an integer selected from 3;

$S_2$ represents a spacer selected from:

—$(CH_2)_e$—, wherein one of said —$CH_2$— groups is optionally substituted by a —NHC(O)— group; or —$(CH_2)_f$—$(CH_2$—$CH_2$—$O)_g$—$(CH_2)_h$—, wherein two of said —$CH_2$— groups are optionally substituted by an —NHC(O)— group;

e represents an integer selected from 5;
f represents an integer selected from 4;
g represents an integer selected from 4;
h represents an integer selected from 4;
z represents an integer selected from 2 to 20;
$X_1$ represents —S— or —N(H)—;
$Y_1$ represents —C(O)NH—;
$Y_2$ represents —O—;
F represents a carbohydrate molecule capable of binding to a human anti-alpha-galactosyl antibody;
m represents an integer selected from 1 or 3; and
Cy represents biphenyl, wherein said —$Y_1$—$S_1$—$X_1$-L group may be present on either of said phenyl rings and said [F—$S_2$—$Y_2$]$_m$— group or groups may be present on either of said phenyl rings.

4. The compound as defined in claim 1, wherein the antibody is:
a polyclonal antibody, a humanized antibody, a human antibody, a murine antibody or a chimeric antibody.

5. The compound as defined in claim 1, wherein the antigen binding fragment thereof is an antigen-binding fragment (Fab) or a single-chain variable fragment (scFv).

6. The compound as defined in claim 1, wherein the antibody or antigen binding fragment thereof is selected from:
an EGFR antibody or a fragment thereof.

7. The compound as defined in claim 1, wherein F is selected from galactosyl-alpha-1,3-galactosyl-beta-1,4-N-acetylglucosamine, alpha 1-3 galactobiose, alpha1-3-beta1-4-galactotriose or galilipentasaccharide.

8. The compound as defined in claim 1 or a pharmaceutically acceptable salt thereof, which is selected from any one of:

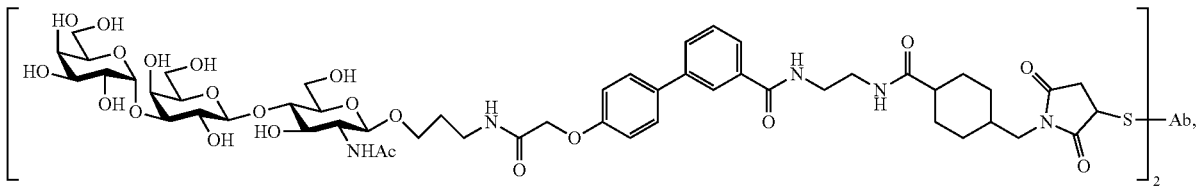

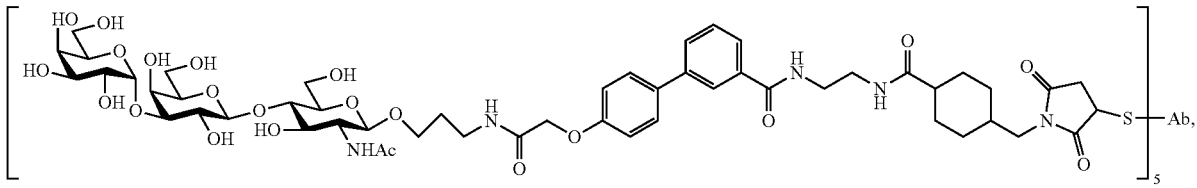

-continued
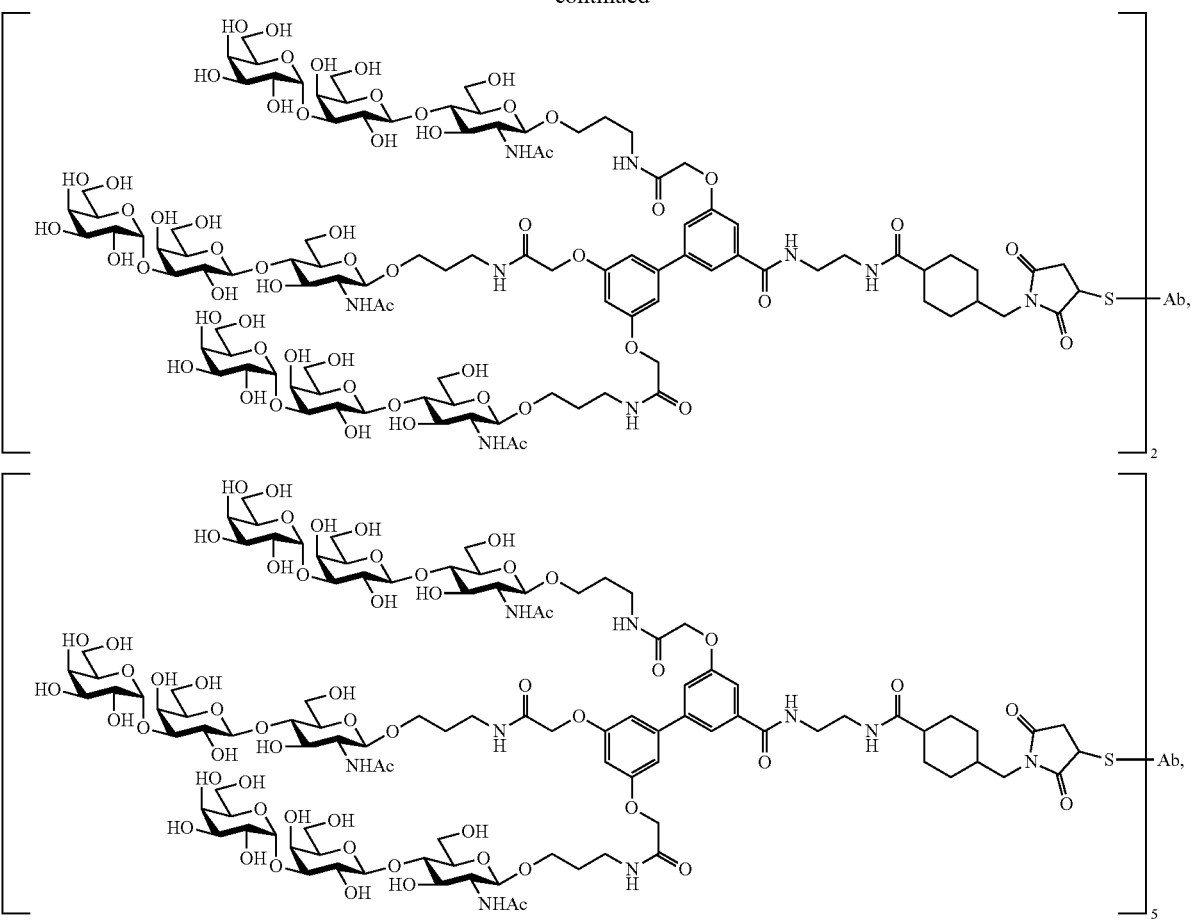
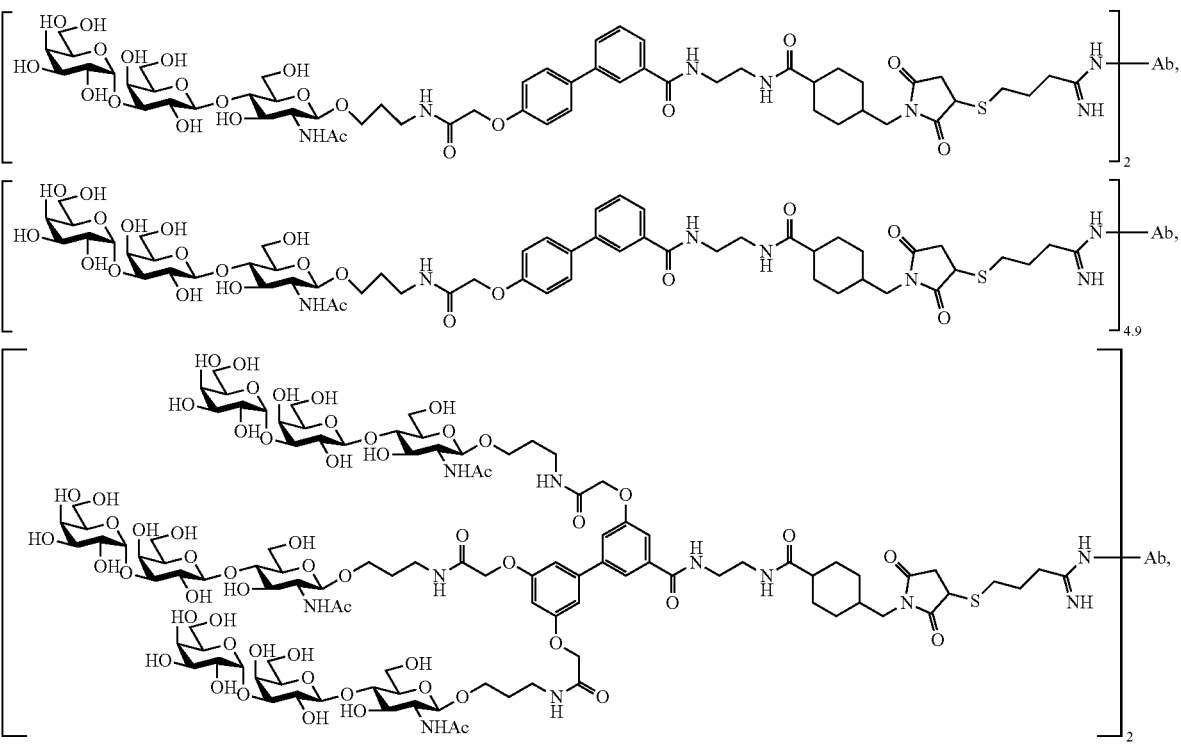

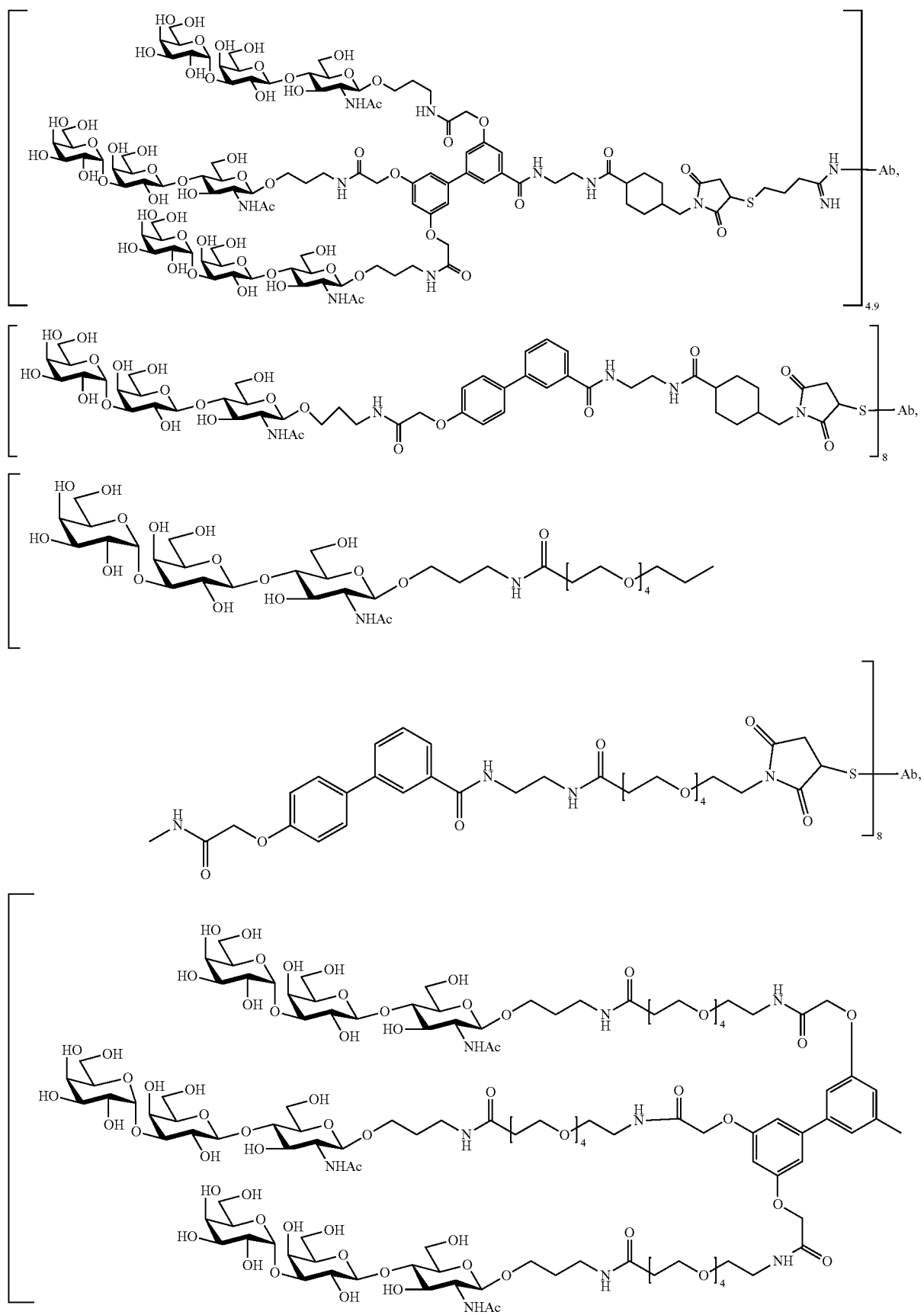

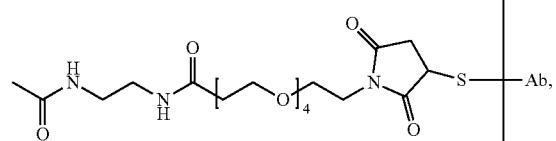
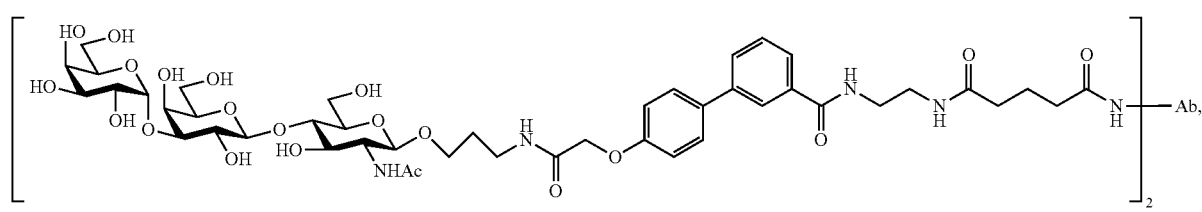
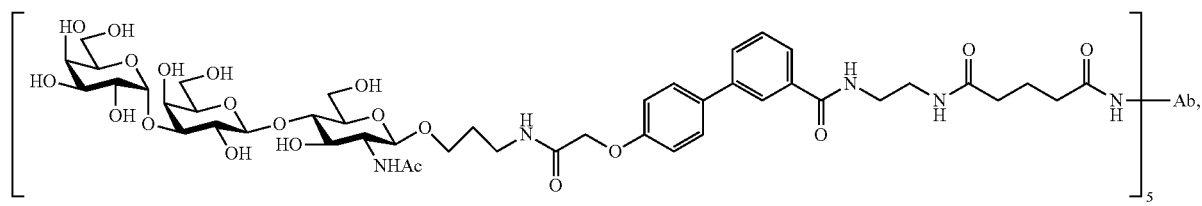
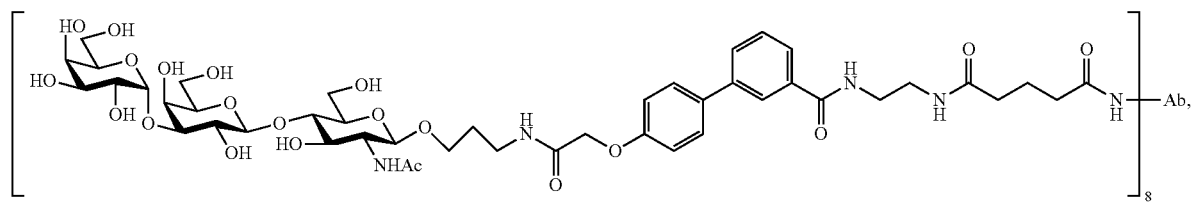
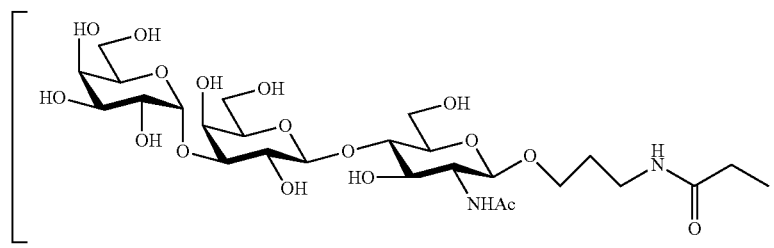
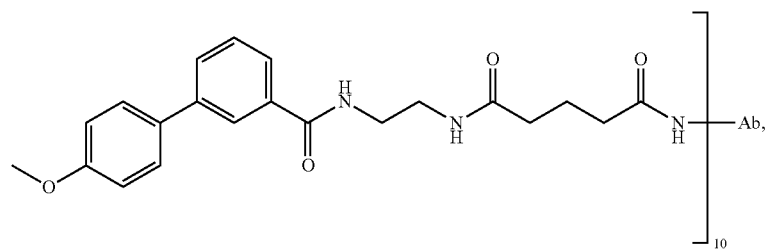

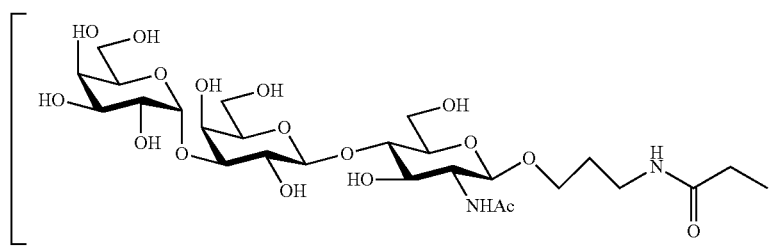
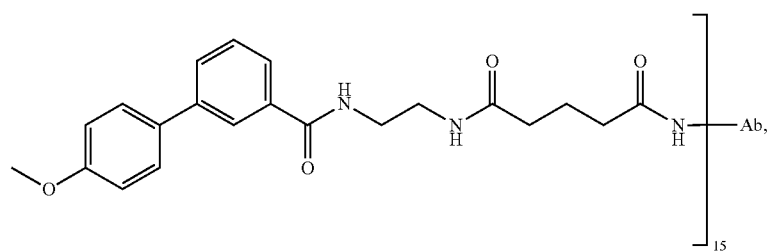
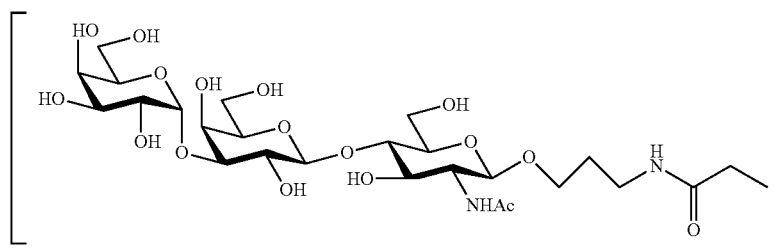
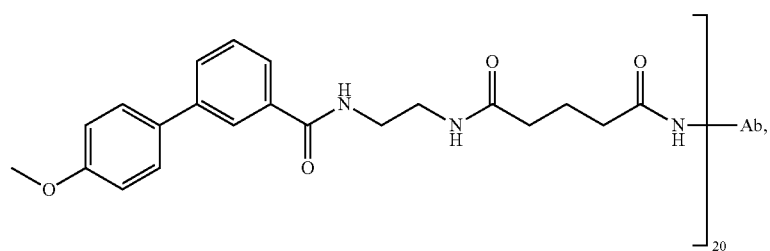
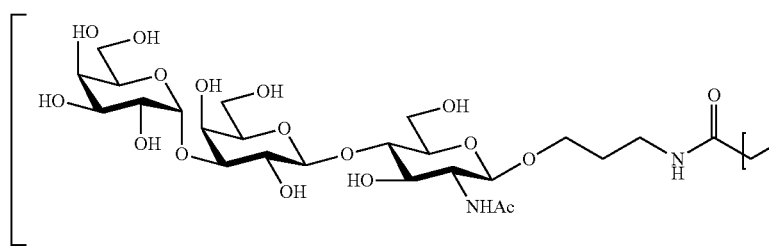
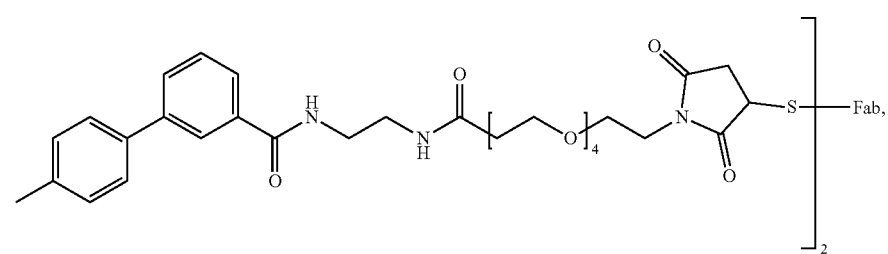

-continued
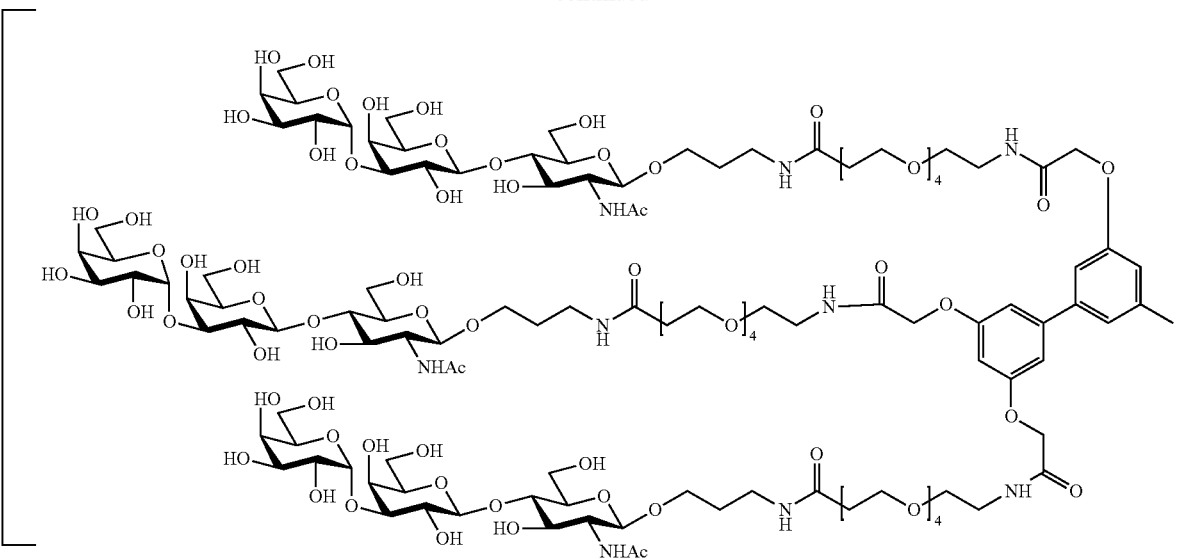
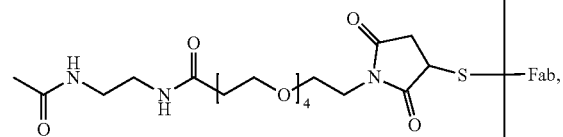
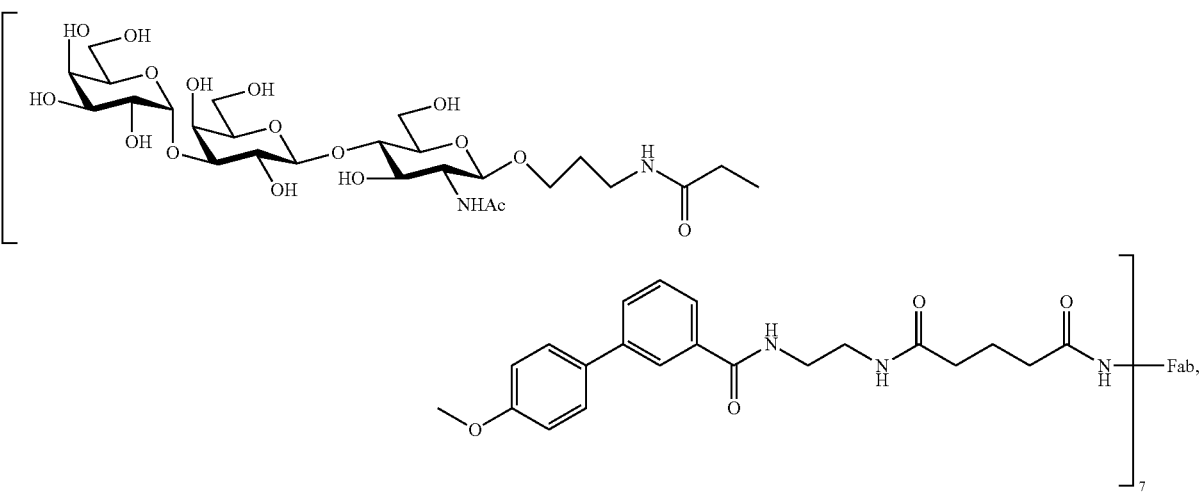

111
112
-continued
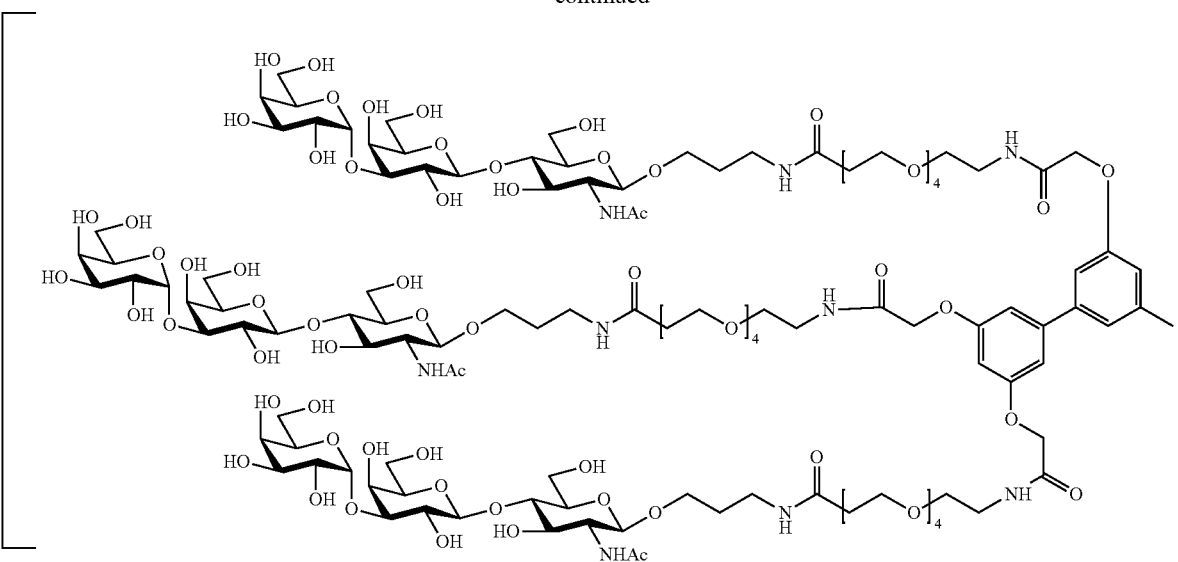
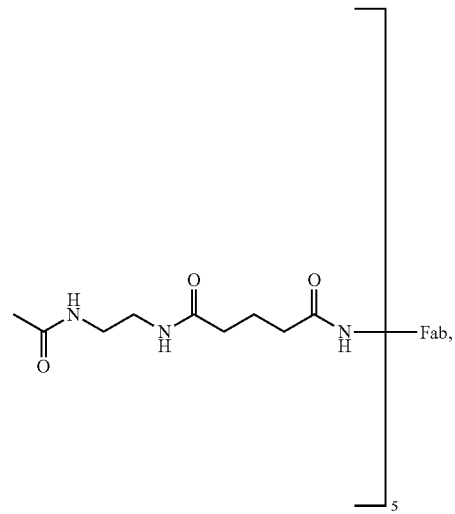
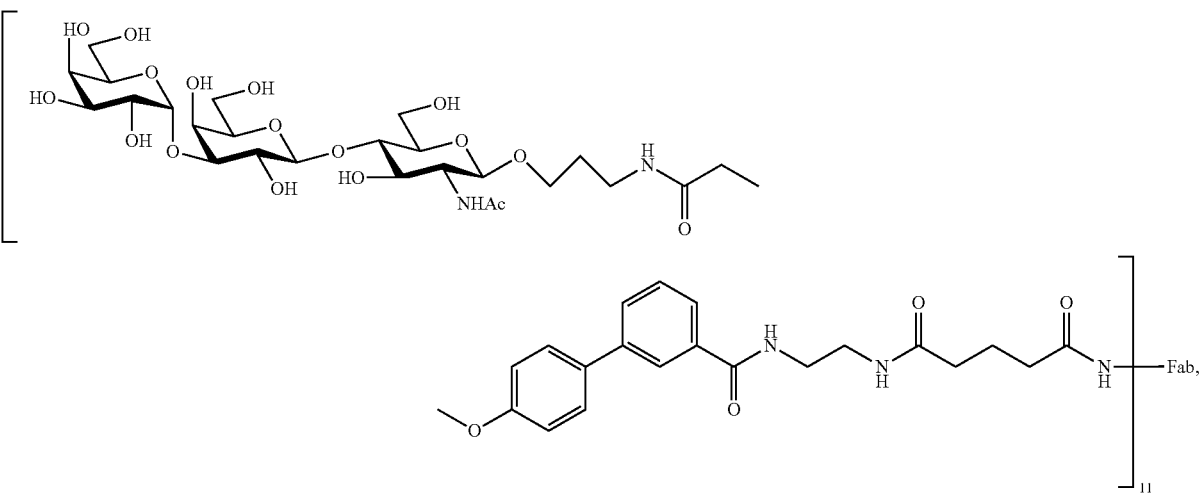

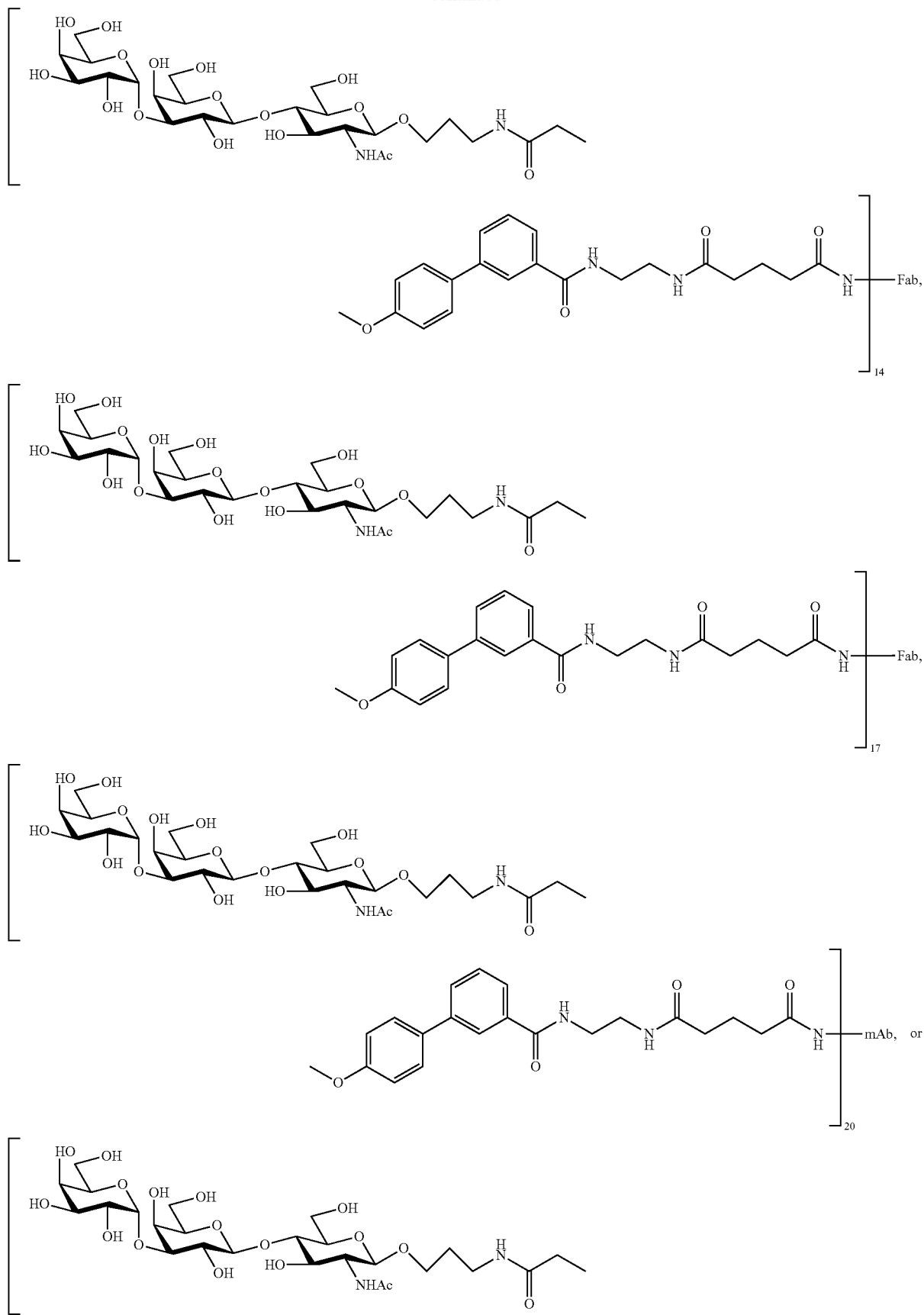

-continued

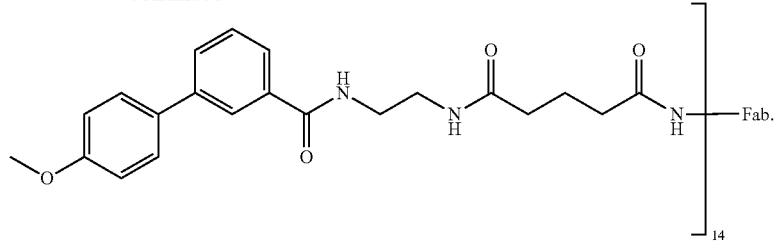

9. A pharmaceutical composition comprising a compound as defined in claim 1 or a pharmaceutically acceptable salt thereof.

10. The pharmaceutical composition as defined in claim 9, which additionally comprises one or more further therapeutic agents.

11. A method of treating cancer administering to an individual in need thereof a compound as defined in claim 1 or a pharmaceutically acceptable salt thereof.

12. A method of treating a bacterial infection which comprises administering to an individual in need thereof a compound as defined in claim 1 or a pharmaceutically acceptable salt thereof.

13. A process for preparing a compound of formula (I) as defined in claim 1 which comprises:

(a) preparing a compound of formula (IA) wherein $X_1$ as defined in claim 1 represents —S— by reacting a compound of formula (III) wherein the antibody or antigen binding fragment contains at least one reactive thiol group with a compound of formula (II) wherein $S_1$ is terminated with pyrrolidine-2,5-dione:

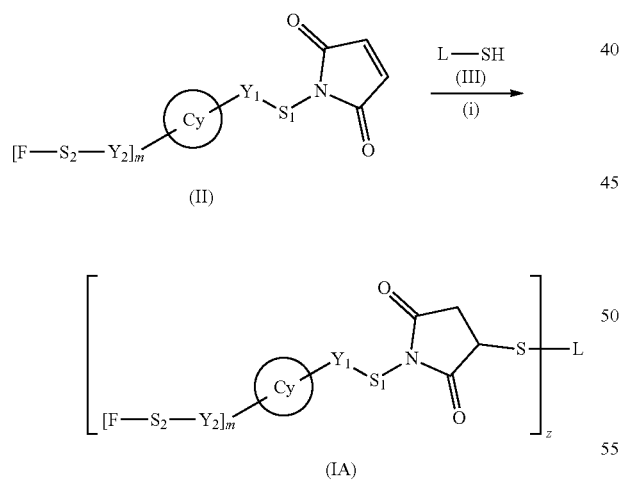

wherein F, $S_2$, $Y_2$, m, Cy, $Y_1$ and $S_1$ are as defined in claim 1; or (b) preparing a compound of formula (IC) wherein $X_1$ as defined in claim 1 represents —NH$_2$ and $S_1$ contains —S—CH$_2$—CH$_2$—CH$_2$—C(=NH)—, by reacting a compound of formula (IIIA) wherein the antibody or antigen binding fragment contains at least one reactive thiol group with a compound of formula (II) wherein $S_1$ is terminated with pyrrolidine-2,5-dione:

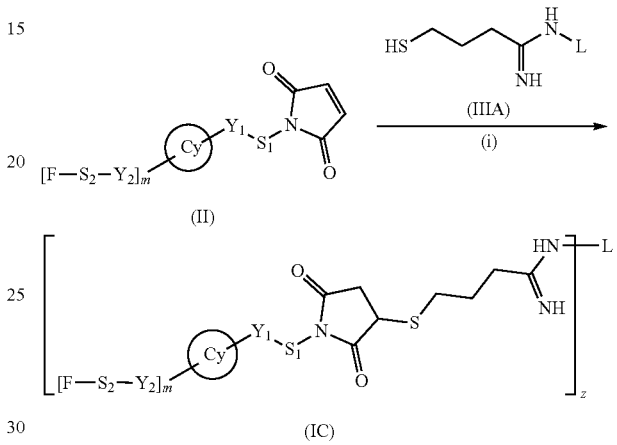

wherein F, $S_2$, $Y_2$, m, Cy, $Y_1$, $S_1$ and L are as defined in claim 1; or (c) preparing a compound of formula (TB) wherein $X_1$ as defined in claim 1 represents —NH$_2$ by reacting a compound of formula (IIB) wherein $S_1$ is terminated with a N-hydroxysuccinimide group with compounds of formula (IIIB) wherein the antibody or antigen binding fragment contains at least one reactive amino group:

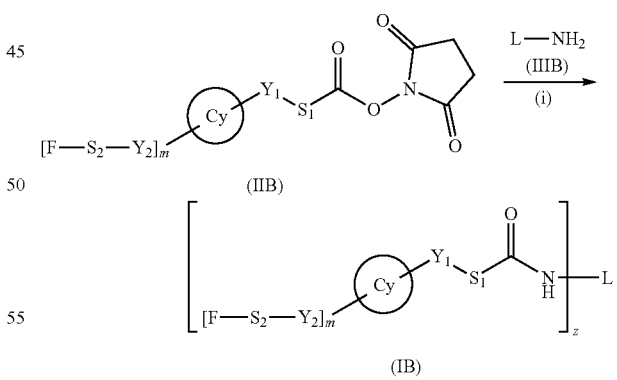

wherein F, $S_2$, $Y_2$, m, Cy, $Y_1$, $S_1$ and L are as defined in claim 4; and/or (d) interconversion of a compound of formula (I) or protected derivative thereof to a further compound of formula (I) or protected derivative thereof.

14. The compound as defined in claim 1, wherein the antibody or antigen binding fragment thereof is selected from a CD20 antibody or a fragment thereof.

15. The compound as defined in claim 1, wherein the antibody or antigen binding fragment thereof is selected from a pathogen specific antibody or a fragment thereof.

16. The compound as defined in claim 2, wherein $S_1$ represents —$(CH_2)_a$—, wherein 2, 3 or 5 of said —$CH_2$— groups are optionally substituted by one or more groups selected from —S—, =N(H)—, —C(=O)—, —NHC(O)—, or cyclohexyl or pyrrolidine-2,5-dione.

17. The compound as defined in claim 2, wherein $S_1$ represents —$(CH_2)_a$—, wherein said one to five of said —$CH_2$— groups are optionally substituted by one or more of —$(CH_2)_2$—NHCO-cyclohexyl-$CH_2$-3-pyrrolidine-2,5-dione-, —$(CH_2)_2$—NHCO-cyclohexyl-$CH_2$-3-pyrrolidine-2,5-dione-S—$(CH_2)_3$—C(=NH)— or —$(CH_2)_2$—NHCO—$(CH_2)_3$—CO—.

18. The compound as defined in claim 2, wherein $S_1$ represents —$(CH_2)_b$—$(CH_2$—$CH_2$—$O)_c$—$(CH_2)_d$—, wherein one to five of said —$CH_2$— groups are optionally substituted by —$(CH_2)_2$—NHCO—$(CH_2CH_2O)_4$—$(CH_2)_2$-3-pyrrolidine-2,5-dione-.

19. The compound as defined in claim 2, wherein $S_2$ represents —$(CH_2)_e$—, wherein one or two of said —$CH_2$— groups are optionally substituted by one or two of —$(CH_2)_3$—NHCO—$CH_2$—, —$(CH_2)_3$—, —$(CH_2)_3$—NHCO—$(CH_2)_4$—CONH—$CH_2$—, —$(CH_2)_3$—NH—$CH_2$— or —$(CH_2)_3$—NHCO—$(CH_2)_3$—NHCO—$CH_2$—.

20. The compound as defined in claim 2, wherein $S_2$ represents —$(CH_2)_f$—$(CH_2$—$CH_2$—$O)_g$—$(CH_2)_h$—, wherein one to three of said —$CH_2$— groups are optionally substituted by one to three of —$(CH_2)_3$—NHCO—$(CH_2CH_2O)_4$—$(CH_2)_2$—NHCO—$CH_2$—, —$(CH_2)_3$—NHCO—$(CH_2CH_2O)_{12}$—$(CH_2)_2$—NHCO—$CH_2$— or —$(CH_2)_3$—NHCO—$(CH_2)_3$—NHCO—$(CH_2CH_2O)_4$—$(CH_2)_2$—NHCO—$CH_2$—.

21. The compound as defined in claim 2, wherein $S_2$ represents —$(CH_2)_e$—, wherein one or two of said —$CH_2$— groups are optionally substituted by —$(CH_2)_3$—NHCO—$CH_2$—, —$(CH_2)_3$—NHCO—, —$(CH_2)_3$—, —$(CH_2)_3$—NHCO—$(CH_2)_4$—CONH—$CH_2$— or —$(CH_2)_3$—NH—$CH_2$—.

22. The compound as defined in claim 2, wherein $S_2$ represents —$(CH_2)_e$—, wherein one or two of said —$CH_2$— groups are optionally substituted by —$(CH_2)_f$—$(CH_2$—$CH_2$—$O)_g$—$(CH_2)_h$—, wherein one or two of said —$CH_2$— groups are optionally substituted by —$(CH_2)_3$—NHCO—$(CH_2)_2$—$(OCH_2CH_2)_4$—NHCO—$CH_2$— or —$(CH_2)_4$—NHCO—$(CH_2)_2$—$(OCH_2CH_2)_4$—NHCO—$CH_2$—.

23. The compound as defined in claim 2, wherein $S_2$ represents —$(CH_2)_e$—, wherein one or two of said —$CH_2$— groups are optionally substituted by one or two-of —$(CH_2)_3$—NHCO—$CH_2$— or —$(CH_2)_3$—NHCO—$(CH_2)_3$—NHCO—$CH_2$—.

24. The compound as defined in claim 2, wherein $S_2$ represents —$(CH_2)_f$—$(CH_2$—$CH_2$—$O)_g$—$(CH_2)_h$—, wherein one to three of said —$CH_2$— groups are optionally substituted by one to three of —$(CH_2)_3$—NHCO—$(CH_2CH_2O)_4$—$(CH_2)_2$—NHCO—$CH_2$—, —$(CH_2)_3$—NHCO—$(CH_2CH_2O)_{12}$—$(CH_2)_2$—NHCO—$CH_2$— or —$(CH_2)_3$—NHCO—$(CH_2)_3$—NHCO—$(CH_2CH_2O)_4$—$(CH_2)_2$—NHCO—$CH_2$—.

25. The compound as defined in claim 2, wherein $S_2$ represents —$(CH_2)_e$—, wherein one or two of said —$CH_2$— groups are optionally substituted by —$(CH_2)_3$—NHCO—$CH_2$—.

26. The compound as defined in claim 2, wherein $S_2$ represents —$(CH_2)_f$—$(CH_2$—$CH_2$—$O)_g$—$(CH_2)_h$—, wherein one to three of said —$CH_2$— groups are optionally substituted by —$(CH_2)_3$—NHCO—$(CH_2CH_2O)_4$—$(CH_2)_2$—NHCO—$CH_2$—.

27. The compound as defined in claim 2, wherein $S_2$ represents —$(CH_2)_e$—, wherein one or two of said —$CH_2$— groups are optionally substituted by —$(CH_2)_3$—NHCO—$CH_2$—).

28. The compound as defined in claim 2, wherein $S_2$ represents —$(CH_2)_e$—, wherein one of said —$CH_2$— groups is optionally substituted by —$(CH_2)_3$—NHCO—$CH_2$—.

29. The compound as defined in claim 2, wherein $S_2$ represents —$(CH_2)_f$—$(CH_2$—$CH_2$—$O)_g$—$(CH_2)_h$—, wherein two of said —$CH_2$— groups are optionally substituted by —$(CH_2)_3$—NHCO—$(CH_2CH_2O)_4$—$(CH_2)_2$—NHCO—$CH_2$—.

30. The compound as defined in claim 5, wherein the antigen binding fragment thereof is selected from the group consisting of Fab, Fab', F(ab)$_2$, F(ab')2, and scFv.

31. The compound as defined in claim 6, wherein the antibody or antigen binding fragment thereof is cetuximab, cetuximab Fab or nimotuzumab.

32. The compound as defined in claim 31, wherein the antibody or binding fragment thereof is an EGFR antibody or fragment thereof having at least 80% sequence identity to SEQ ID NOS: 1 to 4.

33. The compound as defined in claim 14, wherein the antibody or antigen binding fragment thereof is rituximab or rituximab Fab.

34. The method of claim 11, wherein the cancer is haematological cancer.

35. The method of claim 34, wherein the haematological cancer is a leukemia or a lymphoma.

* * * * *